United States Patent
Heym et al.

[11] Patent Number: 5,851,763
[45] Date of Patent: Dec. 22, 1998

[54] RAPID DETECTION OF ANTIBIOTIC RESISTANCE IN MYCOBACTERIUM TUBERCULOSIS

[75] Inventors: Beate Heym, Ville d'Avray; Stewart Cole, Clamart, both of France; Douglas Young, Ruislip; Ying Zhang, London, both of United Kingdom; Nadine Honore, Colombes, France; Amalio Telenti, Gerzensee; Thomas Bodmer, Ersigen, both of Switzerland

[73] Assignee: Institut Pasteur, Paris, France

[21] Appl. No.: 313,185

[22] PCT Filed: Apr. 30, 1993

[86] PCT No.: PCT/EP93/01063

§ 371 Date: May 9, 1995

§ 102(e) Date: May 9, 1995

[87] PCT Pub. No.: WO93/22454

PCT Pub. Date: Nov. 11, 1993

[30] Foreign Application Priority Data

Sep. 17, 1992 [FR] France ................... 92 11098
Apr. 16, 1993 [FR] France ................... 93 04545

[51] Int. Cl.⁶ .................. C12P 19/34; C12Q 1/68; C07H 21/04; C07H 21/00
[52] U.S. Cl. .................. 435/6; 435/91.1; 435/91.2; 536/24.3; 536/24.32; 536/25.3; 536/26.6
[58] Field of Search .................. 435/6, 91.2, 91.1; 536/24.3, 24.32, 25.3, 26.6

[56] References Cited

U.S. PATENT DOCUMENTS 4,683,195  7/1987  Mullis et al. ................... 435/6
5,633,131  5/1997  Heym et al. ................... 435/6

FOREIGN PATENT DOCUMENTS 0 223 156      5/1987  European Pat. Off. .
WO 9 106 674   5/1991  WIPO .
WO 95/33074   12/1995  WIPO .

OTHER PUBLICATIONS

Heym et al. (1992), Research in Microbiology, vol. 143, No. 7, pp. 721–730.

Jin et al. (1988), Journal of Molecular Biology, vol. 202, No. 1, pp. 45–58.

Sriprakash et al. (1970), The Journal of General Microbiology, vol. 60, No. 1, pp. 125–132.

Telenti et al. (1993), The Lancet, vol. 341, No. 8846, pp. 647–650.

Zhang et al. (1992), Nature, vol. 358, No. 6387, pp. 591–593.

*Primary Examiner*—Kenneth R. Horlick
*Assistant Examiner*—Joyce Tung
*Attorney, Agent, or Firm*—Finnegan, Henderson, Farabow, Garrett & Dunner, L.L.P.

[57] ABSTRACT

A process for the detection of resistance to an antibiotic in a mycobacterium comprises detecting a mutation in a gene selected from the group consisting of the katG gene or fragment thereof, the rpoB gene or fragment thereof, and the rpsI gene or fragment thereof. The process is useful for detecting in vitro the presence of nucleic acids of a *Mycobacterium tuberculosis* resistant to isoniazid.

21 Claims, 26 Drawing Sheets

<--------- lacZ' -------------->

M T M I T P S L H A C R S T L E D P H P T L R
ATGACCATGATTACGCCAAGCTTGCATGCCTGCAGGTCGACTCTAGAGGATCCCCATCGACACTTCGCG
          10         20         30         40         50         60        70 katG------>

M S T S D D - - I H N T T A T G K C P F H Q G
* ::
M P E Q H P P I T E T T T G A A S N G C P V V
GTGCCCGAGCAACACCCACCGATTACAGAAACCACCACCGGAGCCGCTAGCAACGGCTGTCCCGTCGTGG
         130        140        150        160        170        180       190

N Q L R V D L L N Q H S N R S N P L G E D F D
* ::        * ::            ::    *      * *
N R L N L K V L H Q N P A V A D P M G A A F D
AACCGGCTCAATCTGAAGGTACTGCACCAAAACCCGGCCGTCGCTGACCCGATGGGTGCGGCGTTCGACT
         250        260        270        280        290        300       310

FIG. 2C(1)

```
D  H  I  R  D  H  S  P  I  T  P  T  P  G  R  N  A
ATCACATCCGTGATCACAGCCCGATAACACCAACTCCTGGAAGGAATGCT                        E.coli
       80        90       100       110       120

G  H  D  Q  S  A  G  A  G  T  T  R  D  W  W  P              M.tub
*  *              :     *  :  :     *     *  *
G  H  M  K  Y  P  V  E  G  G  N  Q  D  W  W  P
GTCATATGAAATACCCCGTCGAGGGCGGAAACCAGGACTGGTGGCCC
      200       210       220       230       240

Y  R  K  E  F  S  K  L  D  Y  Y  G  L  K  K  D  L          E.coli
*  *     *  :  :        :        :     *  :  :
Y  A  A  E  V  A  T  S  R  L  D  A  L  T  R  D  I          M.tub
ATGCCGCGGAGGTCGCGACCAGTCGACTCGACTTGACGCCCTGACGCGGGACATC
      320       330       340       350       360
```

FIG. 2C(2)

```
GGTACCGTGA  GGCGATGGGT  GGCCCGGGGC  CCGGCTGTCT  GGTAAGCGCCG  GCCGCAAAAC    60
AGCTGTACTC  TCGAATCCCA  GTTAGTAACA  ATGTGCTATG  GAATCTCCAA   TGACGAGCAC   120
ACTTCACCGA  ACCCCATTAG  CCACCGCGGG  GCTGGCCTC   GTAGTGGCGC   TGGGTGGCTG   180
CGGGGGCGGG  GCCGGTGACA  GTCGAGAGAC  ACCGCCATAC  GTGCCGAAAG   CGACGACCGT   240
CGACGCAACA  ACGCCGGCGC  CGGCCGCCGA  GCCACTGACG  ATCGCCAGTC   CCATGTTCGC   300
CGACGGCGCC  CCGATCCCGG  TGCAATTCAG  CTGCAAGGGG  GCCAACGTGG   CCGCCACCGT   360
TGACGTGGTC  GTCGCCCGCG  GCGAGCGAAC  TGGCACTCGT  CGTCGATGAC   CCCGACGCGG   420
TCGGCGGACT  GTACGTGCAC  TGGATCGTGA  CCGGAATCGC  CCCTGGCTCT   GGCAGCACGG   480
CGGATGGTCA  GACTCCTGCT  GGTGGGCACA  GCGTGCCGAA  TTCTGGTGGT   CGGCAAGGAT   540
ACTTCGGTCC  ATGCCCGCCG  GCGGGCACCG  GGACACACCA  CTACCGGTTT   ACCCTCTACC   600
ACCTTCCTGT  CGCGCTCCAG  CTGCCACCGG  GAGCCACGGG  AGTCCAAGCG   GCACAGGCGA   660
TAGCACAGGC  CGCCAGCGAC  AGGCCCGGCT  CGTCGGCACA  TTCGAAGGCT   GACGCCGCGG   720
CATCCCTGGC  GAGGTGGTCG  AAACCCTGGC  TTCTCCAATT  GCGCCTGGCG   ACAATGATCA   780
ATATGGAATC  GACAGTGGCG  CACGCCATTTC  ACCGGTTCGC ACTGGCCATC   TTGGGGCTGG   840
CGCTCCCCGT  GGCGCTAGTT  GCCTACGGTG  GCAACGGTGA  CAGTCGAAAG   GCGGGGGCCG   900
TGGCGCCGAA  AGCAGCAGCG  CTCGGTCGGA  GTATGCCCGA  AACGCCTACC   GGCGATGTAC   960
TGACAATCAG  CAGTCCGGCA  TTCGCCGACG  TGGTCGGCGC  CCCGGAACAG   TACACCTGCA  1020
AAGGAGCCAA  TATCGCGGCC  TCCGTTGACC  TGGTCGGCGC  CGTTTGGCGG   CGCACTCGTT  1080
GTCGATGATC  CGGACCACCT  CGGAACCTT   ACGTCCATTG  GATCGTGATC   GGGATCGCCC  1140
CTGGTGCTGG  CAGCAGCCGA  TGGTGAGACT  CCCGGTGCCG  GAATCAGCCT   GCCGAACTCC  1200
AGCCGGTCAGC  CCGCATACAC  CGGCCCCTGC  CCGCCGGCGG  CGACCGGGAC   ACACCACTAC  1260
```

FIG. 6A-1

```
CGGTTTACCC TCTACCACCT TCCTGCCGTG CCTCCACTCG CGGGACTGGC TGGACACAA    1320
GCGGGCGGGG TGATCGGCA GCCGCCACC ATGCAGGCCC GGCTCATCGG AACATACGAA    1380
GGCTGATCCA CCCGCCATCC CACGATCCAG CGGCCCCGGG CGATCGGGTC CTAGCAGACG  1440
CCTGTCACGC TAGCCAAAGT CTTGACTGAT TCCAGAAAAG GGAGTCATAT TGTCTAGTGT  1500
GTCCTCTATA CCGGACTACG CCGAACAGCT CCGGACGGCC GACCTGCGCG TGACCCGACC  1560
GCGCGTCGCC GTCCTGGAAG CAGTGAATGC GCATCCACAC GCCGACACGG AAACGATTTT  1620
CGGTGCCGTG CGTTTTGCGC TGCCCGACGT ATCCGGCAAG CCGTGTACGA CGTGCTGCAT  1680
GCCCTGACCG CCGCGGGCTT GGTGCCGAAAG ATCCAACCCT CGGGCTCCGT CGCGGCTAC  1740
GAGTCCAGGG TCGGCGACAA CCACCATCAC ATCGTCTGCC GGTCTTGCGG GGTTATCGCC  1800
GATGTCGACT GTGCTGTTGG CGAGGCACCC TGTCTGACGG CCTCGGACCA TAACGGCTTC  1860
CTGTTGGACG AGGCGGAGGT CATCTACTGG GGTCTATGTC CTGATTGTTC GATATCCGAC  1920
ACTTCGCGAT CACATCCGTG ATCACACGCC GATAACACCA ACTCCTGGAA GGAATGCTGT  1980
GCCCGAGCAA CACCCACCCA TTACAGAAAC CACCACCGGA GCCGCTAGCA ACGGCTGTCC  2040
CGTCGTGGGT CATATGAAAT ACCCCGTCGA GGGCGGGCGA AACCAGGACT GGTGGCCCAA  2100
CCGGCTCAAT CTGAAGGTAC TGCACCAAAA CCCGGCCGTC GCTGACCCGA TGGGTGCGGC  2160
GTTCGACTAT GCCGCGGAGG TCGCGGACAG TCGACTTGAC GCCCTGACGC GGGACATCGA  2220
GGAAGTGATG ACCACCTCGC AGCCGTGGTG GCCCGCCGAC TACGGCCACT ACGGGCCGCT  2280
GTTTATCCGG ATGGCGTGGC ACGCTGCCGG CACCTACCGC ATCCACGACG GCCGGGGCGG  2340
CGCCGGGGGC GGCATGCAGC GGTTCGCGCC GCTTAACAGC TGGCCCGACA ACGCCAGCTT  2400
GGACAAGGCG CGCGGCTGC TGTGGCCGGT CAAGAAGAAG TACGGCAAGA AGCTCTCATG   2460
GGCGGACCTG ATTGTTTTCG CCGGCAACCG CTGCGCTCGG AATCGATGGG CTTCAAGACG  2520
TTCGGGTTCG GCTTCGGGCG TCGACCAGTG GGAGACCGAT GAGGTCTATT GGGGCAAGGA  2580
```

FIG. 6A-2

```
AGCCACCTGG CTCGGGGATG ACGGTTACAG CGTAAGCGAT CTGGAGAACC CGCTGGCCGC  2640
GGTGCAGATG GGGCTGATCT ACGTGAACCC GGAGGCGCCG AACGGCAACC CGGACCCCAT  2700
GGCCGCGGCG GTCGACATTC GCGAGACGTT TCGGCGCATG GCCATGAACG ACGTCGAAAC  2760
AGCGGCGCTG ATCGTCGGCG GTCACACTTT CGGTAAGACC CATGGCGCCG GCCCGGCCGA  2820
TCTGGTCGGC CCCGAACCCG AGGCTGCTCC GCTGGAGCAG ATGGGCTTGG GCTGGAAGAG  2880
CTCGTATGGC ACCGGAACCG GTAAGGACGC GATCACCAGC GGCATCGAGG TCGTATGGAC  2940
GAACACCCCG ACGAAATGGG ACAACAGTTT CCTCGAGATC CTGTACGGCT ACGAGTGGGA  3000
GCTGACGAAG AGCCCTGCTG GCGCTTGGCA ATACACCGCC AAGGACGGCG CCGGTGCCGG  3060
CACCATCCCG GACCCGTTCG GCGGGCCAGG GCGCTCCCCG ACGATGCTGG CCACTGACCT  3120
CTCGCTGCGG GTGGATCCGA TCTATGAGCG CGCTGGCTGG CGCTGGCTGG AACACCCCGA  3180
GGAATTGGCC GACGAGTTCC GCAAGGCCTG GTACAAGCTG ATCCACCGAG ACATGGGTCC  3240
CGTTGCCGAGA AGCCCTGGGC CGCTGGTCCC CAAGCAGACC CTGCTGTGCC AGGATCCGGT  3300
CCCTGCGGTC TACCTTGGGC CGCTGGTCCC CAAGCAGACC CTGCTGTGCC AGGATCCGGT  3300
GGCATCGGGA TTGACTGTCT CACAGCTAGT TTCGACCGCA TGGGCGGCGG CGTCGTCGTT  3420
CCGTGGTAGC GACAAGCGCG GCGGCGCCAA CGGTGGTCGC ATCCGCCTGC AGCCACAAGT  3480
CGGGTGGGAG GTCAACGACC CCGACGGATC TGCGCAAGGT CATTCGCACC CTGAAGAGAT  3540
CCAGGAGTCA TTCACTCGGC GCGGGAACAT CAAAGTGTCC TTCGCCGACC TCGTCGTGCT  3600
CGGTGGCTGT GCGCCACTAG AGAAAGCAGC AAAGGCGGCT GGCCACAACA TCACGGTGCC  3660
CTTCACCCCG GGCCCCGCACG ATGCGTCGCA GGAACAAACC GACGTGGAAT CCTTTGCCGT  3720
GCTGGAGCCC AAGGCCGAACCT GCTTCCGAAA AGGCGAACCT CTACCTCGGA AAGGGCAACC GTTGCCGGCC  3780
GAGTACATCG CTGCTCGACA AGGCGAACCT GCTTACGCTC AGTGCCCCTG AGATGACGGT  3840
GCTGGTAGGT GGCCTGCGCG TCCTCGGCGC AAACTACAAG CGCTTACCGC TGGGCGTGTT  3900
```

FIG. 6A-3

```
CACCGAGGCC TCCGAGTCAC TGACCAACGA CTTCTTCGTG AACCTGCTCG ACATGGGTAT   3960
CACCTGGGAG CCCTCGCCAG CAGATGACGG GACCTACCAG GGCAAGGATG GCAGTGGCAA   4020
GGTGAAGTGG ACCGGCAGCC GCGTGGACCT GGTCTTCGGG TCCAACTCGG AGTTGCGGGC   4080
GCTTGTCGAG GTCTATGCGC CGATGACGCG GCAGGCGAAG TTCGTGACAG GATTCGTCGC   4140
TGCGTGGGAC AAGGTGATGA ACCTCGACAG GTTCGACGTG CGCTGATTCG GGTTGATCGG   4200
CCCTGCCCGC CGATCAACCA CAACCCGCCG CAGCACCCCG CGAGCTGACC GGCTCGCGGG   4260
GTGCTGGTGT TTGCCCGGCG CGATTTGTCA GACCCCGCGT GCATGGTGGT CGCACGGACG   4320
CACGAGACGG GGATGACGAG ACGGGGATGA GGAGAAAGGG CGCCGAAATG TGCTGGATGT   4380
GCGATCACCC GGAAGCCACC GCCGAGGAGT ACCTCGACGA GGTGTACGGG ATAATGCTCA   4440
TGCATGGCTG GGCGGTACAG CACGTGGAGT GCGAGCGACG GCCATTTGCC TACACGGTTG   4500
GTCTAACCCG GCGCGGCTTG CCCGAACTGG TGGTGACTGG CCTCTCGCCA CGACGTGGGC   4560
AGCGGTTGTT GAACATGCCG TCGAGGGCTC TGGTCGGTGA CTTGCTGACT CCCGGTATGT   4620
AGACCACCCT CAAAGCCGGC CCTCTTGTCG AAACGGTCCA GGCTACACAT CCGGACGCGC   4680
ATTTGTATTG TGCGATCGCC ATCTTTGCGC ACAAGGTGAC GGCCTTGCAG TTGGTGTGGG   4740
CCGACCGCGT GGTCGCTGGC CGTGGGCGGC CGACTTCGAC GAAGGTCGCG GTACC        4795
```

```
     1241             1251        1261             1271        1281             1291
     CAGCCTGCCG AACTCCAGCG GTCAGCCCGC ATACACCGGC CCCTGCCCGC CGGCGGGCAC
     ****  **** ** ******* ***  **** ****  **** ** ****** ********
     CAGCGTGCCG AATTCTGGTG GTCGGCAAGG ATACTTCGGT CCATGCCCGC CGGCGGGCAC
541                   561             571             581             591
1301
     CGGGACACAC CACTACCGGT TTACCCTCTA CCACCTTCCT GCCGTGCCTC CA-CTCGC--
     ********** ********** ********** ********** *  ** *** **  **
     CGGGACACAC CACTACCGGT TTACCCTCTA CCACCTTCCT GTCGCGC-TC CAGCT-GCCA
601                   621             631             641             651
1361         1371        1381             1391        1401             1411
     --GGGACTGG CT--GGGA-- CACAAGCGGC GCGGGTGATC GGGCAGGCCG CCACCATG-C
       *  *        ***     *  ****** *  ** ***  ********** ***  *
     CCGGGA----G CCACGGGAGT C-CAAGCGGC ACAGGCGATA GCACAGGCCG CCAGC---GAC
661                   681             691             701             711
1421        1431             1441        1451             1461
     AGCCCCGGCT CATCGGAACA TACGAAGGCT GATCCACCCG CCATCC
     ********** *  ****    *********
     AGGCCCGGCT CGTCGGCACA ---------- ---------- ------
721                   741             751             761
```

FIG. 6B-2

```
                                                                                    70
MTKATG    1 MPEQHPPITE TTTGAASNGC PVVGHMKYPV EGGGNQDWWP NRLNLKVLHQ NPAVADPMGA AFDYAAEVAT
ECKATG      ..MSTSDDIH NTTATGKCPF HQGGHDQSAG AGTTTRDWWP NQLRVDLLNQ HSNRSNPLGE DFDYRKEF..
STKATG      ..MSTTDDTH NTLSTGKCPF HQGGHDRSAG AGTASRDWWP NQLRVDLLNQ HSNRSNPLGE DFDYRKEF..
BSPERA      ....MENQ.. NRQNAAQCPF HESVTNQSS. NRTTNKDWWP NQLNLSILHQ HDRKTNPHDE EFNYAEEFQ.
(CCP)       .......... NTT.---KCPF .......... .......... ...TTPLVHV ASVEKGRSYE DFQ.......
CONSENSUS  --MST-DDTH NTT----KCPF HQGGHDQSAG AGTTNRDWWP NQL--DLLHQ HSNRSNPLGE DFDY-KEF--

140
MTKATG   71 SRLD...ALT RDIEEVMTTS QPWWPADYGH YGPLFIRMAW HAAGTYRIHD GRGGAGGGMQ RFAPLNSWPD
ECKATG      SKLDY.GLK  KDLKALLTES QPWWPADWGS YAGLFIRMAW HGAGTYRSID GRGGAGRGQQ RFAPLNSWPD
STKATG      SKLDYYSALK GDLKALLTDS QPWWPADWGS YVGLFIRMAW HGAGTYRSID GRGGAGRGQQ RFAPLNSWPD
BSPERA      .KLDYW.ALK EDLRKLMTES QDWWPADYGH YGPLFIRMAW HSAGTYRIGD GRGGASTGTQ RFAPLNSWPD
(CCP)       .KVYNAIALK .......... DEY...DNYIG YGPVLVRLAW HISGTWDKHD NTGGSYGGTY RFKKEFNDPS
CONSENSUS  SKLDYY-ALK -DLKALLTES QPWWPADYG- YGPLFIRMAW HGAGTYR---D GRGGAG-G-Q RFAPLNSWPD
                                                  R       W      H(108)

210
MTKATG  141 NASLDKARRL LWPVKKKYGK KISWADLIVF AGNRCARNRW ASRRSGSASG ...VDQWETD .EVYWGKEAT
ECKATG      NVSLDKARRL LWPIKKKYGQ KISWADLIWL AGNVALENSG FRTFGFGAGR ....EDVWEPD LDVNWGDEKA
STKATG      TVSLDKARRL LWPIKQKYGQ KISWADLFIL AGNVALENSG FRTFGFGAGR ...EDVWEPD LDVNWGDEKA
BSPERA      NANLDKARRC YGRSKRNTGT K.SLGPICSF WRAMSLLNRW VEKRLDSAAG PLTSGIRKKT FIGDRKKSGS
(CCP)       NAGLQNGFKF LEPIHKEFP. WISSGDLFSL GGVTAVQEMQ GPKIPWRCGR VDTPEDTTPD ....NG
CONSENSUS  NASLDKARRL LWPIK-KYGQ KISWADLFIL AGNVALEN-- FR--GF-AGR -TEDVWEPD LDVNWG-EKA
                                                                        H(138)

280
MTKATG  211 WLGDDGYSVS DLENPLAAVQ MGLIYVNPEA PNGNPDPMAA AVDIRETFRR MAMNDVETAA LIVGGHTFGK
ECKATG      WLTHR.HPEA LAKAPLGATE MGLIYVNPEG PDHSGEPLSA AAAIRATFGN MGMNDEETVA LIAGGHTLGK
STKATG      WLTHR.HPEA LAKAPLGATE MDLIYVTPEG PNHSGEPLSA AAAIRATFGN MGMNDEETVA LIAGGHTLGK
BSPERA      PLNAIPVIAS SKTRSPRANG VNLRQPRRAG RQAGSKSRGI SA....ETFRR MGMNDEETVA LIAGGHTFGK
(CCP)       RL......HR LEPIHKEFP. .......... PNHS--PLSA AGYVRTFFQR LNMNDREVVA LM.GAHALGK
CONSENSUS  WLTHR-HPE- LAKAPLGATE -MGLIYVNPEG PNHS--PLSA AAAIR-TF-R MGMNDEETVA LIAGGHTLGK
            N(138)                                                              H(269)

350
MTKATG  281 THGAGPADLV GPEPEAAPLE QMGLGWKSSY GTGTGKDAIT SGIEVVWTNT PTKWDNSFLE ILYGYEWELT
ECKATG      THGAGPTSNV GPDPEAAPIE EQGLGWASTY GSGVGADAIT SGLEVVWTQT PTQWSNYFFE NLFKYEWVQT
STKATG      THGPAAASHV GADPEAAPIE AQGLGWASSY GSGVGADAIT SGLEVVWTQT PTQWSNYFFE NLFKYEWVQT
BSPERA      AHRGGPATHV GPEPEAAPIE AQGLGWISSY GKGKGSDTIT SGIEGAWTPT PTQWDTSYFD MLFGYDWLT
(CCP)       TH........ GP-PEAAPIE AQGLGWASSY LKN....... SGYEGPWGAA NNVFTNEFYL NLLNEDWKLE
CONSENSUS  THGAGPASHV GP-PEAAPIE AQGLGWASSY GSGVGADAIT SG--EVVWTQT PTQW-N-FFE NLF--YEWVLT
            TH(275)                                                     W(320)

420
MTKATG  351 KSPAGAWQYT AKDGAGAGTI PDPFGGPGR. ..SPTMLATD LSLRVDPIYE RITRRWLEHP EELADEFRKA
ECKATG      RSPAGAIQFE AVD...APEII PDPFDPSKKR ..KPTMLVTD LTLRFDPEFE KISRRFLNDP QAFNEAFARA
STKATG      RSPAGAIQFE AVD...APDII PDPFDPSKKR XXKPTMLVTD LTLRFDPEFE KISRRFLNDP QAFNEAFARA
BSPERA      LALRFDPEYE KIARRFHQNP EEFAEAFARA APDII PDAEDPSKK.
(CCP)       KSPAGAWQWM AVDPDEKDLA PDAEDPSKK. .VPTMMMTTD YSLIQDPKYL SIVKEYANDQ DKFFKDFSKA
CONSENSUS  KSPAGA-Q-E AVDG-APDII PDPFDPSKKR --KPTMLVTD L-LRFDPEYE KISRRFLNDP E-F-EAFARA
                                                        D(380)
```

FIG. 8A

```
         421
(MTKATG) WYKLTHRDM....GPVARYL  GPLVPKQTLL  WQDPVPAVST  TSSAKQIASL  KSQIRASGLT  VSQLVSTAWA
(ECKATG) WFKLTHRDM....GPKSRYI  GPEVPKEDLI  WQDPPLPQPIY  NPTEQDIIDL  KFAIADSGLS  VSELVSVAWA
(STKATG) WFKLTHRDM....GPKARYI  GPEVPKEDLI  WQDPLPQPLX  QPTQEDIINL  KAAIAASGLS  ISEMVSVAWA
(BSPERA) WFKLTHRDM....GPKTRYL  GPEVPKEDFI  WQDPIPEVDY  ELTEAEIEEI  KAKILNSGLT  VSELVKTAWA
  (CCP)  FEKLLENGIT  FPKDAPSPFI  FKTLEEQGL.  ......     .PTE-DII-L  KAAIAASGL-  -VSELVS-AWA
CONSENSUS WFKLTHRDM-  ---GPK-RYI  GPEVPKEDLI  WQDP-PQ---Y                                  490

491                                                                                 560
(MTKATG) AASSFRGSDK  RGGA.NGGRI  RLQPQVGWEV  NDPDGSAQGH  SHPEEIQESF  TRRGNIKVSF  ADLVVLGGCA
(ECKATG) SASTFRGGDK  RGGA.NGARL  ALMPQRDWDV  N..AAAVRAL  PVLEKIQ...  .KESGKASL  ADIIVLAGVV
(STKATG) SASTFRGGDK  RGGA.NGARL  ALAPQRDWDV  N..AVAARVL  PVLEEIQ...  .KTTNKASL  ADIIVLAGVV
(BSPERA) SAA..RSATR  ISAATNGRRI  RLAPQKDWEV  NEPERLAKVL  SVLRGHPA..  .RTAEKSKH  RRLDRLGGTL
  (CCP)  .......... ..........  .LAPQRDW-V  .N-P---AARVL  -VLEEIQ---  ---T--KASL  AD-IVL-GVV
CONSENSUS SASTFRGGDK  RGGA-NGAR- 561                                                                                 630
(MTKATG) PLEKAAKAAG  HNITVPF...  TPGPHDASQE  QTDVESFAVL  EPKADGFRN.  ...YLGKGNR  CRPSTSLLDK
(ECKATG) GVEKAASAAG  LSIHVPF...  APGRVDARQD  QTDIEMFELL  EPIADGFRN.  ...YRARLDV  STTESLLIDK
(STKATG) GIEQAAAAAR  VSIHVPF...  PPGRVDARHD  QTDIEMFSLL  EPIADGFRN.  ...YRARLDV  STTESLLIDK
(BSPERA) RWKRQPATPA  LMSKCHFSLA  AAMRHKSKPM  SKALPCWNRS  QMASATIKSK  STRFRRKSCS  STKPSSADR
  (CCP)  .G-EKAAAAAG  LSIHVPF---  .APGR-DARQD  QTDIEMF-LL  EPIADGFRN-  ---YRA-LDV  STTES-LIDK
CONSENSUS 631                                                                                 700
(MTKATG) ANLLTLSAPE  MTVLVGGLRV  LGANYKRLPL  GVFTEASESL  TNDFFVNLLD  MGITWEPSPA  DDGTYQGKD.
(ECKATG) AQQLTLTAPE  MTALVGGMRV  LGGNFDGSKN  GVFTDRVGVL  SNDFFVNLLD  MRYEWKATDE  SKELFEGRDR
(STKATG) AQQLTLTAPE  MTVLVGGMRV  LGTNFDGSQN  GVFTDKPGVL  STDFFANLLD  MRYEWKPTDD  ANELFEGRDR
(BSPERA) PRNDGLSWR.  ......FAR   VGPNYRHLPH  GVFTDRIGVL  TNDFFVNLLD  MNYEWVPTDS  ..GIYEIRDR
  (CCP)  AQQLTL-APE  MTV-LVGGMRV  LG-N--DG-PN  GVFTDR-GVL  -NDFFVNLLD  MRYEWKPTD-  ---L-EGRDR
CONSENSUS 701                                      767
(MTKATG) GSGKVKWTGS  RVDLVFGSNS  ELRALVEVYA  PMTRQAKFVT  GFVAAWDKVM  NLDRFDVR..
(ECKATG) ETGEVKFTAS  RADLVFGSNS  VLRAVAEVYA  SSDAHEKFVK  DFVAAWVKVM  NLDRFDLL..
(STKATG) LTGEVKYTAT  RADLVFGSNS  VLRALAEVYA  CSDAHEKFVK  DFVAAWVKVM  NLDRFDLQ..
(BSPERA) KTGEVRWTAT  RVDLIFGSNS  ILRSYAEFYA  QDDNQEKFVR  DFINAWVKVM  NADRFDLVKK  ARESVTA
  (CCP)  -TGEVKWTA-  R-DLVFGSNS  VLRALAEVYA  -SDA--EKFVK  DFVAAWVKVM  NLDRFDL---
CONSENSUS
```

FIG. 8B

CAG TTC ATG GAT CAG AAC AAC CCT CTG TCG GGC CTG ACC CAC AAG CGC CGG CTG TCG → TTG
                                                                              ATG
                                                                              TTC rpoB88 { TTC AAG }
rpoB1,2,4,5,6,7
rpoB3
rpoB9

FIG. 11A

```
                            1    1 4 4 2 4        1                  2    3    4 1   3 1 1    1
                                 L P N V D Q      Δ                  F    Y    C S   F P      Δ
Frequence
E.Coli     505  F F G S S Q L S Q F M D Q N N P L S E I T H K R R I S A L G P G G  537
M.Leprae   399  F F G T S Q L S Q F M D Q N N P L S G L T H K R R L S A L G P G G  431
                                       F K                                 L F M
M.Leprae                                 1                                 6 1 1
Frequence
```

FIG. 11B

```
ValProGlyAlaProAsnArgIleSerPheAlaLysLeuArgGluProLeuGluValPro
GTGCCCGGCGCGCCCAACCGAATTTCATTTGCCAAGCTCCGCGAACCGCTTGAGGTTCCG                60

GlyLeuLeuAspValGlnThrAspSerPheGluTrpLeuIleGlySerProCysTrpArg
GGGCTACTTGATGTGCAGACTGATTCATTTGAGTGGTTGATCGGATCGCCGTGCTGGCGT                120

AlaAlaAlaAlaSerArgGlyAspLeuLysProValGlyGlyLeuGluGluValLeuTyr
GCAGCGGCCGCAAGCCGCGGCGATCTCAAGCCGGTGGGTGGTCTCGAAGAGGTGCTCTAC                180

GluLeuSerProIleGluAspPheSerGlySerMetSerLeuSerPheSerAspProArg
GAGCTGTCGCCGATCGAGGATTTCTCCGGCTCAATGTCATTGTCTTTCTCCGATCCCCGT                240

PheAspGluValLysAlaProValGluGluCysLysAspLysAspMetThrTyrAlaAla
TTTGACGAAGTCAAGGCGCCCGTCGAAGAGTGCAAAGACAAGGACATGACGTACGCGGCC                300

ProLeuPheValThrAlaGluPheIleAsnAsnAsnThrGlyGluIleLysSerGlnThr
CCGCTGTTCGTCACGGCCGAGTTCATCAACAACAACACCGGGGAGATCAAGAGCCAGACG                360

ValPheMetGlyAspPheProMetMetThrGluLysGlyThrPheIleIleAsnGlyThr
GTGTTTATGGGCGACTTCCCTATGATGACTGAGAAGGGAACCTTCATCATCAACGGGACC                420

GluArgValValValSerGlnLeuValArgSerProGlyValTyrPheAspGluThrIle
GAGCGTGTCGTCGTTAGCCAGCTGGTGCGCTCCCTGGAGTATACTTCGACGAGACGATC                480

AspLysSerThrGluLysThrLeuHisSerValLysValIleProSerArgGlyAlaTrp
GACAAGTCCACAGAAAAGACGCTGCATAGTGTCAAGGTGATTCCCAGCCGCGGTGCCTGG                540

LeuGluPheAspValAspLysArgAspThrValGlyValArgIleAspArgLysArgArg
TTGGAATTCGATGTCGATAAACGCGACACCGTCGGTGTCCGCATTGACCGGAAGCGCCGG                600

GlnProValThrValLeuLeuLysAlaLeuGlyTrpThrSerGluGlnIleThrGluArg
CAACCCGTCACGGTGCTTCTAAAGCGCTAGGTTGGACCAGTGAGCAGATCACCGAGCGT                660

PheGlyPheSerGluIleMetArgSerThrLeuGluLysAspAsnThrValGlyThrAsp
TTCGGTTTCTCCGAGATCATGCGCTCGACGCTGGAGAAGGACAACACAGTTGGCACCGAC                720

GluAlaLeuLeuAspIleTyrArgLysLeuArgProGlyGluProProThrLysGluSer
GAGGCGCTGCTAGACATCTATCGTAAGTTGCGCCCAGGTGAGCCGCCGACTAAGGAGTCC                780

AlaGlnThrLeuLeuGluAsnLeuPhePheLysGluLysArgTyrAspLeuAlaArgVal
GCGCAGACGCTGTTGGAGAACCTGTTCTTCAAGGAGAAACGCTACGACCTGGCCAGGGTT                840

GlyArgTyrLysValAsnLysLysLeuGlyLeuHisAlaGlyGluLeuIleThrSerSer
GGTCGTTACAAGGTCAACAAGAAGCTCGGGTTGCACGCCGGTGAGTTGATCACGTCGTCC                900

ThrLeuThrGluGluAspValValAlaThrIleGluTyrLeuValArgLeuHisGluGly
ACGCTGACCGAAGAGGATGTCGTCGCCACCATAGAGTACCTGGTTCGTCTGCATGAGGGT                960
```

FIG. 12A

```
GlnSerThrMetThrValProGlyGlyValGluValProValGluThrAspAspIleAsp
CAGTCGACAATGACTGTCCCAGGTGGGGTAGAAGTGCCAGTGGAAACTGACGATATCGAC         1020

HisPheGlyAsnArgArgLeuArgThrValGlyGluLeuIleGlnAsnGlnIleArgVal
CACTTCGGCAACCGCCGGCTGCGCACGGTCGGCGAATTGATCCAGAACCAGATCCGGGTC         1080

GlyMetSerArgMetGluArgValValArgGluArgMetThrThrGlnAspValGluAla
GGTATGTCGCGGATGGAGCGGGTGGTCCGGGAGCGGATGACCACCCAGGACGTCGAGGCG         1140

IleThrProGlnThrLeuIleAsnIleArgProValValAlaAlaIleLysGluPhePhe
ATCACGCCGCAGACGCTGATCAATATCCGTCCGGTGGTCGCCGCTATCAAGGAATTCTTC         1200

GlyThrSerGlnLeuSerGlnPheMetAspGlnAsnAsnProLeuSerGlyLeuThrHis
GGCACCAGCCAGCTGTCGCAGTTCATGGATCAGAACAACCCTCTGTCGGGCCTGACCCAC         1260

LysArgArgLeuSerAlaLeuGlyProGlyGlyLeuSerArgGluArgAlaGlyLeuGlu
AAGCGCCGGCTGTCGGCGCTGGGCCCGGGTGGTTTGTCGCGTGAGCGTGCCGGGCTAGAG         1320

ValArgAspValHisProSerHisTyrGlyArgMetCysProIleGluThrProGluGly
GTCCGTGACGTGCACCCTTCGCACTACGGCCGGATGTGCCCGATCGAGACTCCGGAGGGC         1380

ProAsnIleGlyLeuIleGlySerLeuSerValTyrAlaArgValAsnProPheGlyPhe
CCGAACATAGGTCTGATCGGTTCATTGTCGGTGTACGCGCGGGTCAACCCCTTCGGGTTC         1440

IleGluThrProTyrArgLysValValAspGlyValValSerAspGluIleGluTyrLeu
ATCGAAACACCGTACCGCAAAGTGGTTGACGGTGTGGTCAGCGACGAGATCGAATACTTG         1500

ThrAlaAspGluGluAspArgHisValValAlaGlnAlaAsnSerProIleAspGluAla
ACCGCTGACGAGGAAGACCGCCATGTCGTGGCGCAGGCCAACTCGCCGATCGACGAGGCC         1560

GlyArgSerSerSerArgAlaCysTrpValArgArgLysAlaGlyGluValGluTyrVal
GGCCGTTCCTCGAGCCGCGCGTGTTGGGTGCGCCGCAAGGCGGGCGAGGTGGAGTACGTG         1620

AlaSerSerGluValAspTyrMetAspValSerProArgGlnMetValSerValAlaThr
GCCTCGTCCGAGGTGGATTACATGGATGTCTCGCCACGCCAGATGGTGTCGGTGGCCACA         1680

AlaMetIleProPheLeuGluHisAspAspAlaAsnArgAlaLeuMetGlyAlaAsnMet
GCGATGATTCCGTTCCTTGAGCACGACGACGCCAACCGTGCCCTGATGGGCGCTAACATG         1740

GlnArgGlnAlaValProLeuValArgSerGluArgProLeuValGlyThrGlyMetGlu
CAGCGCCAAGCGGTTCCGTTGGTGCGCAGCGAACGACCGTTGGTGGGTACCGGTATGGAG         1800

LeuArgAlaAlaIleAspAlaGlyHisValValValAlaGluLysSerGlyValIleGlu
TTGCGCGCGGCCATCGACGCTGGCCACGTCGTCGTTGCGGAGAAGTCCGGGGTGATCGAG         1860

GluValSerAlaAspTyrIleThrValMetAlaAspAspGlyThrArgArgThrTyrArg
GAGGTTTCCGCCGACTACATCACCGTGATGGCCGATGACGGCACCCGGCGGACTTATCGG         1920
```

FIG. 12B

```
MetArgLysPheAlaArgSerAsnHisGlyThrCysAlaAsnGlnSerProIleValAsp
ATGCGTAAGTTCGCGCGCTCCAACCACGGCACCTGCGCCAACCAGTCCCGATCGTGGAT         1980

AlaGlyAspArgValGluAlaGlyGlnValIleAlaAspGlyProCysThrGluAsnGly
GCGGGGGATCGGGTCGAGGCCGGCCAAGTGATTGCTGACGGTCCGTGCACTGAGAACGGC         2040

GluMetAlaLeuGlyLysAsnLeuLeuValAlaIleAsnAlaValGlyGlySerThrThr
GAGATGGCGTTGGGCAAGAACTTGCTGGTGGCGATCAATGCCGTGGGAGGGTCAACAACT         2100

AsnGluAspAlaIleIleLeuSerAsnArgLeuValGluGluAspValLeuThrSerIle
AACGAGGATGCGATCATCCTGTCTAACCGACTGGTCGAAGAGGACGTGCTTACTTCGATT         2160

HisIleGluGluHisGluIleAspAlaArgAspThrLysLeuGlyAlaGluGluIleThr
CACATTGAGGAGCATGAGATCGACGCCCGTGACACCAAGCTGGGTGCTGAGGAGATCACC         2220

ArgAspIleProAsnValSerAspGluValLeuAlaAspLeuAspGluArgGlyIleVal
CGGGACATTCCCAACGTCTCCGATGAGGTGCTAGCCGACTTGGACGAGCGGGGCATCGTG         2280

ArgIleGlyAlaGluValArgAspGlyAspIleLeuValGlyLysValThrProLysGly
CGGATTGGCGCGGAGGTTCGTGACGGTGATATCCTGGTTGGCAAGGTCACCCCGAAGGGG         2340

GluThrGluLeuThrProGluGluArgLeuLeuArgAlaIlePheGlyGluLysAlaArg
GAAACTGAGCTGACACCGGAAGAGCGGTTGCTGCGGGCGATCTTCGGCGAAAAGGCCCGC         2400

GluValArgAspThrSerLeuLysValProHisGlyGluSerGlyLysValIleGlyIle
GAGGTCCGTGACACGTCGCTGAAGGTGCCACACGGCGAATCCGGCAAGGTGATCGGCATT         2460

ArgValPheSerHisGluAspAspAspGluLeuProAlaGlyValAsnGluLeuValArg
CGGGTGTTCTCCCATGAGGATGACGACGAGCTGCCCGCCGGCGTCAACGAGCTGGTCCGT         2520

ValTyrValAlaGlnLysArgLysIleSerAspGlyAspLysLeuAlaGlyArgHisGly
GTCTACGTAGCCCAGAAGCGCAAGATCTCTGACGGTGACAAGCTGGCTGGGCGGCACGGC         2580

AsnLysGlyValIleGlyLysIleLeuProAlaGluAspMetProPheLeuProAspGly
AACAAGGGCGTGATCGGCAAGATCCTGCCTGCCGAGGATATGCCGTTTCTGCCAGACGGC         2640

ThrProValAspIleIleLeuAsnThrHisGlyValProArgArgMetAsnValGlyGln
ACCCCGGTGGACATCATCCTCAACACTCACGGGGTGCCGCGGCGGATGAACGTCGGTCAG         2700

IleLeuGluThrHisLeuGlyTrpValAlaLysSerGlyTrpLysIleAspValAlaGly
ATCTTGGAAACCCACCTTGGGTGGGTAGCCAAGTCCGGCTGGAAGATCGACGTGGCCGGC         2760

GlyIleProAspTrpAlaValAsnLeuProGluGluLeuLeuHisAlaAlaProAsnGln
GGTATACCGGATTGGGCGGTCAACTTGCCTGAGGAGTTGTTGCACGCTGCGCCCAACCAG         2820

IleValSerThrProValPheAspGlyAlaLysGluGluGluLeuGlnGlyLeuLeuSer
ATCGTGTCGACCCCGGTGTTCGACGGCGCCAAGGAAGAGGAACTACAGGGCCTGTTGTCC         2880
```

FIG. 12C

```
SerThrLeuProAsnArgAspGlyAspValMetValGlyGlyAspGlyLysAlaValLeu
TCCACGTTGGCCAACCGCGACGGCGATGTGATGGTGGGCGGCGACGGCAAGGCGGTGCTC         2940

PheAspGlyArgSerGlyGluProPheProTyrProValThrValGlyTyrMetTyrIle
TTCGATGGGCGCAGCGGTGAGCCGTTCCCTTATCCGGTGACGGTTGGCTACATGTACATC         3000

MetLysLeuHisHisLeuValAspAspLysIleHisAlaArgSerThrGlyProTyrSer
ATGAAGCTGCACCACTTGGTGGACGACAAGATCCACGCCCGCTCCACCGGCCCGTACTCG         3060

MetIleThrGlnGlnProLeuGlyGlyLysAlaGlnPheGlyGlyGlnArgPheGlyGlu
ATGATTACCCAGCAGCCGTTGGGTGGTAAGGCACAGTTCGGTGGCCAGCGATTCGGTGAG         3120

MetGluCysTrpAlaMetGlnAlaTyrGlyAlaAlaTyrThrLeuGlnGluLeuLeuThr
ATGGAGTGCTGGGCCATGCAGGCCTACGGTGCGGCCTACACGCTGCAGGAGCTGTTGACC         3180

IleLysSerAspAspThrValGlyArgValLysValTyrGluAlaIleValLysGlyGlu
ATCAAGTCCGACGACACCGTCGGTCGGGTCAAGGTTTACGAGGCTATCGTTAAGGGTGAG         3240

AsnIleProGluProGlyIleProGluSerPheLysValLeuLeuLysGluLeuGlnSer
AACATCCCCGAGCCGGGCATCCCCGAGTCGTTCAAGGTGCTGCTCAAGGAGTTACAGTCG         3300

LeuCysLeuAsnValGluValLeuSerSerAspGlyAlaAlaIleGluLeuArgGluGly
CTGTGTCTCAACGTCGAGGTGCTGTCGTCCGACGGTGCGGCGATCGAGTTGCGCGAAGGT         3360

GluAspGluAspLeuGluArgAlaAlaAlaAsnLeuGlyIleAsnLeuSerArgAsnGlu
GAGGATGAGGACCTCGAGCGGGCTGCGGCCAACCTCGGTATCAACTTGTCCCGCAACGAA         3420

SerAlaSerIleGluAspLeuAla***
TCGGCGTCCATAGAAGATCTGGCTTAG      3447
```

FIG. 12D

```
GlyAsnArgArgLeuArgThrValGlyGlyGluLeuIleGlnAsnGlnIleArgValGlyMet
GGCAACCGCCGCCTGCGTACGGTCGGGGAGCTGATCCAAAACCAGATCCGGGTCGGCATG          60

SerArgMetGluArgValValAlaArgMetThrThrGlnAspValGluAlaIleThr
TCGCGGATGGAGAGCGGGTGGTCCGGGAGCGGATGACCACCCAGGACGTGGAGGCGATCACA      120

ProGlnThrLeuIleAsnIleArgProValValAlaAlaAlaIleLysGluPhePheGlyThr
CCGCAGACGTTGATCAACATCCGGCCGGTGGTCGCCGCGGCGATCAAGGAGTTCTTCGGCACC    180

SerGlnLeuSerGlnPheMetAspGlnAsnAsnProLeuSerGlyLeuThrHisLysArg
AGCCAGCTGAGCCAATTCATGGACCAGAACAACCCGCTGTCGGGGTTGACGCACAAGCGC       240

ArgLeuSerAlaAlaLeuGlyProGlyGlyLysSerArgAraGluArgAlaGlyLeuGluAlaArg
CGACTGTCGGCGGCCCTGGGGCCCGGCGGCAAGTCTCGTGCACGTGAGCGTGCCGGGCTGGAGGTCCGC  300

AspValHisProSerHisTyrGlyArgMetCysProIleGluThrProGluGlyProAsn
GACGTGCACCCGTCGCACTACGGCCGGATGTGCCCGATCGAAACCCCTGAGGGCCCAAAC       360

IleGlyLeuIleGlySerLeuSerValTyrAlaArgValAsnProPheGlyPheIleGlu
ATCGGTCTGATCGGCTCGCTGTCGGTGTACGCGCGGGTCAACCCGTTCGGGTTCATCGAA       420

ThrProTyrArg
ACGCCGTACCGC       432
```

FIG. 13

```
atgcccgatcacagggcactgcggcagggaataattgcactacgccaacatgttaacaac                    20752

1
                          M  P  T  I  Q  Q  L  V  R  K  G
gaacacaatttacctgggagccggtatatgcccaccattcagcagctggtacgcaagggt                    20812
                                            c---------
                                        ML51

R  R  D  K  I  G  K  V  K  T  A  A  L  K  G  N  P  Q  R  R
cgtcgagacaagattggcaaggtcaagactgcggctctgaagggcaacccacagcgtcgc                    20872
-----g--------ca-t-----------c----------------g---g--------t
              S                                 S G  V  C  T  R  V  Y  T  S  P  K  K  P  N  S  A  L  R  K
ggtgtttgcacccgtgtgtacacttccaccccgaagaagccgaactcggcgcttcgcaag                    20932
----a---------c---------ca----t-------------------------g---
                        T V  A  R  V  K  L  T  S  Q  V  E  V  T  A  Y  I  P  G  E  G
gttgcccgcgtgaagctgacgagtcaggttgaggtcacagcgtacataccaggcgagggt                    20992
----------------t-------------c---------g--------t--c-------cg
                                                            A H  N  L  Q  E  H  S  M  V  L  V  R  G  G  R  V  K  D  L  P
cacaacctacaggaacactccatggtgttggtgcgtggtggccgggtgaaagatctgcct                    21052
--------g-----g-----g------c-------c--c-----------g--c------

G  V  R  Y  K  I  I  R  G  S  L  D  T  Q  G  V  K  N  R  K
ggtgtgcgttacaaaatcattcgcggttcgctcgacacccagggtgtcaagaaccggaag                    21112
--------c-----g
                                        ML52

Q  A  R  S  R  Y  G  A  K  K  E  K  S  *
caggctcgtagccgctatggagccaagaaggagaagagctga    21154
```

FIG. 14

```
                              10
    R  K  G     R  R  D  K    I  G  K     V  K  T     A  A  L  K
    CGCAAGGGTC  GTCGAGACAA  GATTGGCAAG  GTCAAGACCG  CGGCTCTGAA
        10          15          20          25

G  N  P    Q  R  R     G  V  C     T  R  V  Y    T  S  T
    GGGCAGCCCG  CAGCGTCGTG  GTGTATGCAC  CCGCGTGTAC  ACCACCACTC
        30          35          40

42
    P  K  K  P    N  S  A     L  R  K     V  A  R     V  K  L  T
    CGAAGAAGCC  GAACTCGGCG  CTTCGGAAGG  TTGCCCGCGT  GAAGTTGACG
        45          50          55

S  Q  V    E  V  T  A    Y  I  P    G  E  G    H  N  L  Q
    AGTCAGGTCG  AGGTCACGGC  GTACATTCCC  GGCGAGGCGC  ACAACCTGCA
        60          65          70          75

E  H  S    M  V  L      V  R  G    G  R  V    K  D  L  P
    GGAGCACTCG  ATGGTGCTGG  TGCGCGGCGG  CCGGGTGAAG  GACCTGCCTG
        80          85          90

G  V  R  Y  K
    GTGTGCGCTAC  AAG.
        95
```

FIG. 15

RAPID DETECTION OF ANTIBIOTIC RESISTANCE IN MYCOBACTERIUM TUBERCULOSIS

This application is a National stage application filed under 35 U.S.C. § 371 based on International Application PCT/EP/01063, filed Apr. 30, 1993, which is based upon U.S. application Ser. No. 07/929,206, filed Aug. 14, 1992, now U.S. Pat. No. 5,633,131, issued May 27, 1997, which is a continuation-in-part application of U.S. application Ser. No. 07/875,940, filed Apr. 30, 1992, now abandoned and French applications No. FR 93 04545, filed Apr. 16, 1993, and No. FR 92 11098, filed Sep. 17, 1992.

This invention relates to the rapid detection of strains of *Mycobacterium tuberculosis* that are resistant to antibiotics, particularly isoniazid, rifampicin and streptomycin. More particularly, this invention relates to a method of detecting antibiotic resistance in *Mycobacterium tuberculosis*, e.g. either as a result of mutations in the relevant genes or by nucleic acid hybridization. This invention also relates to a nucleic acid probe and a kit for carrying out the nucleic acid hybridization. The invention further relates to the chromosomal location of the katG gene (SEQ ID NO:45) and its nucleotide sequence.

BACKGROUND OF THE INVENTION

Despite more than a century of research since the discovery of *Mycobacterium tuberculosis*, the aetiological agent of tuberculosis, by Robert Koch, this disease remains one of the major causes of human morbidity and mortality. There are an estimated 3 million deaths annually attributable to tuberculosis (Snider, 1989), and although the majority of these are in developing countries, the disease is assuming renewed importance in the West due to the increasing number of homeless people and the impact of the AIDS epidemic (Chaisson et al., 1987; Snider and Roper, 1992).

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (Middlebrook, 1952; Youatt, 1969). Neither the precise target of the drug, nor its mode of action, are known, and INH treatment results in the perturbation of several metabolic pathways. There is substantial evidence indicating that INH may act as an antimetabolite of NAD and pyridoxal phosphate (Bekierkunst and Bricker, 1967; Sriprakash and Ramakrishnan, 1970; Winder and Collins, 1968, 1969, 1970), and other data indicating that the drug blocks the synthesis of the mycolic acids, which are responsible for the acid-fast character of mycobacterial cell walls (Winder and Collins 1970; Quemard et al., 1991). Shortly after its introduction, INH-resistant isolates of *Mycobacterium tuberculosis* emerged and, on characterization, were often found to have lost catalase-peroxidase activity and to show reduced virulence in guinea pigs (Middlebrook et al., 1954; Kubica et al., 1968; Sriprakash and Ramakrishnan, 1970).

Very recently, INH-resistance has acquired new significance owing to a tuberculosis epidemic in the USA due to multidrug resistant (MDR) variants of *M. tuberculosis* (CDC, 1990; 1991a, b) and the demonstration that such strains were responsible for extensive nosocomial infections of HIV-infected individuals and health care workers (Snider and Roper, 1992). In view of the gravity of this problem, there exists a need in the art to determine the relationship between INH-resistance and catalase-peroxidase production.

More particularly, there is a need in the art to understand the molecular mechanisms involved in drug sensitivity. In addition, there is a need in the art to develop a simple test permitting the rapid identification of INH-resistant strains. Further, there is a need in the art for reagents to carry out such a test.

Rifampicin too is a major antibiotic used for the treatment of infections by mycobacterium, particularly *Mycobacterium tuberculosis* and *Mycobacterium leprae*. Because some mycobacteria grow slowly, possible rapid and efficient tests for the testing of resistance to rifampicin or analogues thereof must be made available. Likewise the invention aims at a rapid detection of strands of *Mycobacterium tuberculosis* which are resistant to streptomycin. Because of the development of resistance to streptomycin, the latter antibiotic has been used together with other antibiotics, e.g. isoniazid. Thus adequat treatment of tuberculosis should be preceded by rapid and efficient detection of resistances to the three major antibiotics, isoniazid, rifampicin and streptomycin.

SUMMARY OF THE INVENTION

Accordingly, this invention aids in fulfilling these needs in the art by providing a process for detecting in vitro the presence of cells of a *Mycobacterium tuberculosis* resistant to isoniazid and other drugs, such as rifampicin or analogues thereof, and streptomycin.

By analogues of rifampicin, a particularly meant derivatives of 3-formyl-rifamycin, particularly as a result of substitution therein for the substituent present either in the naphtofuranonyl group or of the site chain at position 7 of the naphtofuranonyl group, or by the introduction or removal of a double band in the lateral chain.

In accordance with the invention, the detection of a resistance to isoniazid involves the detection of one or several ligations in the katG gene (SEQ ID NO:45) of *Mycobacterium tuberculosis*, particularly with respect to the nucleotide sequence of that same katG gene (SEQ ID NO:45) in *mycobacterium tuberculosis* that are not resistant to isoniazid.

Another process alternative for detecting in vitro the presence of nucleic acids of a *Mycobacterium tuberculosis* resistant to isoniazid, wherein the process comprises the steps of:

contacting said nucleic acids previously made accessible to a probe if required under conditions permitting hybridization;

detecting any probe that had hybridized to said nucleic acids;

wherein said probe comprises a nucleic acid sequence, which is 2.5 kb EcoRV-KpnI fragment of plasmid pYZ56 or of part thereof, and wherein said fragment contains a BamHI cleavage site, wherein said part is nonetheless sufficiently long to provide for the selectivity of the in vitro detection of a *Mycobacterium tuberculosis* resistant to isoniazid.

For instance, this process alternative comprises the steps of:

(A) depositing and fixing nucleic acids of the cells on a solid support, so as to make the nucleic acids accessible to a probe;

(B) contacting the fixed nucleic acids from step (A) with a probe under conditions permitting hybridization;

(C) washing the filter resulting from step (B), so as to eliminate any non-hybridized probe; and then (D) detecting any hybridized probe on the washed filter resulting from step (C).

The probe comprises a nucleic acid sequence which is present in a 2.5 kb EcoRV-KpnI fragment of plasmid pYZ56, wherein said fragment contains a BamHI cleavage site. This fragment has been found to be associated with intracellular DNA of isoniazid-sensitive *Mycobacterium tuberculosis* and is capable of distinguishing such antibiotic sensitive microorganisms from isoniazid-resistant *Mycobacterium tuberculosis*, which do not contain DNA that hybridizes with this fragment under the conditions described hereinafter.

This invention further provides nucleotide sequences, such as RNA and DNA, of isoniazid-resistant *Mycobacterium tuberculosis* encoding the region of the katG gene (SEQ ID NO:45) of *Mycobacterium tuberculosis* that imparts isoniazid sensitivity absent from isoniazid-resistant cells.

This invention also provides a probe consisting of a label, such as a radionucleotide, bonded to a nucleotide sequence of the invention.

In addition, this invention provides a hybrid duplex molecule consisting essentially of a nucleotide sequence of the invention hydrogen bonded to a nucleotide sequence of complementary base sequence, such as DNA or RNA.

Also, this invention provides a process for selecting a nucleotide sequence coding for a catalase-peroxidase gene of *Mycobacterium tuberculosis*, or for a portion of such a nucleotide sequence, from a group of nucleotide sequences, which comprises the step of determining which of the nucleotide sequences hybridizes to a nucleotide sequence of the invention. The nucleotide sequence can be a DNA sequence or an RNA sequence. The process can include the step of detecting a label on the nucleotide sequence.

Further, this invention provides a kit for the detection of *Mycobacterium tuberculosis* resistant to isoniazid. The kit comprises a container means containing a probe comprising a nucleic acid sequence, which is a 2.5 kb EcoRV-KpnI fragment of plasmid pYZ56, wherein the fragment contains a BamHI cleavage site. The kit also includes a container means containing a control preparation of nucleic acid.

The invention also covers compounds obtained as products of the action of the enzyme catalase, or a similar enzyme on isoniazid. The katG gene (SEQ ID NO:45) or a derivative of this gene which retains a similar activity can be used as a source of catalase protein. The new compounds are selected by reactivity on INH-resistant-mycobacterial strains by the antibiogram method such as described in H. David et al. 's "Methodes de laboratoire pour Mycobacteriologie clinique" edited by Pasteur Institute, ISBN N 0995-2454.

BRIEF DESCRIPTION OF THE DRAWINGS

This invention will be described in greater detail by reference to the drawings in which.

Transformation of BH1 with a mycobacterial shuttle plasmid, pBAK14, Zhang et al., 1991, containing the 4.5 kb insert from pYZ55 similarly conferred INH-susceptibility. MIC's are also shown for BH1 transformed with subfragments derived from pYZ55 and inserted into pBAK14 in one (+) or other (-) orientation. The katG gene (SEQ ID NO:45) and the ability to confer INH-susceptibility both mapped to a 2.9 kb EcoRV-KpnI fragment (pBAK-KE+).

Figure 1:
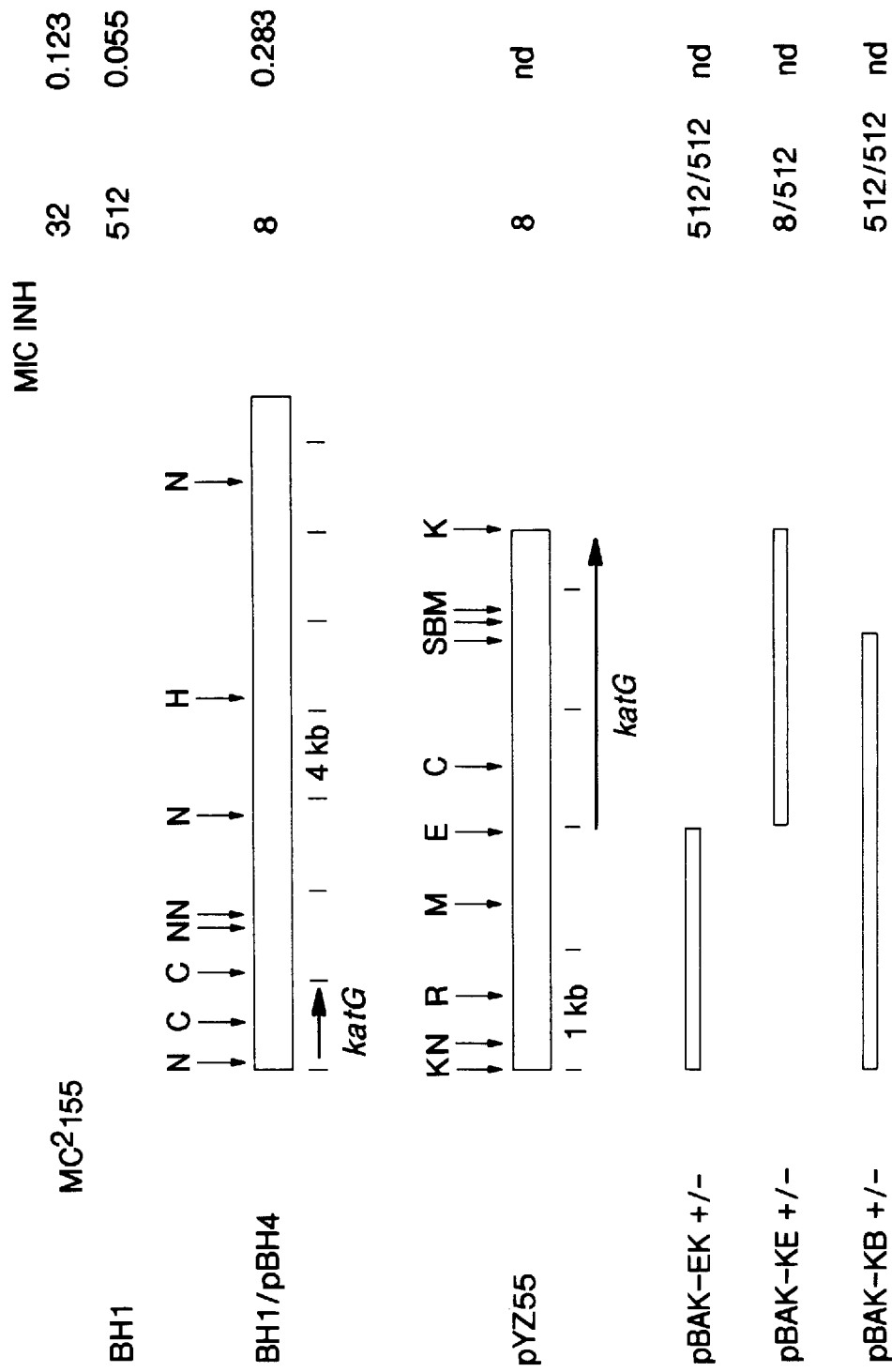
FIG. 1. shows the INH-resistant *M. smegmatis* strain, BH1 (Gayathri et al., 1975) (a derivative of strain MC$^2$-155) was transformed with a pool of *M. tuberculosis*-H37Rv shuttle cosmids (kindly provided by Dr. W. R. Jacobs, New York) and individual clones were scored for INH-susceptibility. Cosmid pBH4 consistently conferred drug susceptibility and the transformant overproduced catalase (assayed as in Heym, 1992). The restriction map of the DNA insert from pBH4 is shown along with that of the insert from pYZ55 —a plasmid containing katG of *M. tuberculosis* H37Rv, isolated on the basis of hybridization with an oligonucleotide probe (5'-TTCATCCGCATGGCCTGGCA-CGGCGCGGGCACCTACCGC-3') (SEQ ID NO:1) designed to match the amino acid sequence from a conserved region of *E. coli* hydroperoxidase I (HPI). Restriction sites for the following enzymes are indicated : B, BamHI;C, ClaI; E, EcoRV; H, HindIII, K, KpnI; M, SmaI; N, NotI; R, EcoRI; S, SacI.
Figure 2A:
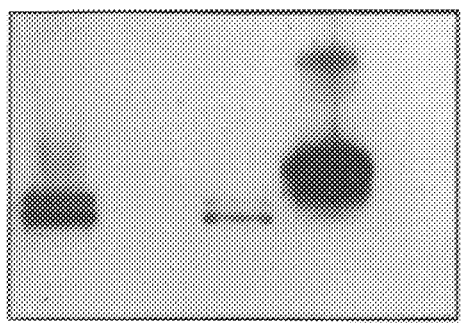
Figure 2B:
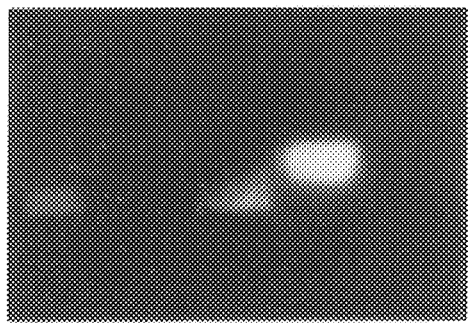

FIG. 2 shows extracts from *M. tuberculosis* H37Rv and from *E. coli* strains transformed with a variety of plasmid constructs that were prepared for activity gel analysis as described previously (Zhang et al., 1991). Non-denaturing gels containing 8% polyacrylamide were stained for catalase (panel A) and peroxidase (panel B) activities as described by Wayne and Diaz (Wayne et al., 1986). Lane 1, *M. tuberculosis* H37Rv; 2, *E. coli* UM2 (katE, katG; 3, *E. coli* UM2/pYZ55; 4, *E. coli* UM2/pYZ56 (the 2.9 kb EcoRV-KpnI fragment in pUC19, corresponding to pBAK-KE+in FIG. 1); 5, *E. coli* UM2/pYZ57 (pYZ55 with a BamHI-KpnI deletion, corresponding to pBAK-KB+ in FIG. 1). *M. tuberculosis* catalase and peroxidase activities migrated as two bands under these conditions (lane 1); the same pattern was seen for the recombinant enzyme expressed by pYZ55 (lane 3). pYZ56 (lane 4) expresses a protein of increased molecular weight due to a fusion between katG and lacZ' from the vector as shown in panel C. Panel C also shows partial sequence alignment with *E. coli* HPI (SEQ ID NOS:42–44).

Figure 3:
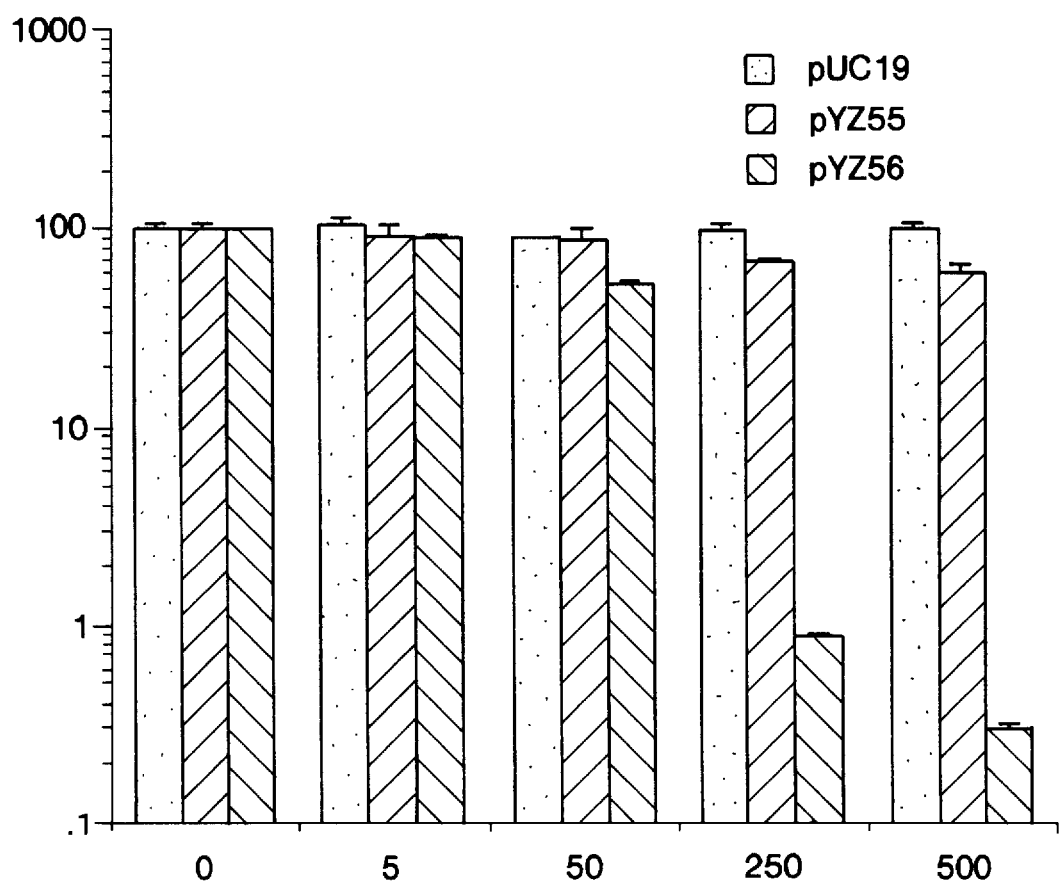

FIG. 3 shows an E coli strain with mutations in both katG and KatE (UM2 Mulvey et al., 1988) that was transformed with pUC19 vector alone, pYZ55 expressing *M. tuberculosis* katG and pYZ56 with high level expression of *M. tuberculosis* katG. Overnight cultures in Luria-Bertani broth supplemented with appropriate antibiotics were plated out in the presence of varying concentrations of INH and colony forming units were assessed. Results of a representative experiment are shown with error bars indicating the standard deviation observed in triplicate samples. Overexpression of *M. tuberculosis* katG similarly conferred susceptibility to high concentrations of INH in *E. coli* UM255 (katG, katE, Mulvey et al., 1988), but had no effect on catalase-positive strains such as *E. coli* TG1. In some experiments, high concentrations of INH had detectable inhibitory effect on growth of UM2 and UM255, alone, but in all experiments inhibition of pYZ56-transformants was at least 10–100 fold greater than that observed in the corresponding vector controls.

Figures 4A, 4B:
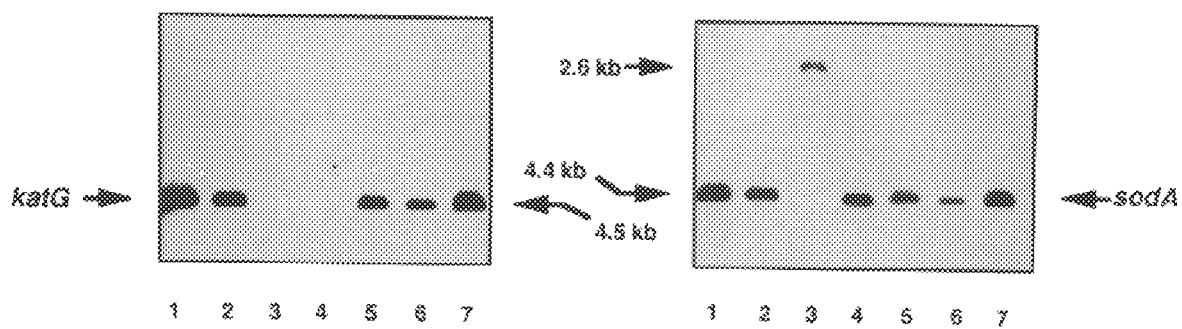

FIG. 4 shows Southern blots prepared using genomic DNA from different *N. tuberculosis* strains, digested with Kpn1, that were probed with (A) katG (the 4.5 kb Kpn1 fragment)(SEQ ID NO:45), and (B) the SOD gene (1.1 kb EcoR1-Kpn1 fragment, Zhang et al., 1991). Labelling of probes and processing of blots was performed as described previously (Eiglmeier et al., 1991; Maniatis et al., 1989). Lane 1, H37Rv; 2, strain 12 –MIC 1.6 μg/ml INH; 3, Bl453 -MIC>50 μg/ml INH (Jackett et al., 1978); 4, strain 24 –MIC>50 μg/m1 INH; 5, 79112 -INH-sensitive (Mitchison et al., 1963); 6, 12646 -INH-sensitive (Mitchison et al., 1963); 7, 79665 -INH-sensitive (Mitchinson et al., 1963). INH susceptibilities were confirmed by inoculation of Lowenstein-Jensen slopes containing differing concentrations of INH.

Figure 5:
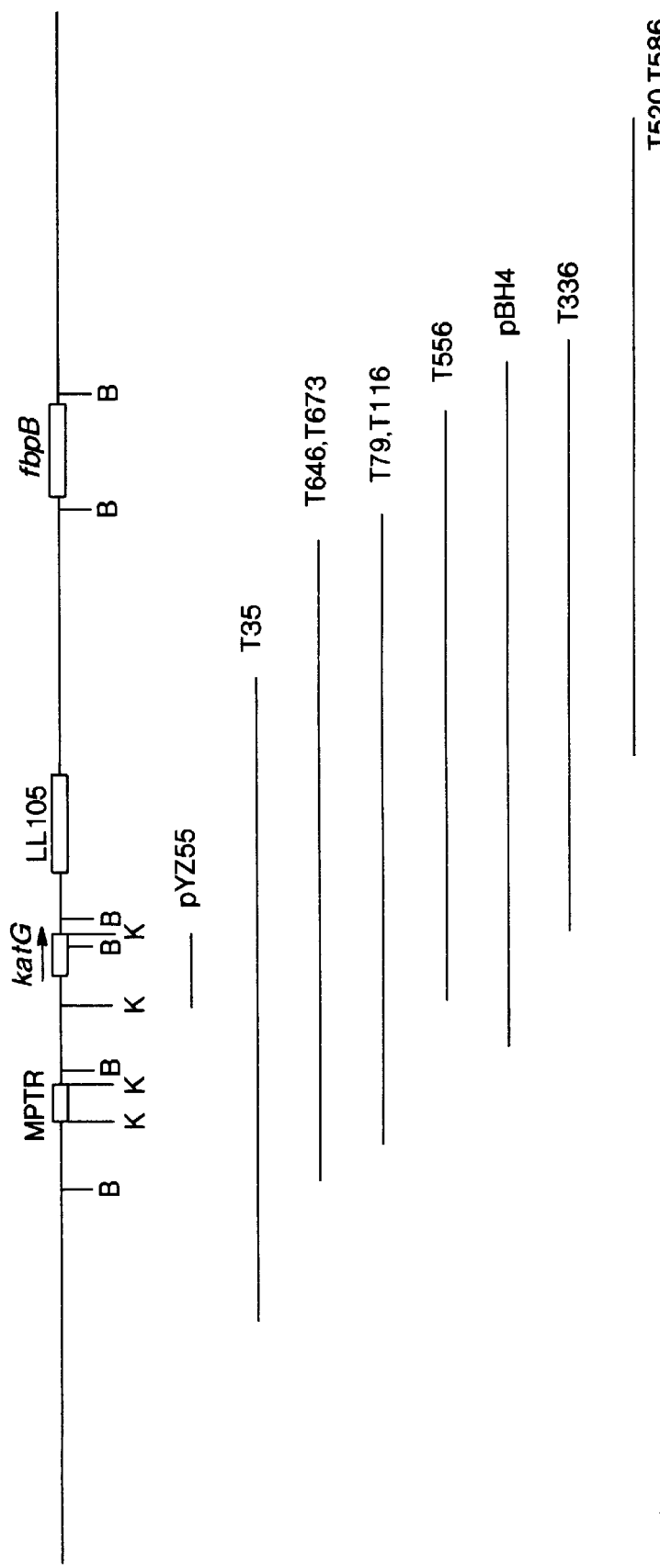

FIG. 5. Organization of the katG locus. The upper bar corresponds to a stretch of the M. tuberculosis chromosome spanning the katG region and the positions of individual cosmids used to construct the map are shown below together with the original shuttle cosmid pBH4 and pYZ55. The locations of some key restriction sites (B, BamHI; K, KpnI) are shown together with the approximate location of the known genetic markers: fbpB encoding the alpha or 85-B antigen (Matsuo et al., 1988); katG, catalase-peorxidase; LL105, an anonymous λgt11 clone kindly supplied by A Andersen; MPTR, major polymorphic tandem repeat (Hermans et al., 1992).

Figure 6B-1:
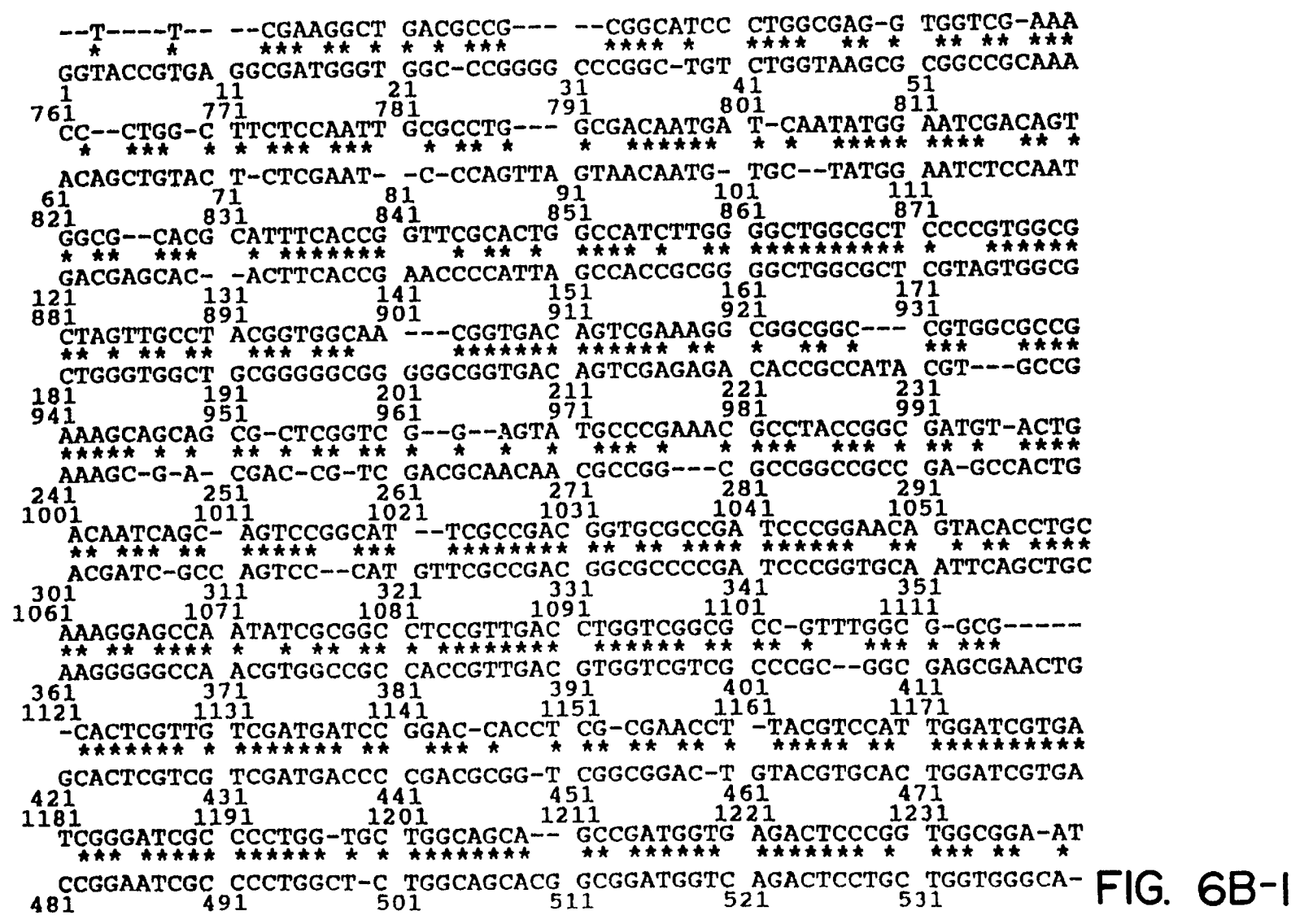

FIG. 6. A. Nucleotide sequence of the KpnI fragment bearing katG (SEQ ID NO:45). This sequence has been deposited in the EMBL data-library under accession number X68081. The deduced protein sequence is shown in the one letter code.
B. Alignment of the two copies of the 700 bp direct repeat with identities shown as * and —denoting pads introduced to optimize the alignment (SEQ ID NOS: 46–47). Numbering refers to the positions in FIG. 2A.

Figure 7A:
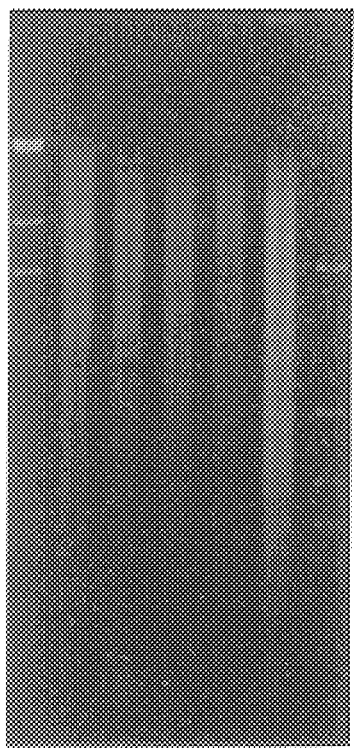
Figure 7B:
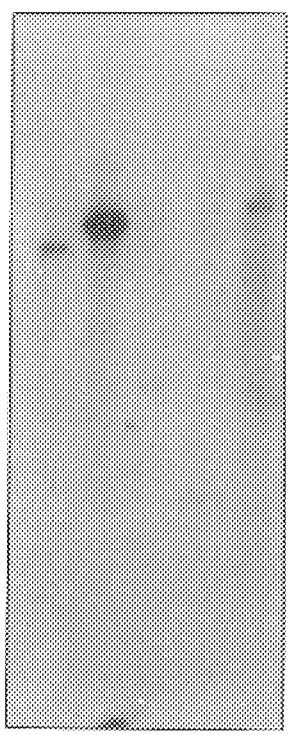

FIG. 7. Distribution of katG in mycobacteria. A. Samples of different bacterial DNAs (1.5 ug) were digested with RsrII, separated by agarose gel electrophoresis and stained with ethidium bromide; lanes 1 and 7, size markers; M. leprae; lane 3, M. tuberculosis H37Rv; lane 4, M. gordonae; lane 5, N. szulgai; lane 6, M. avium. B. Hybridization of the gel in A, after Southern blotting, with a katG specific probe.

FIGS. 8(1) and 8(2). Primary structure alignment of catalase-peroxidases (SEQ ID NOS:48–53). The sequences are from M. tuberculosis H37RV, mtkatg (SEQ ID NO:48); E. coli, eckatg (SEQ ID NO:49)(Triggs-Raine et al., 1988); S. typhimurium, stkatg (SEQ ID NO:50); B. stearothermophilus, bspera (SEQ ID NO:51)(Loprasert et al., 1988) and yeast cytochrome c peroxidase (SEQ ID NO:52) (ccp; Finzel et al., 1984). The alignment was generated using PILEUP and PRETTY (Devereux et al., 1984) and . denote gaps introduced to maximize the homology. Key residues from the active site and the peroxidase motifs (Welinder, 1991), discussed in the text, are indicated below the consensus.

Figure 9:
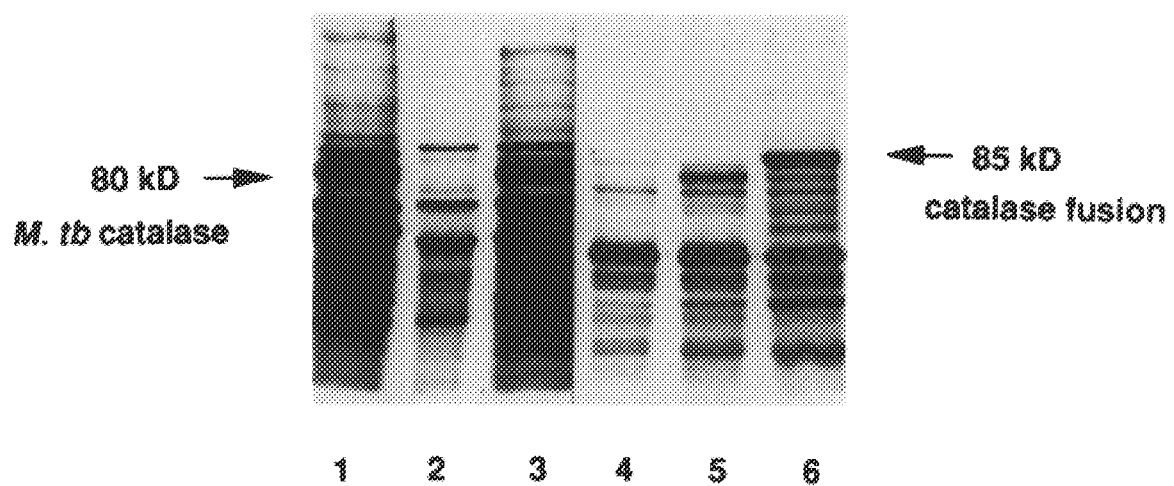
Figure 10:
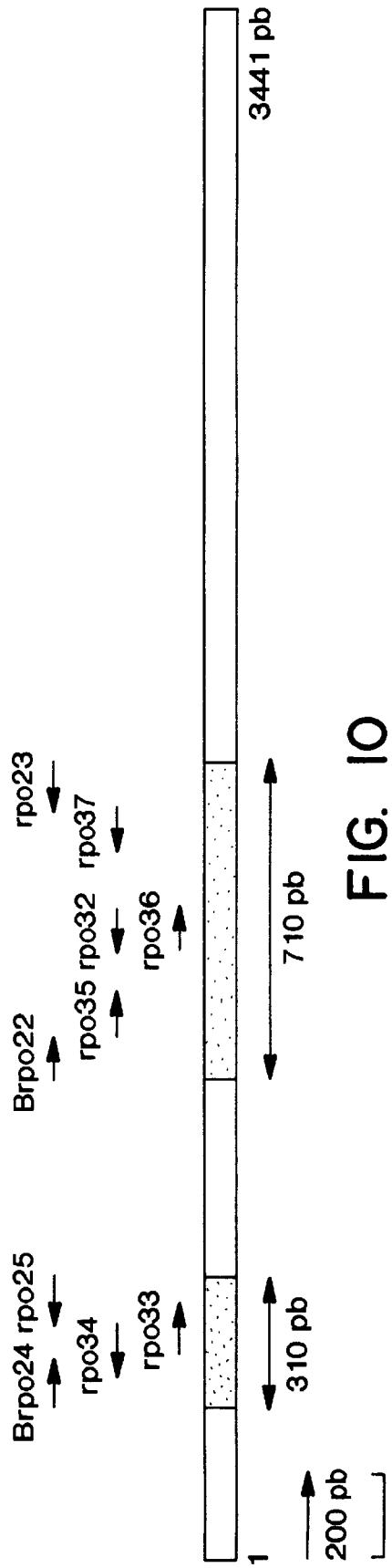

FIG. 9. Western blot analysis of M. tuberculosis KatG (SEQ ID NO:45) produced in different bacteria. Proteins were separated by SDS-polyacrylamide gel electrophoresis then subjected to immunoblotting, and detection with antiserum raised against BCG, as described in Zhang et al., 1991.
Lane 1, soluble extract of M. tuberculosis H37Rv; lane 2, M. smegmatis MC$^2$155 harboring the vector pBAK14; lane 3, M 155 harboring pBAK-KK (katG+); lane 4, E. coli UM2 (katE, katG), lane 5, UM2 harboring pYZ55 (katG$^+$); lane 6, UM2 harboring pYZ56 (lacZ'::katG), having regard to the drawings in which:

FIG. 10 represents diagrammatically the PCR strategy used for the study of different M. Leprae isolates, showing the coding sequence of rpoB sequence, whereby the sequenced regions are shown by hatched parts, and the position and reference of the amplification primers used being indicated on the upper line, whereas the sequencing primers are indicated bellow it;

FIG. 11 represents (A) the nucleotidic sequence of a short region of rpoB (SEQ ID NO:54) carrying the mutations that confer resistance to rifampicin with an indication of the changes of bases in the corresponding alleles and (B) a comparison between the amino acids sequences of the domain I of region II of the β-sub-unit of the RNA polymerase of E. coli (SEQ ID NO:55) and M. Leprae (SEQ ID NO:56), whereby the numbers of the residues and the differences in the mutated aminoacids have been indicated; the mutated amino acid residues associated with rifampicin resistance as well as the frequency of its occurrences have been represented too, FIG. 12 shows a complete sequence of the rpoB gene of M. Leprae (SEQ ID NO:56), FIG. 13 represents the sequence of part of the rpoB gene of M. tuberculosis (SEQ ID NOS:59–60), FIG. 14 represents the sequence of a part of the rpsL gene of M. tuberculosis (SEQ ID NOS:63–64); both the sequence of the full rpsL gene of M. Leprae and that of its expression product (SEQ ID NOS:61–62), that is the S12 protein (whose starting aminoacid is noted by 1) are indicated. The positions of the ML51 (SEQ ID NO:40) and ML52 (SEQ ID NO:41) primers, as well as of the sequences of part of the rpsL gene of M. tuberculosis are provided below those of M. Leprae. Only those positions which are different and the corresponding amino acid changes are indicated.

FIG. 15 represents the wild DNA sequence of the rpsL gene (SEQ ID NO:65) fragment coding for the S12 protein of the small ribosome sub-unit that is responsible for the resistance to streptomycin, as well as the corresponding aminoacid sequence of the S12 protein (SEQ ID NO:66).

DETAILED DESCRIPTION OF PREFERRED EMBODIMENT

The recent emergence of large numbers of strains of M. tuberculosis showing multidrug resistance in the United States is a most alarming development given the extreme contagiousness of this organism. This danger has been strikingly illustrated by several small tuberculosis epidemics in which a single patient infected with MDR M. tuberculosis has infected both HIV-positive individuals, prison guards and healthy nursing staff (CDC 1990, 1991; Daley et al., 1992; Snider and Roper, 1992). Given the gravity of the current worldwide HIV epidemic, it is conceivable that if AIDS patients in the West, like those in Africa, were to be infected with MDR M. tuberculosis strains (rather than members of the M. avium/M. intracellulare complex) widespread dissemination of the disease would result.

Isoniazid (INH) is a bactericidal drug which is particularly potent against the tuberculosis group of mycobacteria—Mycobacterium tuberculosis, M. bovis, and M. africanum—and, in consequence, it has been particularly effective in the treatment of tuberculosis. Standard antituberculosis regimens generally include INH and rifampicin, often in combination with the weaker drugs, pyrazinamide, ethambutol or streptomycin. Besides its use in therapy INH is also given to close contacts of patients as a prophylactic measure.

INH-resistant mutants of M. tuberculosis, the agent of the human disease, show two levels of resistance: low (1 to 10 μg/ml) and high (10 to 100 μg/ml). INH-resistance is often associated with loss of catalase activity and virulence. Recently, owing to the AIDS epidemic, increased homelessness and declining social conditions, tuberculosis has reemerged as a major public health problem in developed countries, particularly the USA. An alarming feature of the disease today is the emergence of multiple drug-resistant organisms and rapid nosocomial transmission to health care workers and HIV-infected patients. This has prompted CDC to propose new recommendations for the treatment of multiple resistant strains (at least INH and rifampicin) and the prevention of transmission. To obtain fresh insight into the problem of INH-resistance and to develop a rapid diagnostic test the following study was performed.

Clearly, it is essential to understand the mechanisms of resistance to INH and rifampicin, the main anti-tuberculosis agents, as this will allow novel chemotherapeutic strategies to be developed and facilitate the design of new compounds active against MDR strains.

This invention demonstrates that it is the catalase-peroxidase enzyme, HPI, which is the INH target, and it is suggested that this enzyme alone mediates toxicity. Compelling evidence of this conclusion was obtained by expression of the M. tuberculosis katG gene (SEQ ID NO:45) in a catalase-negative mutant of E. coli as this resulted in this bacterium becoming sensitive to INH. Moreover, the isolation of the M. tuberculosis INH-sensitivity gene, katG (SEQ ID NO:45), is important as it will facilitate the rapid detection of INH-resistant strains by means of hybridization and PCR-based approaches. The high frequency of deletions in clinical strains, as shown here, should simplify this procedure.

Identification of an *M. tuberculosis* gene involved in INH-sensitivity

A heterologous approach was employed to isolate *M. tuberculosis* gene(s) involved in INH-sensitivity. BH1 is a spontaneous mutant of the easily transformable *M. smegatis* strain $MC^2155$ (Snapper et al., 1990), that is resistant to 512 $\mu$g/ml of the INH and lacks catalase-peroxidase activity (Heym et al., 1992). As there is a strict correlation between INH-sensitivity and these enzyme activities, transformation of BH1 with a plasmid carrying the appropriate gene from *M. tuberculosis* should lead to their restoration and concomitant INH-sensitivity.

Consequently, DNA was prepared from a pool of *M. tuberculosis* shuttle cosmids in *Escherichia coli* and introduced into BN1 by electro-transformation. Over 1000 kanamycin-resistant transformants were then scored for INH-sensitivity, and four clones that failed to grow on medium containing 32 g/ml of INH, the MIC from wild type strain $M^2155$, were obtained.

After re-transformation of BH1, only one of these, pBN4, consistently conferred the INH-sensitive phenotype. Restriction digests with BamHI, KpnI, NotI, ClaI and HindIII showed the *M. tuberculosis* chromosomal DNA carried by pBH4 to be about 30 kb in size. A map produced with the last three enzymes is presented in FIG. 1.

When pBN4 was used as a hybridization probe to detect homologous clones in the library, a further eight shuttle cosmids were isolated. On transformation into BH1, five of these (T35, T646, T673, T79, T556) restored INH-sensitivity, and showed similar restriction profiles to pBN4. In particular, a KpnI fragment of 4.5 kb was present in all cases.

Attempts to subclone individual BamHI fragments did not give rise to transformants capable of complementing the lesion in BH1 suggesting that a BamHI site might be located in the gene of interest. In contrast, pBH5, a derivative of pBH4, was constructed by deletion of EcoRI fragments and this showed that a 7 kb segment was not required for restoration of INH-sensitivity.

Transformants harboring shuttle cosmids that complemented the INH-resistant mutation of BH1 were examined carefully and the MICs for several antibiotics were established. In all cases, the MIC for INH had been reduced from 512 to 8 $\mu$g/ml, a value lower than that of the sensitive strain $MC^2155$ (32 $\mu$g/ml). This hypersensitive phenotype suggested that the recombinant clones might be overproducing an enzyme capable of enhancing INH-toxicity. Enzymological studies showed that these transformants all produced about 2-fold more peroxidase and catalase than the wild type strain M2155, which is INH-sensitive.

In addition to INH, many MDR-strains of *M. tuberculosis* are no longer sensitive to rifampicin, streptomycin, ethambutol and pyrazinamide. To examine the possibility that there might be a relationship between resistance to INH and these compounds, the MICs of several drugs for various *M. smegmatis* strains and their pBH4 transformants were determined, but no differences were found.

Cloning the *M. tuberculosis* catalase gene

A 45-mer oligonucleotide probe was designed based on the primary sequences of highly conserved regions in the catalase-peroxidase enzymes, HPI, of *E. coli* (Triggs-Raine et al., 1989), and *Bacillus stearothermophilus* (Loprasert et al., 1988). When genomic blots of *M. tuberculosis* DNA were probed with this oligonucleotide, specific bands were detected in most cases. As KpnI generated a unique fragment of 4.5 kb that hybridized strongly, this enzyme was used to produce a size selected library in pUC19.

Upon screening with the oligonucleotide probe, an appropriate clone, pYZ55, was obtained. A restriction map of the insert DNA is presented in FIG. 1 where it can be seen that this corresponds exactly to part of pBH4. Independent confirmation was also obtained by cross-hybridization.

By means of various subcloning experiments the smallest fragment expressing *M. tuberculosis* catalase-peroxidase activity in *E. coli* was found to be a 2.5 kb EcoRV-KpnI fragment which, as expected, contained a cleavage site for BamHI. Partial DNA sequence analysis showed that the katG gene carried by pYZ56 encodes a catalase-peroxidase enzyme that is highly homologous to the HPI enzymes of *E. coli* and *M. stearothermophilus*:

| | |
|---|---|
| *M. tuberculosis* | APLNSWPDNASLDKARRLLWPSKKKYGKKLSWADLIV (SEQ ID NO: 2) |
| *E. coli* | *********V***********I*Q***Q*I*****FI (SEQ ID NO: 3) |
| *B. stearothermophilus* | **********N******C*GR**RNT*T*-*LGPICS (SEQ ID NO: 4) |

(FIG. 2; Triggs-Raine et al., 1988); (Loprasert et al., 1988). Identical residues are indicated by *. HPI activity was detected in both *E. coli* and *M. smegmatis* by staining (see below).

Catalase-peroxidase involvement in INH-sensitivity

Having cloned the *M. tuberculosis* katG gene, it was of immediate interest to investigate the genetic basis of the association between catalase-negativity and isoniazid resistance. A series of constructs was established in the shuttle vector pBAK14 and used to transform the INH-resistant *M. smegmatis* mutant BH1. Only those plasmids carrying a complete katG gene (SEQ ID NO:45) produced HPI and restored INH-sensitivity. The smallest of these, pBAK14, carried a 2.5 kb EcoRV-KpnI fragment thus demonstrating that the 2 kb region upstream of katG was not involved, and that catalase-peroxidase activity alone was sufficient to render mycobacteria susceptible to INH.

Cell-free extracts were separated by non-denaturating polyacrylamide gel electrophoresis and stained for peroxidase and catalase activity. Under these conditions, the *M. tuberculosis* enzyme gave two bands of peroxidase activity (lane 1) which comigrated with catalase activity (Heym et al., 1992).

When introduced into *E. coli*, the katG gene (SEQ ID NO:45) directed the synthesis of the same proteins, whereas pYZ56 produced proteins slightly larger in size. This is due to the construction of an in-frame lacZ::katG gene fusion. Activity stains were also performed with cell extracts of *M. smegmatis*. The presence of the katG gene (SEQ ID NO:45) from the *M. tuberculosis* in BH1 led to the production of catalase-peroxidase enzyme, which displayed the same electrophoretic mobility as the enzyme made in *M. tuberculosis*, or in *E. coli*, and the native HPI of *M. smegmatis*.

Basis of INH-resistance in *M. tuberculosis*

It has been known for many years that a subset of INH-resistant strains, particularly those resistant to the highest drug concentrations, are of lower virulence in the guinea pig and devoid of catalase activity. Genomic DNA was prepared from several clinical isolates of *M. tuberculosis* and analyzed by Southern blotting using the 4.5 kb KpnI fragment (SEQ ID NO:45) as a probe. In two highly resistant strains, B1453 and 24, the catalase gene has been deleted from the chromosome whereas in others (FIG. 3), such as strain 12, showing low level resistance it is still present but not expressed. Additional studies showed that the region immediately prior to katG (SEQ ID NO:45) was highly prone to rearrangements.

*M. tuberculosis* HPI renders *E. coli* sensitive to INH

To determine whether the HPI enzyme of *M. tuberculosis* could confer INH sensitivity on *E. coli*, a series of catalase mutants was transformed with pYZ56 and the MICs determined. Wild type strains were not susceptible to INH, but mutants lacking both endogenous catalase activities, but harboring pYZ56, showed growth inhibition when high levels of INH (500 μg/ml) were present, whereas untransformed strains were insensitive.

For purposes of this invention, a plasmid containing the restriction endonuclease map shown in FIG. 1 was deposited in strain with the National Collection of Cultures of Microorganisms (C.N.C.M.) of the Institut Pasteur, in Paris, France on May 18, 1992, under culture collection accession No. I-1209. This plasmid contains the nucleic acid sequence of the invention, namely, the 4.5 kb KpnI—KpnI fragment (SEQ ID NO:45) of plasmid pYZ56 having the BamHI cleavage site in the fragment.

In general, the invention features a method of detecting the presence of isoniazid-resistant *Mycobacterium tuberculosis* in a sample including providing at least one DNA or RNA probe capable of selectively hybridizing to isoniazid-sensitive *Mycobacterium tuberculosis* DNA to form detectable complexes. Detection is carried out with a sample under conditions which allow the probe to hybridize to isoniazid-sensitive *Mycobacterium tuberculosis* DNA present in the sample to form hybrid complexes and detecting the hybrid complexes as an indication of the presence of isoniazid-sensitive *Mycobacterium tuberculosis* in the sample. (The term "selectively hybridizing"), as used herein, refers to a DNA or RNA probe which hybridizes only to isoniazid-sensitive *Mycobacterium tuberculosis* and not to isoniazid-insensitive *Mycobacterium tuberculosis*.) The sample can be comprised of the *Mycobacterium tuberculosis* cells or a portion of the cells or cell contents enriched in *Mycobacterium tuberculosis* nucleic acids, especially DNA. Hybridization can be carried out using conventional hybridization reagents. The particular hybridization conditions have not been found to be critical to the invention.

More particularly, DNA sequences from *Mycobacterium tuberculosis* can be analyzed by Southern blotting and hybridization. The techniques used for the present invention are described in Maniatis et al. (1989). DNA fragments can be separated on agarose gels and denatured in situ. The fragments can then be transferred from the gel to a water insoluble solid, porous support, such as a nitrocellulose filter, a nylon membrane, or an activated cellulose paper, where they are immobilized for example, the Hybond® membrane commercialized by Amersham can be used. After prehybridization to reduce non-specific hybridization with the probe, the solid support is hybridized to the nucleic acid probe of the invention. The solid support is washed to remove unbound and weakly binding probe, and the resulting hybrid duplex molecule is examined. A convenient alternative approach is to hybridize oligonucleotides to the DNA denatured in the gel.

The amount of labeled probe which is present in the hybridization solution will vary widely, depending upon the nature of the label, the amount of the labeled probe which can reasonably bind to the filter, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementary that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

Unlike Southern hybridization where DNA fragments are transferred from an agarose gel to a solid support, the method of the invention can also be carried out by oligonucleotide hybridization in dried agarose gels. In this procedure, the agarose gel is dried and hybridization is carried out in situ using an oligonucleotide probe of the invention. This procedure is preferred where speed of detection and sensitivity may be desirable. The procedure can be carried out on agarose gels containing genomic or cloned DNA of *Mycobacterium tuberculosis*.

In addition, the method of this invention can be carried out by transfer of *Mycobacterium tuberculosis* DNA from polyacrylamide gels to nylon filters by electroblotting. Electroblotting may be desirable where time is of the essence, because electroblotting is typically faster than capillary blotting developed to transfer DNA from agarose gels. This method can be carried out in conjunction with UV-crosslinking. The polyacrylamide gel containing the samples to be tested is placed in contact with an appropriately prepared nylon filter. These are then sandwiched into an electroblotting apparatus and the DNA is transferred from the gel onto the filter using electric current. After a buffer rinse, the filter is ready to be prehybridized and hybridized or UV-crosslinked.

The method of the invention can be carried out using the nucleic acid probe of the invention for detecting *Mycobacterium tuberculosis* resistant to isoniazid. The probe can be detected using conventional techniques.

The method of the invention can also detect point mutations in the KatG gene (SEQ ID NO:45), as well as a partial deletion of that gene.

The nucleotides of the invention can be used as probes for the detection of a nucleotide sequence in a biological sample of *M. tuberculosis*. The polynucleotide probe can be labeled with an atom or inorganic radical, most commonly using a radionuclide, but also perhaps with a heavy metal. labels include $^{32}$P, $^{3}$H, $^{14}$C, or the like. Any radioactive label can be employed, which provides for an adequate signal and has sufficient half-life. Other labels include ligands that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

In preferred embodiments of the invention, the probe is labeled with a radioactive isotope, e.g., $^{32}$P or $^{125}$I, which can be incorporated into the probe, e.g., by nick-translation.

In other preferred embodiments, the probe is labeled with biotin, which reacts with avidin to which is bonded a chemical entity which, when the avidin is bonded to the biotin, renders the hybrid DNA complex capable of being detected, e.g., a fluorophore, which renders the hybrid DNA complex detectable fluorometrically; an electron-dense compound capable of rendering the hybrid DNA complexes detectable by an electron microscope; an antibody capable of rendering the hybrid DNA complexes immunologically detectable; or one of a catalyst/substrate pair capable of rendering the hybrid DNA complexes enzymatically detectable. Prior to contacting the bacteria with the probe, the *M. tuberculosis* bacteria can be lysed to release their DNA, which is then denatured and immobilized on an appropriate solid, DNA-binding support, such as a nitrocellulose membrane.

Another detection method, which does not require the labeling of the probe, is the so-called sandwich hybridization technique. In this assay, an unlabeled probe, contained in a single-stranded vector, hybridizes to isoniazid-sensitive *Mycobacterium tuberculosis* DNA, and a labeled, single-stranded vector, not containing the probe, hybridizes to the probe-containing vector, labeling the whole hybrid complex.

The sequences of the invention were derived by dideoxynucleotide sequencing. The base sequences of the nucleotides are written in the 5'→3' direction. Each of the letters shown is a conventional designation for the following nucleotides:

A Adenine
G Guanine
T Thymine
C Cytosine.

The nucleotides of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

The nucleotides of the invention are in a purified form. For instance, the nucleotides are free of human blood-derived proteins, human serum proteins, viral proteins, nucleotide sequences encoding these proteins, human tissue, and human tissue components. In addition, it is preferred that the nucleotides are free of other nucleic acids, extraneous proteins and lipids, and adventitious microorganisms, such as bacteria and viruses.

This invention of course includes variants of the nucleotide sequences of the invention or serotypic variants of the probes of the invention exhibiting the same selective hybridization properties as the probes identical herein.

The nucleotide sequences of the present invention can be employed in a DNA amplification process known as the polymerase chain reaction (PCR) . See, e.g. Kwok et al. (1987). PCR is advantageous because this technique is rapid.

DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the PBMC DNA. The PCR reaction mixture can contain the PBMC DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the PBMC DNA at an elevated temperature, cooling of the reaction mixture, and polymerization with the DNA polymerase.

Amplified sequences can be detected by the use of a technique termed oligomer restriction (OR). Single-strand conformation polymorphism (SSCP) analysis can be used to detect DNA polymorphisms and point mutations in a variety of positions in DNA fragments. See, Saiki et al. (1985); Orita et al. (1989). For example, after amplification, a portion of the PCR reaction mixture can be separated and subjected to hybridization with an end-labeled nucleotide probe, such as a $^{32}$p labelled adenosine triphosphate end-labeled probe. In OR, an end-labeled oligonucleotide probe hybridizes in solution to a region of the amplified sequence and, in the process, reconstitutes a specific endonuclease site. Thus, hybridization of the labeled probe with the amplified katG sequence (SEQ ID NO:45) yields a double-stranded DNA form that is sensitive to selective restriction enzyme digestion. After restriction with an endonuclease, the resulting samples can be analyzed on a polyacrylamide gel, and autoradiograms of the portion of the gel with the diagnostic labeled fragment can be obtained. The appearance of a diagnostic fragment (e.g., 10–15 bases in length) in the autoradiogram indicates the presence of katG sequences (SEQ ID NO:45) in the PBMCs.

Since it may be possible to increase the sensitivity of detection by using RNA instead of chromosomal DNA as the original template, this invention contemplates using RNA sequences that are complementary to the DNA sequences described herein. The RNA can be converted to complementary DNA with reverse transcriptase and then subjected to DNA amplification.

EXPERIMENTAL PROCEDURES

Bacterial strains and plasmids

Table 1 outlines the properties of the bacterial strains and plasmids used in this invention.

TABLE 1

Bacterial Strains and Plasmids

| Strains/plasmids | Characteristics |
|---|---|
| E. coli NM554 | |
| E. coli TG1 | supE hsd5 thi delta (lac-proAB) [traD36 proAB + lacI$^g$ lacZ delta M15] |
| E. coli UM2 | KatE |
| E. coli UM255 | KatE |
| M. tuberculosis H37Rv | Virulent strain originally isolated from tuberculosis patient |
| M. tuberculosis 12 | Clinical isolate resistant to low levels of INH (1–2 μg/ml) |
| M. tuberculosis B1453 | Clinical isolate resistant to high levels of INH (>50 μg/ml) |
| M. tuberculosis 24 | Clinical isolate resistant to high levels of INH (>50 μg/ml) |
| M. tuberculosis 79112 | Clinical isolate sensitive to INH |
| M. tuberculosis 12646 | Clinical isolate sensitive to INH |
| M. tuberculosis 79665 | Clinical isolate sensitive to INH |
| M. smegmatis MC$^2$155 | MC26 het |
| M. smegmatis BH1 | MC2155 het katG |
| Plasmids | |
| pBH4 | Shuttle cosmid, katG+, based on pYUB18 |
| pBH5 | Deleted version of pBN4, katG+, (7 kb-EcoRI) |
| pYZ55 | pUC19 derivative with 4.5 kb KpnI fragment, kat+ |
| pYZ56 | pUC19 derivative with 2.5 kb EcoRV-KpnI fragment (kat+) |
| pYZ57 | pUC19 derivative with 3.1 kb KpnI-BamHI fragment, kat– |
| pBAK14 | Mycobacterial shuttle vector (Zhang et al., 1991) |
| pBAK15 | Mycobacterial shuttle vector carrying 4.5 kb KpnI fragment (kat+) |
| pBAK16 | Mycobacterial shuttle-vector carrying 2.5 kb EcoRV-KpnI fragment (kat*) |
| pBAK17 | Mycobacterial shuttle vector carrying 3.1 kb KpnI-BamHI fragment (kat–) |

The M. tuberculosis H37 RV genomic library was constructed in the shuttle cosmid pYUB18 (Snapper et al., 1988) and kindly supplied by Dr. W. R. Jacobs. Other shuttle vectors employed were pYUB12 (Snapper et al., 1988) and pBAK14 (Zhang et al., 1991).

Microbiological techniques and enzymology

Details of antibiotics used, growth conditions, enzymology and MIC determinations can be found in Heym et al., (1992).

Nucleic acid techniques

Standard protocols were used for subcloning, Southern blotting, DNA sequencing, oligonucleotide biosynthesis, etc. (Maniatis et al., 1989; Eiglmeier et al., 1991).

Activity staining

The preparation of cell-free extracts of E. coli and mycobacteria has been described (Heym et al., 1992; Zhang et al., 1991). Native protein samples were separated by polyacrylamide gel electrophoresis as described by Laemmli (1970) except that SDS was omitted from all buffers, samples were not boiled and betamercaptoethanol was not included in the sample buffer. After electrophoresis of 50 –100 μg protein samples on 7.5% polyacrylamide gels, catalase activity was detected by soaking the gel in 3 mM $H_2O_2$ for 20 minutes with gentle shaking. An equal volume of 2% ferric chloride and 2% potassium ferricyanide was added and clear bands of catalase activity revealed by illumination with light. Peroxidase activity was detected as brown bands after soaking gels in a solution containing 0.2–0.5 mg/ml diaminobenzidine and 1.5 mM $H_2O_2$ for 30–120 minutes.

To generate a highly toxic compound it seems most likely that the M. tuberculosis HPI enzyme peroxidatively activates INH (Youatt, 1969; Gayathri-Devi et al., 1975). Now that the katG gene (SEQ ID NO:45) has been isolated and characterized, it should be possible to make new derivatives of INH, which can be activated in a similar manner.

Example 1

Point Mutations in the katG Gene Associated with the Isoniazid-Resistance of M. Tuberculosis It has been shown in a recent study that the catalase-peroxidase of Mycobacterium tuberculosis, encoded by the katG gene (SEQ ID NO:45), is involved in mediating the toxicity of the potent anti-tuberculosis drug isoniazid or INH. Mutants resistant to clinical levels of INH show reduced catalase-peroxidase activity and, in some cases, this results from the deletion of the katG gene (SEQ ID NO:45) from the chromosome. Transformation of INH-resistant strains of Mycobacterium smegmatis and M. tuberculosis with the cloned katG gene leads to restoration of drug-sensitivity. Expression of katG (SEQ ID NO:45) in some strains of Escherichia coli renders this naturally resistant organism susceptible to high concentrations of INH.

As some INH-resistant clinical isolates of M. tuberculosis have retained an intact katG gene (SEQ ID NO:45), the molecular basis of their resistance was investigated. This study was facilitated by the availability of the nucleotide sequence of a 4.7 kb KpnI fragment from the katG region of the chromosome as this allowed primers suitable for PCR analysis to be designed. Eleven pairs of oligonucleotide primers were synthesized (SEQ ID NOS:5–26) (see Table 2) and used to generate PCR-products, of around 280 bp, that covered the complete katG gene (SEQ ID NO:45) and some of the flanking sequences. In control experiments all experiments all eleven primer pairs generated PCR products of the expected size, highly suitable for SSCP-analysis, so a panel of 36 INH-resistant strains of M. tuberculosis, of Dutch or French origin, was examined. Many of these strains are multidrug resistant and were isolated from patients who were HIV-seropositive.

TABLE 2

Sequences of primer pairs used for PCR-SSCP analysis of the katG gene of M. tuberculosis

| | | 5' | 3' | Length | G|C(%) | Tm | Production |
|---|---|---|---|---|---|---|---|
| Primer Pair # 1 | | | | | | | |
| OLIGO1: | GCGGGGTTATCGCCGATG (SEQ ID NO:5) | 1765 | 1782 | 18 | 66 | 61.8 | 288 |
| OLIGO2: | GCCCTCGACGGGGTATTTC (SEQ ID NO:6) | 2052 | 2034 | 19 | 63 | 61.9 | |

TABLE 2-continued

Sequences of primer pairs used for PCR-SSCP analysis of the katG gene of M. tuberculosis

|  |  | 5' | 3' | Length | GIC(%) | Tm | Production |
|---|---|---|---|---|---|---|---|
| Primer Pair # 2 | | | | | | | |
| OLIGO1: | AACGGCTGTCCCGTCGTG (SEQ ID NO:7) | 2008 | 2025 | 18 | 66 | 61.9 | 300 |
| OLIGO2: | GTCGTGGATGCGGTAGGTG (SEQ ID NO:8) | 2307 | 2289 | 19 | 63 | 61.9 | |
| Primer Pair # 3 | | | | | | | |
| OLIGO1: | TCGACTTGACGCCCTGACG (SEQ ID NO:9) | 2169 | 2187 | 19 | 63 | 61.9 | 280 |
| OLIGO2: | CAGGTCCGCCCATGACAG (SEQ ID NO:10) | 2448 | 2431 | 18 | 66 | 61.9 | |
| Primer Pair # 4 | | | | | | | |
| OLIGO1: | CCACAACGCCAGCTTCGAC (SEQ ID NO:11) | 2364 | 2382 | 19 | 53 | 61.9 | 284 |
| OLIGO2: | GGTTCACGTAGATCAGCCCC (SEQ ID NO:12) | 2647 | 2628 | 20 | 50 | 61.9 | |
| Primer Pair # 5 | | | | | | | |
| OLIGO1: | GCAGATGGGGCTGATCTACG (SEQ ID NO:13) | 2622 | 2641 | 20 | 60 | 51.9 | 288 |
| OLIGO2: | ACCTCGATGCCGCTGGTG (SEQ ID NO:14) | 2909 | 2892 | 18 | 66 | 51.9 | |
| Primer Pair # 6 | | | | | | | |
| OLIGO1: | GCTGGAGCAGATGGGCTTG (SEQ ID NO:15) | 2829 | 2847 | 19 | 63 | 61.9 | 286 |
| OLIGO2: | ATCCACCCGCAGCGAGAG (SEQ ID NO:16) | 3114 | 3097 | 18 | 66 | 61.9 | |
| Primer Pair # 7 | | | | | | | |
| OLIGO1: | GCCACTGACCTCTCGCTG (SEQ ID NO:17) | 3088 | 3105 | 18 | 66 | 61.9 | 297 |
| OLIGO2: | CGCCCATGCGGTCGAAAC (SEQ ID NO:18) | 3384 | 3367 | 18 | 66 | 61.9 | |
| Primer Pair # 8 | | | | | | | |
| OLIGO1: | GCGAAGCAGATTGCCAGCC (SEQ ID NO:19) | 3304 | 3322 | 19 | 63 | 61.9 | 285 |
| OLIGO2: | ACAGCCACCGAGCACGAC (SEQ ID NO:20) | 3588 | 3571 | 18 | 66 | 61.9 | |
| Primer Pair # 9 | | | | | | | |
| OLIGO1: | CAAACTGTCCTTCGCCGACC (SEQ ID NO:21) | 3549 | 3568 | 20 | 60 | 61.9 | 281 |
| OLIGO2: | CACCTACCAGCACCGTCATC (SEQ ID NO:22) | 3829 | 3810 | 20 | 60 | 61.9 | |
| Primer Pair # 10 | | | | | | | |
| OLIGO1: | TGCTCGACAACGCGAACCTG (SEQ ID NO:23) | 3770 | 3789 | 20 | 60 | 61.9 | 280 |
| OLIGO2: | TCCGAGTTGGACCCGAAGAC (SEQ ID NO:24) | 4049 | 4030 | 20 | 60 | 61.9 | |
| Primer Pair # 11 | | | | | | | |
| OLIGO1 | TACCAGGGCAAGGATGGCAG (SEQ ID NO:25) | 3973 | 3992 | 20 | 60 | 61.9 | 280 |
| OLIGO2 | GCAAACACCAGCACCCCG (SEQ ID NO:26) | 4252 | 4235 | 18 | 66 | 61.9 | |

{#courier10 }

Two of them gave no PCR fragment, with any of the primers used, indicating that katG (SEQ ID NO:45) had been deleted. The remaining 34 strains all yielded the expected PCR products and these were analyzed on SSCP gels so that possible point mutations could be detected. In 20 cases, abnormal strand mobility was observed, compared to that of katG (SEQ ID NO:45) from drug-sensitive *M. tuberculosis*, suggesting that mutational events had indeed occurred. The approximate locations of the mutations, as delimited by the PCR primers, are shown in Table 3.

TABLE 3

Preliminary results of PCT-SSCP analysis of katG from *M. tuberculosis* strains x denotes altered mobility; del denotes deletion

| N° | Strain | MIC (INH) | 1 1765–2034 | 2 2008–2289 | 3 2169–2431 | 4 2364–2628 | 5 2622–2892 | 6 2829–3097 | 7 3088 3367 |
|---|---|---|---|---|---|---|---|---|---|
| 1/37 | 9488 | 1 | | | | | | | X |
| 2 | 9577 | 1 | | | | | | | |
| 3 | 9112 | 10 | | | | | | | |
| 4 | 9247 | 1 | | | | | | | |
| 5 | 9200 | 1 | | | | | X | | |
| 6 | 9116 | 1 | | | | | | | |
| 7/31 | 9106 | 1 | | | | | X | | X |
| 8 | 9291 | 1 | | | | | | | X |
| 9/10 | 9412 | 1 | X | | | | | | |
| 11/12 | 9435 | 1 | | | | | | | |
| 13 | 9428 | 1 | | | X | | | | |
| 14 | 9441 | 1 | | | X | | | | X |
| 15/16 | 9444 | 1 | | | X | | | | X |
| 17/18 | 9445 | 1 | | | | | | | |
| 19/20 | 9330 | 0,2 | | | X | | | | |
| 21/22 | 9420 | 0,2 | | | | | | | |
| 23 | 9262 | 0,2 | | | | | | | |
| 24/38 | 9523 | 1 | | | | | X | | |
| 25 | 9592 | 10 | | | X | | | | |
| 26 | 9553 | 10 | | | | | | | |
| 27 | 9485 | 10 | | | | | X | | |
| 28 | 9181 | 1 | | | X | | X | | |
| 29 | 9363 | 1 | | | | | | | X |
| 30 | 9465 | 1 | | | X | | | | |
| 32 | 9178 | 0,2 | | | | | | | |
| 33 | 9468 | 0,2 | | | | | | | |
| 34 | 9218 | 0,2 | | | | | | | |
| 33 | 9468 | 0,2 | | | | | | | |
| 34 | 9218 | 0,2 | | | | | | | |
| 35 | 9503 | 0,2 | | | | | | | |
| 39 | 9582 | 1 | | | | | X | | |
| 41 | H37Rv | — | | | | | | | |
| 42 | Ass | — | | | | | | | |
| 43 | Mou | — | | | | | | | |
| 44 | 13632 | >20 | del | del | del | del | del | del | del |
| 45 | 13549 | >5 | del | del | del | del | del | del | del |
| 46 | 13749 | >20 | | | | | | | |
| 47 | 14006 | 10 | | | | | | | X |
| 48 | 13711 | >5 | | | | | | | |
| 49 | 13681 | >5 | | | | | X | | |
| 50 | 14252 | >5 | | | | | | | |

On examination of a 200 bp segment of the katG gene from five independent strains (9188, 9106, 9441, 9444, 9363), a single base difference was found. This was the same in all cases, a G to T transversion at position 3360, resulting in the substitution of Arg-461 by Leu. Thus, in addition to inactivation of katG, INH-resistance can stem from missense mutations that result in an altered catalase peroxidase. This mutation may define a site of interaction between the drug and the enzyme. The results of DNA sequence studies with the remaining mutants are eagerly awaited.

Another conclusion that can be drawn from this study concerns the molecular basis of the multidrug resistance associated with various *M. tuberculosis* strains. The same mutations are found irrespective of whether a given patient is seropositive or seronegative for HIV. For example, strain 9291, isolated from an HIV-seropositive tuberculosis patient, harbors mutations conferring resistance to INH, rifampin and streptomycin in the katG (R461L), rpoB (S425L) and rpsL (K42R) genes, respectively. The same mutations have been found separately, or in combination, in strains from HIV-seronegative individuals. This means that, for the set of strains studied, there is no novel, single mechanism conferring resistance to several drugs, but rather, multidrug resistance results from the accumulation of mutations in the genes for distinct drug targets.

Example 2

Nucleotide Sequence and Chromosomal Location of the katG Locus of *M. Tuberculosis*

Bacterial strains, plasmids and growth conditions

The following bacterial strains from our laboratory collections were used in this study: *M. tuberculosis* H37Rv; *M. smegmatis* MC 155 (Snapper et al., 1990); *E. coli* K-12 UM2 (katE katG; Mulvey et al., 1988). The recombinant plasmids, pYZ55 (pUC19, katG$^+$), pYZ56 (pUC19, lacZ'::katG) and the shuttle clones, pBH4 (pYUB18, katG$^+$), and PBAK-KK-(pBAK14, katG$^+$) have been described recently (Zhang et al. 1992, *Nature*) and the katG locus of *M. tuberculosis* is schematized in FIG. 5. Mycobacteria were grown at 37° C. in Middlebrook 7H9 medium, while *E. coli* strains were cultivated in L-broth, with appropriate enrichments and antibiotics.

Nucleic acid techniques

Standard techniques were employed for the preparation, labelling and hybridization of DNA (Eiglmeier et al. 1991; Zhang et al. 1992, *Infect. Immun.*; Zhang et al. 1992, *Nature*). A shotgun library of random fragments of pYZ55 was prepared in M13mp18 as described previously (Garnier et al., 1986) and sequenced using the modified dideoxy technique (Biggin et al. 1983). Sequences were compiled and assembled into contigs using SAP, and analyzed with NIP, SIP and PIP (Staden 1987) running on a Vax 3100 workstation. Gap closure was obtained by using synthetic oligonucleotide primers, synthesized on an ABI 381 apparatus, and T7 DNA polymerase (Pharmacia) to obtain sequences directly from pYZ55. To search for related sequences in the GenBank database (release 73.1) the FASTA (Pearson et al. 1988) and BLAST (Altschul et al. 1990) programs were used. The PROSITE (Bairoch 1992) catalog was screened to detect possible motifs present in protein sequences and alignments were done with the PILEUP and PRETTY modules of the GCG sequence analysis package (Devereux et al. 1984).

Western blotting and catalase-peroxidase activity staining.

Immunoblotting of polypeptides resolved by SDS-polyacrylamide gel electrophoresis and detection with polyclonal antibodies (purchased from DAKO) raised against *M. bovis* BCG, were as described (Zhang et al. 1992, *Infect. Immun., Nature, Mol. Microbiol.*). Procedures for detecting catalase and peroxidase activities have been outlined recently (Heym et al. 1992; Zhang et al. 1992 *Nature*).

RESULTS

Nucleotide sequence of the katG locus of *M. tuberculosis*.

In previous studies, the complete katG gene (SEQ ID NO:45) was cloned independently in *E. coli* on a shuttle cosmid, pBH4, and on a 4.5 KpnI restriction fragment thus giving rise to pYZ55 (FIG. 5; Zhang et al. 1992, *Nature*). The structural gene for catalase-peroxidase was subsequently localized to a 2.5 kb EcoRV-KpnI fragment by sub-cloning. To deduce the primary structure of this important enzyme and thereby gain some insight into its putative role in the conversion of INH into a potent anti-tuberculous derivative, the nucleotide sequence of the complete insert from pYZ55 was determined. This was achieved by the modified dideoxy-shotgun cloning procedure (Biggin et al. 1993) and gaps between the contigs were closed by using specific primers.

On inspection of the resultant sequence which is shown in FIG. 6A, the 4.5 kb fragment (SEQ ID NO:45) was found to contain 4795 nucleotides with an overall dG+dC content of 64.4%. When this was analyzed for the presence of open reading frames, with high coding-probability values, a single candidate was detected and, from its size, composition and location, this was identified as katG (SEQ ID NO:45). The absence of any additional open reading frames, on either strand of the KpnI fragment, ruled out the possibility that genes other than katG were involved in conferring INH-susceptibility.

Further analysis of the sequence showed katG (SEQ ID NO:45) to be preceded by two copies of a 700 bp direct repeat which were 68% identical, with the longest stretch of identity comprising 58 bp (FIG. 6B)(SEQ ID NOS:46–47). When the databases were screened with this sequence no significant homologies were detected. To test the possibility that it could correspond to a new repetitive element in *M. tuberculosis*, a 336 bp probe, encompassing the 58 bp repeat, was used to probe a partially-ordered cosmid library. Positive hybridization signals were only obtained from clones that were known to carry katG. Likewise, a single restriction fragment was detected in Southern blots of *M. tuberculosis* DNA digested with restriction enzymes BamHI, KpnI and RsrII thereby indicating that this repetitive sequence is not dispersed.

Chromosomal location of katG (SEQ ID NO:45).

As part of the *M. tuberculosis* genome project, most of the genes for which probes are available have been positioned on the contig map. From the series of overlapping cosmids shown in FIG. 5 it can be seen that the markers linked to katG are LL105 and fbpB encoding an anonymous antigen and the putative fibronectin binding protein, or alpha antigen (Matsuo et al. 1988), respectively. None of the known insertion sequences IS6110 and IS1081 (Collins et al. 1991; McAdam et al. 1990; Thierry et al. 1990, *J. Clin. Microbiol.*; Thierry et al. 1990, *Nucleic Acids Res.*), map to this area of the chromosome although the region upstream of katG (SEQ ID NO:45) is densely populated with copies of the major polymorphic tandem repeat, MPTR (Hermans et al. 1992; Zhang and Young 1993).

Presence of katG (SEQ ID NO:45) homologues in other mycobacteria.

INH is exquisitely potent against members of the tuberculosis complex yet shows little, if any, activity against other mycobacteria. To determine whether genes homologous to katG (SEQ ID NO:45) were present in other mycobacteria Southern blots of DNA digested with RsrII were hybridized with a probe prepared from a 2.5 kb EcoRV-KpnI restriction fragment carrying katG (SEQ ID NO:45) from *M. tuberculosis*. Under conditions of high stringency good signals were obtained from *M. leprae* and *M. avium* (FIG. 7) while barely discernible hybridization was observed with *M. gordonae* and *M. szulgai*. It has been shown recently that katG homologues are also present in *M. Smegmatis* and *M. aurum* (Heym et al. 1992).

Predicted properties of catalase-peroxidase from *M. tuberculosis*.

The primary structure of catalase-peroxidase, deduced from the nucleotide sequence of katG (SEQ ID NO:45),is shown in FIG. 6 (SEQ ID NO:49) . The enzyme is predicted to contain 735 amino acids, and to display a molecular weight of 80,029 daltons. A protein of this size has been observed in *M. tuberculosis* (SEQ ID NO:48), and both recombinant *M. smegmatis* and *E. coli* (SEQ ID NO:49)(see below).

Primary structures are available for several other bacterial catalase-peroxidases including those from *E. coli* (SEQ ID NO:49), *Salmonella tyohimurium* (SEQ ID NO:50), and *Bacillus stearothermophilus* (SEQ ID NO:51)(Loewen et al. 1990; Loprasert et al. 1988; Triggs-Raine et al. 1988) and these have been shown to be distantly related to yeast cytochrome c peroxidase (SEQ ID NO:52) (Welinder 1991). As the crystal structure of the latter has been determined (Finzel et al. 1984) this can be used to interpret the sequences of the bacterial enzymes. The *M. tuberculosis* enzyme (SEQ ID NO:48) shows 53.3% conservation with the enterobacterial HPI enzymes, and shares 45.7% identity with the protein from *B. stearothermophilus* (SEQ ID NO:51). An alignment of the sequences of these four enzymes is shown in FIG. 8 (SEQ ID NOS:48-51), along with that of yeast cytochrome c peroxidase (SEQ ID NO:52) (Welinder 1991). It is apparent that the $NH_2$ terminus, which has no counterpart in the yeast enzyme, is the most divergent part suggesting that this domain of the protein can tolerate extensive deviation and is not required for catalysis. Experimental support for this interpretation is provided in the form of a LacZ-KatG fusion protein which contains an additional 40 amino acid residues (FIG. 9, lane 6; Zhang et al. 1992, *Nature*). Addition of this $NH_2$-terminal segment does not noticeably interfere with either the catalase or peroxidase reactions effected by KatG (SEQ ID NO:48) as judged by activity staining (Zhang et al. 1992, *Nature*).

Bacterial catalase-peroxidases are believed to have evolved by means of a gene duplication event and consist or two modules, both showing homology to the yeast enzyme, fused to a unique $NH_2$-terminal sequence of about 50 amino acid residues (Welinder 1991). The M. tuberculosis enzyme (SEQ ID NO:48) conforms to this pattern and when searched for internal homology using SIP (Staden 1987) it was clear that the region between residues 55–422 was related to the carboxy terminal domain, consisting of amino acids 423–735. Only one of the two active site motifs typical of peroxidases, present in the PROSITE catalog (Bairoch 1992) was found when the M. tuberculosis catalase-peroxidase primary structure (SEQ ID NO:48) was screened as there are two deviations from the consensus around $His^{269}$ where the second motif should be. (Consensus pattern for peroxidase 1: [DET]-[LIVMT]-x(2)-[LIVM]-[LIVMSTAG]-[SAG]-[LIVMSTAG]-H-[STA]-[LIVMFY] (SEQ ID NO:27); consensus pattern for peroxidase 2: [SGAT]-x(3)-[LIVMA]-R-[LIVMA]-x-[FW]-H-x-[SAC] (SEQ ID NO:28); (Bairoch 1992). In addition, a possible ATP-binding motif (G-x-x-x-x-G-K-T) was detected (Balroch 1992) but as this partially overlaps the active site its presence may be purely fortuitous (FIG. 8).

By analogy with yeast cytochrome c peroxidase (SEQ ID NO:52) (Welinder 1991), it was possible to predict a number of structurally and catalytically important residues all of which are located in the $NH_2$-terminal repeat. $His^{269}$ should serve as the fifth ligand of the heme-iron while $Asp^{380}$ should be its hydrogen-bonded partner. Other residues predicted to be involved in active site modulation and $H_2O_2$ binding are $Arg^{104}$, $Trp^{107}$, $His^{108}$, $Asn^{138}$, $Thr^{274}$ and $His^{275}$ (FIG. 4). According to Welinder's predictions (Welinder 1991), $Trp^{320}$ should be a key residue and be required for forming the protein-radical site (Sivaraja et al. 1989).

Antibody response to M. tuberculosis KatG (SEQ ID NO:48). To evaluate the possible value of KatG (SEQ ID NO:48) as an immunogen, Western blots were probed with anti-serum raised against M. bovis BCG in rabbits. As shown in FIG. 9, the 80 kD catalase-peroxidase is one of the prominent antigens recognized in cell-free extracts of M. tuberculosis, and M. smegmatis expressing the cloned katG gene (SEQ ID NO:45)(lanes 1, 3). Likewise, on introduction of the gene into E. coli significant levels of catalase-peroxidase were produced a striking increase in expression was obtained from the lacZ'-katG gene fusion which directed the synthesis of an 85 kD fusion protein (FIG. 9, lane 6).

The aim of the present study was to determine the nucleotide sequence of the katG gene (SEQ ID NO:45) and to use the information obtained to try and understand how its product (SEQ ID NO:48) mediates the INH-susceptibility of M. tuberculosis and, possibly, to explain the apparent instability of the katG region of the genome (SEQ ID NO:45). Repetitive DNA is often a source of chromosomal rearrangements and analysis of the DNA sequence upstream of katG (SEQ ID NO:45) revealed two copies of a 700 bp direct repeat (SEQ ID NOS:46–47). Since this element appears to be confined to this locus it is unlikely to serve as a target for an event, such as homologous recombination, which could lead to the deletion of the gene that is observed so frequently (Zhang et al. 1992, Nature; Zhang and Young 1993). Likewise, as a 70 kb stretch of the chromosome of M. tuberculosis H37Rv, encompassing katG (SEQ ID NO:45), is devoid of copies of IS6110 and IS1081, these insertion sequences do not appear to be likely sources of instability. Rather, the presence of a cluster of major polymorphic tandem repeats, MPTR (FIG. 5; Hermans et al. 1992 situated upstream of katG (SEQ ID NO:45), suggests that this might act as a recombinational hotspot. It may remove both the MPTR cluster and katG (SEQ ID NO:45) (Zhang and Young 1993). The availability of the sequence of the katG region (SEQ ID NO:45) will allow primers suitable for the polymerase chain reaction to be designed and thus facilitate studies aimed at both rapid detection of INH-resistance and understanding the molecular basis of chromosomal instability.

Perhaps the most intriguing feature of the M. tuberculosis catalase-peroxidase (SEQ ID NO:48) is its ability to mediate INH-susceptibility. In our current working hypothesis, the drug interacts with the enzyme and is converted by the peroxidase activity into a toxic derivative which acts at a second, as yet unknown, site (Zhang et al. 1992, Nature). Although horse radish peroxidase can effect this reaction (Pearson et al. 1988; Shoeb et al. 1985), and produce hydroxyl and organic free radicals, very few bacteria, including other mycobacteria, are sensitive to INH. This is intriguing as they contain genes homologous to katG (SEQ ID NO:45) (FIG. 7). One explanation for this could be provided by the fact that most bacterial contain two catalases, one of which is a broad spectrum enzyme endowed with peroxidase activity, and that the second catalase, by preferentially removing $H_2O_2$, limits the ability of the catalase-peroxidase to oxidize INH. As M. tuberculosis lacks the latter activity its KatG enzyme (SEQ ID NO:48) can convert INH to the lethal form without competition for the electron acceptor.

Alternatively, there may be some unique features of the M. tuberculosis enzyme which promote toxicity or favor the interaction with the drug. Examination of the primary structures of the bacterial catalase-peroxidases was not instructive in this respect as they all share extensive sequence identities and contain two motifs characteristic of the active sites of peroxidases. Furthermore, it has been shown recently that expression of the E. coli katG gene (SEQ ID NO:49) can partially restore INH-susceptibility to drug-resistant mutants of M. tuberculosis suggesting that the endogenous enzyme may not possess any drug-specific properties (Zhang et al. 1993). Sequence comparison with the cytochrome c peroxidase (SEQ ID NO:52) from yeast has provided important information about the structural and functional organization of the KatG protein (SEQ ID NO:48) and led to the identification of the putatively-important catalytic residues (FIG. 8).

Now that the complete sequence of katG (SEQ ID NO:48) is available it will be possible to test some of these hypotheses by site-directed mutagenesis and to overproduce the enzyme so that detailed analysis of the enzymatic reaction, and its products, can be performed in vitro. Likewise, it should be a relatively simple matter to isolate mutants that have retained enzymatic activity but are unable to bind or oxidized INH. Of particular interest is the repetitive structure of the enzyme and the prediction that the $NH_2$-terminal repeat contains the active site for peroxidases. This raises the possibility that katG genes (SEQ ID NO:45), mutated, or truncated at the 3'-end, could arise. It is conceivable that their products, lacking the normal COOH-terminus which may be required for subunit-subunit interactions (Welinder 1991), would be unstable but still retain low enzyme activity. They would thus confer an intermediate level of INH-susceptibility, between that of $katG^+$ strains and mutants completely lacking the gene, as is often observed in clinical settings.

The invention may of course make use of a part of the above described 2.5 kb EcoRV-KpnI fragment, said part being nonetheless sufficiently long to provide for the selectivity of the in vitro detection of a *Mycobacterium tuberculosis* resistant to isoniazid.

The invention also relates to a kit for detecting multidrug resistant variants of *M. tuberculosis* wherein the kit comprises:

(a) a container means containing a probe for the gene encoding drug resistance; and (b) a container means containing a control preparation of nucleic acid.

Needless to say that use can be made of any detection method alternative bringing into play the nucleodic sequence specific of nucleic acids of a Mycobacterium resistant to isoniazid, e.g. a method using an amplification technique and primers, whereby said primers may either be contained within said specific nucleotidic sequence, in order to provide for amplification fragments containing at least a part of the nucleotide sequence of the above mentioned probe, nonetheless sufficiently long to provide for the selectivity of the in vitro detection of a *Mycobacterium tuberculosis* resistant to isoniazid, and finally detecting a possible mutation in any of the amplified sequences.

A preferred process alternative (oligotyping) for the detection of resistance to the selected antibiotic comprises:

fragmenting the relevant gene or part thereof likely to carry the mutation into a plurality of fragments, such as by digestion of said relevant gene by selected restriction enzymes, hybridizing these fragments to complementary oligonucleotide probes, preferably a series of labelled probes recognizing under stringent conditions, all of the parts of the relevant gene of a corresponding control DNA of a strain non-resistant to the corresponding antibiotic, and relating the absence of hybridization of at least one of said oligonucleotide probes to any of the DNA fragments of the relevant gene of the mycobacterium under study as evidence of the presence of a mutation and, possibly, of a resistance to the corresponding antibiotic, particularly as compared to the running of the test under the same conditions with the same oligonucleotides on the relevant gene(s) obtained from a strain (strains) not resistant to said antibiotic.

Another process alternative (SSCP analysis, i.e. analysis of Single Stranded Conformation Polymorphisms) comprises:

digesting the DNA to be analyzed, particularly of the relevant gene, amplifying the fragments obtained, e.g. by PCR, recovering the amplified fragments, and separating them from one another according to sizes, e.g. by causing them to migrate, for instance on an electrophoretic gel, comparing the sizes of the different fragments with those obtained from the DNA(s) of one or several control strains not resistant to the antibiotic, which had been subjected to a similar assay, and relating the polymorphism possibly detected to the existence of a mutation in the relevant gene, accordingly to a possible resistance to the corresponding antibiotic of the strain from which the DNA-under study had been obtained.

Needless to say that any other method, including classical sequencing techniques, can resorted to for the achievement of the same purpose.

This method includes that known under the expression "oligotyping" for the detection of polymorphisms, reference is advantageously made to the method discloses by Orita et al. (reference was already made thereto herebefore) for the detection of polymorphisms based on the conformation of single strands.

The relevant gene in the case of resistance to isoniazid is of course the katG gene (SEQ ID NO:45) or a fragment thereof.

In the case of resistance to rifampicin, the relevant gene happens to be the rpoB gene (SEQ ID NO:59) which codes for the βsub-unit of the RNA polymerases of said mycobacteria, or when only part of that gene is being used, preferably that part which includes the codons 400 to 450 of that rpoB gene.

Finally, in the case of resistance to steptomycin, the relevant gene contemplated is that of the rpsL gene (SEQ ID NO:63) that codes for the S12 protein of the small ribosome sub-unit or, when only part of said fragment is being used, preferably that part which includes the codon at the 43 position.

A preferred procedure, particularly in relation to the process alternative making use of PCR amplification is disclosed hereafter.

DNA is obtained from a biological sample (e.g. blood or sputum) after removal of the cellular debris and lysis of the bacterial cells with an appropriate lysis buffer. PCR amplication can be carried out by classical methods, using a pair of primers, whose sequences are respectively complementary to fragments of each of the strands of the DNA to be amplified.

The procedure may be run further as follows:

the amplification products (comprising e.g. from 100 to 300 nucleotides) are digested by means of suitable restriction endonuclease, the ADN strands obtained from the amplification medium are subjected to denaturation, the monostranded DNA strands are deposited on a neutral 5% polyacrylamid gel, the monostranded DNA strands are caused to migrate on said gel by means of electrophoresis, the DNA fragments that migrated on the polyacrilamid gel are transferred onto a nylon membrane according to a usual electrophoretic blotting technique and hybridized to labelled probes, for instance $^{32}$P labelled probes, and the migration distances of the DNA fragments subjected to analysis are compared to those obtained from controls obtained under the same conditions of amplification, digestion, denaturation electrophoresis and transfer onto a nylon membrane, whereby said DNA had been obtained from an identical bacterial strain yet sensitive to the antibiotic under study.

For the production of the PCR primers as well as of the polygonucleotides probes used in the above disclosed "oligotyping" procedures, use is advantageously made of those complementary to the rpoB gene (SEQ ID NO:59) of wild *M. tuberculosis* inserted in a plasmid deposited under number I-12167 at the CNCM on Sep. 15, 1992.

The invention also relates more particularly to the nucleotidic sequence of a fragment of rpsL gene (SEQ ID NO:63) of *Mycobacterium tuberculosis* coding for the S12 protein of the small ribosome sub-unit, as well as to the nucleotidic sequence of a mutated rpsL gene fragment deemed responsible of the resistance to streptomycin.

By amplification of that nucleotidic sequence, the nucleotide sequence of the full rpsL gene can be obtained.

Further illustration of the invention will be provided in the following description of additional examples.

Example Concerning Rifampicin In Mice

The sensitivity to rifampicin has been determined in mice as disclosed by Grosset et al. (and Int. J. Lepr. 57:607–614). The cells of M. Leprae were obtained from mouse paws according to classic procedures. All resistant strains were able to grow in mice which received daily doses of 20 mg/Kg of rifampicin, whereas sensitive strains were killed at low rifampicin concentrations, less than 2 mg/Kg.

Relevant regions of the rpoB gene of extracted DNA was initiated upon using two pairs of biotinylated primers, whose sequences appear in the following table.

TABLE

| Primer | Sequence |
| --- | --- |
| Brpo22 | CAGGACGTCGAGGCGATCAC (SEQ ID NO:30) |
| rpo23 | AACGACGACGTGGCCAGCGT (SEq ID NO:31) |
| Brpo24 | CAGACGGTGTTTATGGGCGA (SEQ ID NO:32) |
| rpo25 | TCGGAGAAACCGAAACGCTC (SEQ ID NO:33) |
| rpo32 | TCCTCGTCAGCGGTCAAGTA (SEQ ID NO:34) |
| rpo33 | CTTCCCTATGATGACTG (SEQ ID NO:35) |
| rpo34 | GGTGATCTGCTCACTGG (SEQ ID NO:36) |
| rpo35 | GCCGCAGACGCTGATCA (SEQ ID NO:37) |
| rpo36 | TTGACCGCTGACGAGGA (SEQ ID NO:38) |
| rpo37 | GCCAGCGTCGATGGCCG (SEQ ID NO:39) |

Upon using conventional techniques, amplification products comprising 310 and 710 bp were respectively obtained as shown in FIG. 1. The localization of the sequences of the different primers used in the table is also indicated on FIG. 10.

The DNAs obtained have been sequenced on the basis of the rpoB sequence of isolates sensitive to rifampicin (SEQ ID NO:59). A plasmid containing the sequence of that gene has been deposited at CNCM on Sep. 15, 1992 under number I-1266. Biotinylated PCR products were concentrated from the PCR reaction mixtures by contacting with streptavidin coated beads under agitation. The biotinylated strands attached to the beads were then recovered and sequenced. The sequences obtained were compared to the sequence of the rpoB gene or a wild type strain (SEQ ID NO:59). Significant results were obtained as a result or sequencing of the wild gene (SEQ ID NO:59)(of a mycobacterium sensitive to rifampicin) and of corresponding sequences of the β-sub-unit of four mutant strains resistant to rifampicin (FIG. 11).

Results were obtained starting from 102 strands obtained from patients infected with M.tuberculosis. Among this 102 strands 53 were sensitive to rifampicin and 49 resistant to rifampicin. The mutation was localized in the region 400–450 in 43 of the mutants and among the latter, the mutation occurred in the region of $^{425}$Ser into leu.

Example of detection of the resistance of mycobacteria to streptomycin

The culture of M.tuberbulosis strains and the test of their sensitivity to streptomycin have been carried out by the method of proportions on a Lowenstein-Ierva medium (Laboratory Method for Clinical Mycobacteriology—Hugo David—Veronique Levy Frebault, M. F. Thorel, published by Institut Pasteur).

The nucleotide sequence of the rpsL gene (SEQ ID NO:61) of M.Leprae led, by sequence analogy, to the construction of two primers, ML51 (CCCACCATTCAGCAGCTGGT)(SEQ ID NO:40) and ML52 (GTCGAGCGAACCGCGAATGA)(SEQ ID NO:41) surrounding regions including putative mutation sites liable of being responsible for the streptomycin resistance and suitable for the PCR reaction. The DNA of the used M.tuberculosis used as a matrix has enabled one to obtain a rpsL fragment of 306 pb (SEQ ID NO:63). The nucleotide sequence of the sequenced fragments exhibited 28 differences with that of M.Leprae.

The rpsL genes or 43 strands of M.tuberculosis, among which 28 were resistant, have been amplified both by PCR and the SSCP technique.

DNA was extracted from 200 μl aliquots of M.tuberculosis samples (in average $10^4$ to $10^5$ bacteria) covered by 100 μl of mineral oil by a congelation-decongelation technique (Woods and Cole, 1989 FEBS. Microbiol. Lett,65:305–308).

After electrophoresis of the DNA strands tested a mutation was shown in 16 of the mutants. In order to establish the nature of the mutation in the 16 strands under consideration, the corresponding rpsL gene fragments were amplified by PCR using the ML51 (SEQ ID NO:40) and the ML52 (SEQ ID NO:41) primers and their respective nucleotide sequences were determined.

The sequences obtained were compared to the sequence of the wild type rpsL gene (SEQ ID NO:65). The single difference was found with the wild sequence ; codon 43, AAG, was mutated into AGG and, consequently, the lys-42 aminoacid was replaced by Arg.

The invention relates also to the "mutated" DNA fragments. They can in turn be used as hybridization probes for use for the detection in suitable hybridization procedures and for the detection of similar mutation in DNA extracted from a M.tuberbulosis strain suspected to include resistance to any one of the above illustrated antibiotics.

The invention further relates to kits for the resistance of mycobacteriae to isoniazid, rifampicin or analogues thereof, and streptomycin.

The invention further relates to a kit for the in vitro diagnostic of the resistance of a bacteria of a mycobacterium genus to isoniazid, characterized in that it comprises:

means for carrying out for a genic amplification of the DNA of the katG gene (SEQ ID NO:45) or of a fragment thereof, means to bring into evidence one or several mutations on the amplification products so obtained, a preparation of control DNA of a katG gene (SEQ ID NO:45) of a strain of said bacteria sensitive to isoniazid or of a fragment thereof, optionally, a control preparation of a DNA of the katG gene (SEQ ID NO:45) of an isoniazid-resistant mycobacterium strain.

The invention further relates to a kit for the in vitro diagnostic of the resistance of a bacteria of a mycobacterium genus to rifampicin or its analogues, characterized in that it comprises:

means for carrying out for a genic amplification of the DNA of the rpoB gene (SEQ ID NO:59) or of the β-sub-unit of the RNA polymerase (SEQ ID NO:60) of said mycobacteria, or of a fragment thereof, means to bring into evidence one or several mutations on the amplification products so obtained, a preparation of control DNA of a rpoB gene coding for the β-sub-unit of the RNA polymerase of a strain of said bacteria sensitive to rifampicin or of a fragment thereof, optionally, a control preparation of a DNA of the rpoB gene (SEQ ID NO:59) of an isoniazid-resistant mycobacterium strain.

Similarly, the invention pertains to a kit for the in vitro diagnostics of the resistance of the *M.tuberculosis* to streptomycin, characterized in that it includes:

means for carrying out a genic amplification of the rpsL gene (SEQ ID NO:63) coding for the S12 protein of the small ribosome sub-unit, or fragment thereof, means which enable the bringing to evidence of one or several mutations on the amplification products obtained, a control preparation of a DNA sequence of the rpsL gene (SEQ ID NO:65) coding for the S12 protein of the small sub-unit of the ribosome (SEQ ID NO:66) of a *M.tuberculosis* strain sensitive to streptomycin, and optionally, a control preparation of a DNA sequence of a rpsL gene (SEQ ID NO:63) coding for the S12 protein of the small sun-unit or the ribosome (SEQ ID NO:64) of a strain of *M.tuberculosis* resistant to streptomycin.

REFERENCES CITED IN THE SPECIFICATION

Altschul, S., Gish, W., Miller, W., Myers, E., and Lipman, D. (1990). A basic local alignment search tool. *Proc. Natl. Acad. Sci. USA* 215:403–410.

Bekierkunst, A. & Bricker, A. (1967). Studies on the mode of action of isoniazid on mycobacteria. *Arch. Biochem. Biophys.* 122:385–392.

Biggin, M. D., Gibson T. J., and Hong G. F. (1983). Buffer gradient gels and $^{35}$S-label as an aid to rapid DNA sequence determination. *Proc. Natl. Acad. Sci. USA* 80:3963–3965.

Bairoch, A., (1992). Prosite: a dictionary of sites and patterns in proteins. *Nucleic Acids Res.* 20:2013–2018.

C. D. C. Outbreak of multidrug-resistant tuberculosis—Texas, California, and Pennsylvania. MMWR 1990, 39:369–372.

C. D. C. Nosocomial transmission of multidrug-resistant tuberculosis among HIV-infected persons—Florida and New York 1988–1991. MMWR 1991(a) 40:585–591.

C. D. C. Transmission of multidrug-resistant tuberculosis from an HIV-positive client in a residential substance abuse treatment facility. Michigan. MMWR 1991(b), 40:129–131.

Chaisson, R. E., Schecter, G. F., Theuer, C. P., Rutherford, G. W., Echenberg, D. F., Hopewell, P. C. (1987). Tuberculosis in patients with the acquired immunodeficiency syndrome. *Am. Rev. Respir. Dis.,* 23:56–74.

Collins, D. M., and Stephens, D. M. (1991). Identification of an insertion sequence, 1S1081, in *Mycobacterium bovis. FEMS Microbiol. Lett.* 83:11–16.

Daley, C. L., Small, P. M., Schecter, G. F., Schoolnik, G. K., McAdam, R. A., Jacobs, W. R., and Hopewell, P. C. (1992). An outbreak of tuberculosis with accelerated progression among persons infected with the human immunodeficiency virus. An analysis using restriction-fragment-length-polymorphism. *N. Engl. J. Med.,* 326:231–235.

Devereux, J., Haeberli, P. and Smithies, O. (1984) A comprehensive set of sequence analysis programs for the VAX. *Nucl. Acids Res.* 12:387–395.

Eiglmeier, K., Honore, N., and Cole, S. T. (1991). Towards the integration of foreign DNA into the chromosome of *Mycobacterium leprae. Research in Microbiology,* 142:617–622.

Finzel, B. C., Poulos, T. L. and Kraut, J. (1984). Crystal structure of yeast cytochrome C peroxidase at 1.7 Å resolution. *J. Biol. Chem.* 259:13027–13036.

Garnier, T., and Cole, S. T., (1986). Characterization of a bacteriocinogenic plasmid from *Clostridium perfringens* and molecular genetic analysis of the bacteriocin-encoding gene. *J. Bacteriol.,* 168:1189–1196.

Gayathri Devi, B., Shaila, M. S., Ramakrishnan, T., and Gopinathan, K. P. (1975). The purification and properties of peroxidase in *Mycobacterium tuberculosis* H37RV and its possible role in the mechanism of action of isonicotinic acid hydrazide. *Biochem. J.,* 149:187–197.

Hermans, P. W. M., van Soolingen, D. and van Embden, J. D. A. (1992). Characterization of a major polymorphic tandem repeat in *Mycobacterium tuberculosis* and its potential use in the epidemiology of *Mycobacterium kansasii* and *Mycobacterium Ågordonae. J. Bacteriol.* 174:4157–4165.

Heym, B. and Cole, S. T. (1992). Isolation and characterization of isoniazid-resistant mutants of *Mycobacterium smegmatis* and *M. aurum. Res. Microbiol.*, submitted.

Jackett, P. S., Aber, V. and Lowrie, D. (1978). *J. Gen Microbiol.,* 104:37–45.

Kubica, G. P., Jones Jr., W. D., Abbott, V. D., Beam, R. E., Kilburn, J. O., and Cater Jr., J. C. (1966). Differential identification of mycobacteria. I. Tests on catalase activity. *Am. Rev. Rest. Dis.,* 94:400–405

Kwok et al., S., *J. Virol.* 61:1690–1694 (1987). Multidrug resistance results from the accumulation of mutations in the genes for distinct drug targets.

Laemmli, U. K., (1970). Cleavage of structural proteins during the assembly of the head of bacteriophage-T4 *Nature* (London) 227:680–685.

Loewen, P. C., and Stauffer, G. V. (1990). Nucleotide sequence of katG of Salmonella typhimurium LT2 and characterization of its product, hydroperoxidase I. *Mol. Gen. Genet.* 224:147–151.

Loprasert, S., Negoro, S. and Okada, H. (1988). Thermostable peroxidase from *Bacillus stearothermophilus. J. Gen. Microbiol.,* 134:1971–1976.

Loprasert, S., Negoro, S., and Okada, H. (1989). Cloning, nucleotide sequence, and expression in *Escherichia coli* of the *Bacillus stearotherrmophilus* peroxidase gene (perA). *J. Bacteriol.,* 171:4871–4875.

Maniatis, T., Sambrook, J., and Fritsch, E. F. (1989). Molecular cloning. A laboratory manual. Second Edition 1989. Cold Spring Harbor Laboratory Press.

Matsuo, K., Yamaguchi, R., Yamazaki, R. A., Tasaka, H. and Yamada, T. (1988). Cloning and expression of the *Mycobacterium bovis* BCG gene for extracellular a antigen. *J. Bacteriol.,* 170:3847–3854.

Middlebrook, G. (1954). Isoniazid-resistance and catalase activity of tubercle bacilli. *Am. Rev. Tuberc.,* 69:471–472.

Middlebrook, G., Cohn, M. L., and Schaefer, W. B. (1954). —Studies on isoniazid and tubercle bacilli. III. The isolation, drug-susceptibility, and catalase-testing of tubercle bacilli from isoniazid-treated patients. *Am. Rev. Tuberc.,* 70:852–872.

Mitchison, D. A., Selkon, J. B. and Lloyd, S. (1963). *J. Path. Bact.* 86:377–386.

Mulvey, M. R., Sorby PA, Triggs-Raine BL and Loewen PC. *Gene* 73:337–345 (1988).

Orita, M., Iwahana, I., Kanazawa, H., Itayashi, K., and Sekiya, J. (1989). *PNAS* 86:2766–2770.

Pearson, W., and Lipman, D. (1988). Improved tools for biological sequence comparisons. *Proc. Natl. Acad. Sic. USA.* 85:2444–2448.

Quemard, A., Lacave, C., and Laneelle, G. (1991). Isoniazid inhibition of mycolic acid synthesis by cell extracts of sensitive and resistant strains of *Mycobacterium aurum. Antimicrob. Ag. Chem.,* 35:1035–1039.

Saiki et al., R. K., *Bio/Technology* 3:1008–1012 (1985).

Shoeb, H. A., Bowman B. U. J., Ottolenghi, A. C., and Merola, A. J. (1985). Peroxidase-mediated oxidation of isoniazid. *Antimicrobial Agents and Chemotherapy*, 27:399–403

Shoeb, H. A., Bowman, B. U. J., Ottolenghi, A. C., and Merola, A. S. (1985). Evidence for the generation of active oxygen by isoniazid treatment of extracts of *Mycobacterium tuberculosis* H37Ra. *Antimicrobial Agents and Chemotherapy*, 27:404–407.

Sivaraja, M., Goodin, D. B., Smith, M., and Hoffman, B. M., (1989). Identification by ENDOR of Trp[191] as the free-radical site in cytochrome c peroxidase Compound Es. *Science*, 245:738–740.

Snapper, S. B., Lugosi, L., Jekkel, A., Melton, R. E., Kieser, T., Bloom, B. R., and Jacobs, W. R. (1988). Lysogeny and transformation in mycobacteria: stable expression of foreign genes. *Proc. Natl. Acad. Sci. USA*, 85:6987–6991.

Snapper, S. B., Melton, R. E., Mustafa, S., Kieser, T., and Jacobs, W. R. (1990). Isolation and characterization of efficient plasmid transformation mutants of *Mycobacterium smegmatis*. *Mol. Microbiol.*, 4:1911–1919.

Snider, D. (1989). *Rev. Inf. Dis.*, S335.

Snider Jr., D. E. and Roper, W. L. (1992). The new tuberculosis. *The New England Journal of Medicine*, 326:703–705.

Sriprakash, K. S. and Ramakrishnan, T. (1970). Isoniazid-resistant mutants of *Mycobacterium tuberculosis* H37Rv: Uptake of isoniazid and the properties of NADase inhibitor. *J. Gen. Microbiol.*, 60:125–132.

Staden, P. (1987). Computer handling of sequence projects. In Nucleic acid and protein sequence analysis: A practical approach. Bishop, M. J. and Rawlings, C. J. (eds.) Oxford: IRL Press, pp. 173–217.

Thierry, D., Brisson-Noel, A., Vincent-Levy-Frebault, V., Nguyen, S., Guesdon, J., and gicquel, B. (1990). Characterization of a *Mycobacterium tuberculosis* insertion sequence, IS6110, and its application in diagnosis. *S. Clin. Microbiol.*, 28:2668–2673.

Thierry, D., Cave, M. D., Sisenach, K. D., Crawford, S. T., Bates, S. H., Gicquel, B., and Guesdon, J. L. (1990). IS6110, an IS-like element of *Mycobacterium tuberculosis* complex. *Nucleic Acids Res.*, 18:188.

Triggs-Raine, B. L., Doble, B. W., Mulvey, M. R., Sorby, P. A., and Loewen, P. C. (1988). Nucleotide sequence of katG, encoding catalase HPI of *Escherichia coli. J. Bacteriol.*, 170:4415–4419.

Wayne, L. G. and Diaz, G. A. (1986). *Analyt. Biochem.* 157:89–92.

Welinder, K. G. (1991). Bacterial catalase-peroxidases are gene duplicated members of the plant peroxidase superfamily. *Biochim. Biophys. Acta* 1080:215–220.

Winder, F. and Collins, P. (1968). The effect of isoniazid on nicotinamide nucleotide levels in *Mycobacterium bovis*, strain BCG. *Amer. Rev. Pespir. Dis.*, 97:719–720.

Winder, F. and Collins, P. (1969). The effect of isoniazid on nicotinamide nucleotide concentrations in tubercle bacilli. *Amer. Rev. Respir. Dis.*, 100:101–103.

Winder, F. and Collins, P. (1968). Inhibition by isoniazid of synthesis of mycolic acids in *Mycobacterium tuberculosis, J. Gen. Microbiol.*, 63:41–48.

Youatt, J. (1969). A review of the action of isoniazid. *Am. Rev. Respir. Dis.*, 99:729–749.

Zhang, Y., Garbe, T., and Young, D. (1993). Transformation with katG restores isoniazid-sensitivity in *Mycobacterium tuberculosis* isolates resistant to a range of drug concentrations. *Mol. Microbiol.*, submitted.

Zhang, Y., and Young, D. B. (1993) Characterization of a variable genetic element from the katG region of *Mycobacterium tuberculosis*—in preparation.

Zhang, Y., Lathigra, R., Garbe, T., Catty, D., and Young, D. (1991) Genetic analysis of superoxide dismutase, the 23 kilodalton antigen of *Mycobacterium tuberculosis. Mol. Microbiol.*, 5:381–391.

Zhang, Y., Heym, B., Allen, B., Young, D., and Cole, S. T. (1992). The catalase-peroxidase gene and isoniazid resistance of *Mycobacterium tuberculosis. Nature.* 358:591–593.

Zhang, Y., Garcia, M. J., Lathigra, R., Allen, B., Moreno, C., van Embden, D. A., and Young, D. (1992). Alterations in the superoxide dismutase gene of an isoniazid-resistant strain of *Mycobacterium tuberculosis. Infect. Immun.*, 60:2160–2165.

---

---

What is claimed is:

1. A process for the detection of a resistance to an antibiotic in a mycobacterium which comprises detecting a mutation in a gene selected from the group consisting of the katG (SEQ ID NO:45) gene or fragment thereof, the rpoB (SEQ ID NO: 59) gene or fragment thereof and the rpsL (SEQ ID NO:63) gene or fragment thereof.

2. A process of claim 1 for detecting in vitro the presence of nucleic acids of a *Mycobacterium tuberculosis* resistant to isoniazid, wherein the process comprises the steps of:

contacting said nucleic acids previously made accessible to a probe if required under conditions permitting hybridization;

detecting any probe that had hybridized to said nucleic acids;

wherein said probe comprises a nucleic acid sequence, which is 2.5 kb EcoRV-KpnI fragment of plasmid pYZ56 or of part thereof, and wherein said fragment contains a BamHI cleavage site, wherein said part is nonetheless sufficiently long to provide for the selectivity of the in vitro detection of a *Mycobacterium tuberculosis* resistant to isoniazid.

3. The process as claimed in claim 2, which comprises the steps of :

(A) depositing and fixing nucleic acids of *Mycobacterium tuberculosis* on a solid support, so as to make the nucleic acids accessible to a probe;

(B) contacting said fixed nucleic acids from step (A) with the probe under conditions permitting hybridization;

(C) washing said filter resulting from step (B), so as to eliminate any non-hybridized probe; and then (D) detecting any hybridized probe on said solid support resulting from step (C).

4. The process of claim 2 or 3 wherein said probe comprises a nucleic acid sequence which encodes a polypeptide of the formula APLNSWPDNASLDKAR-RLLWPSKKKYGKKLSWADLIV (SEQ ID NO:2).

5. A process as claimed in any of claims 1 to 3, wherein the probe has a radioactive label selected from the group consisting of radioactive, enzymatic, fluorescent, and luminescent labels.

6. The process of any one of claims 1 to 3 wherein the presence of *Mycobacterium tuberculosis* resistant to isoniazid in a bacteria-containing sample suspected of containing *Mycobacterium tuberculosis* resistant to isoniazid, whereby the detection of the probe that had hybridized, is indicative of the presence in said sample of *Mycobacterium tuberculosis* resistant to isoniazid.

7. The process of claim 6, wherein prior to the contacting of said DNA with said probe, said bacteria had been separated from said sample and immobilized on a DNA binding support.

8. A kit for the detection of *Mycobacterium tuberculosis* resistant to isoniazid, wherein the kit comprises:
    (A) a container means containing a probe labelled by a label selected from the group consisting of radioactive, enzymatic, fluorescent, and luminescent labels, comprising a nucleic acid sequence, which is a 2.5 kb EcoRV-KpnI fragment of plasmid pYZ56 or part thereof, wherein said fragment contains a BamHI cleavage site and to provide for the selectivity of the in vitro detection of a *Mycobacterium tuberculosis* resistant to isoniazid; and
    (B) a container means containing a control preparation of nucleic acid.

9. A nucleic acid probe for detecting *Mycobacterium tuberculosis* resistant to isoniazid, wherein said probe consists of a 2.5 kb EcoRV-KpnI fragment of plasmid pYZ56, wherein said fragment contains a BamHI cleavage site, or of a part of said fragment nonetheless sufficiently long to provide for the selectivity of the in vitro detection of a *Mycobacterium tuberculosis* resistant to isoniazid.

10. The probe as claimed in claim 9, which is DNA free of human serum proteins or human tissue or both, viral proteins, bacterial proteins, and nucleotide sequences encoding said proteins.

11. A hybrid duplex molecule consisting essentially of the probe of claim 9 hydrogen bonded to a nucleotide sequence of complementary base sequence.

12. A process for selecting a nucleotide sequence of a *Mycobacterium tuberculosis* resistant to isoniazid from a group of nucleotide sequences, comprising the step of determining which of said nucleotide sequences hybridizes to a probe as claimed in claim 9 or 10.

13. A process for detecting point mutations or partial deletion of the KatG gene comprising contacting a sample of *Mycobacterium tuberculosis* with the probe of claim 9 or 10.

14. The process of claim 1 for the detection of resistance to the selected antibiotic, which comprises:
    digesting the relevant gene or fragment thereof likely to carry the mutation into a plurality of fragments with selected restriction enzymes,
    hybridizing the plurality of fragments to complementary labeled oligonucleotide probes under stringent hybridization conditions, wherein said probes are derived from all of the parts of the relevant gene of a corresponding control DNA of a strain non-resistant to the corresponding antibiotic,
    and correlating the absence of hybridization of at least one of said oligonucleotide probes to any of the DNA fragments of the relevant gene of the mycobacterium under study with the resistance of the mycobacterium to the corresponding antibiotic as compared to results obtained upon running the test under the same conditions with the same oligonucleotides on the relevant gene obtained from at least one strain not resistant to said antibiotic,
    wherein said relevant gene is the katG gene (SEQ. ID NO:45) or a fragment thereof, the rboB gene (SEQ ID NO:59) or a fragment thereof, or the rpsL gene (SEQ ID NO:63) or a fragment thereof.

15. The process of claim 1, which comprises:
    digesting the DNA to be analyzed comprising the relevant gene,
    amplifying the fragments obtained
    recovering the amplified fragments, and
    separating the amplified fragments from one another according to sizes,
    comparing the sizes of the different fragments with those obtained from at least one DNA derived from one control strain not resistant to the antibiotic, which had been subjected to a similar assay, and
    correlating the detection of a polymorphism with the resistance of the strain to the corresponding antibiotic of the strain from which the DNA under study had been obtained,
    wherein said relevant gene is the katG gene (SEQ ID NO:45) or a fragment thereof, the rboB gene (SEQ ID NO:59) or a fragment thereof, or the rpsL gene (SEQ ID NO:63) or a fragment thereof.

16. A kit for the in vitro of the resistance of a bacteria of a mycobacterium genus of isoniazid or its analogoues comprising:
    primers for the amplification of the DNA of the katG gene (SEQ ID NO:45) or a fragment thereof;
    reagents for amplifying said DNA;
    at least one detectably labeled probe capable of hybridizing with the amplified nucleotide sequence to be detected; and
    a control DNA of katG gene (SEQ ID NO:45) of a strain of said bacteria sensitive to isoniazid or a fragment thereof.

17. The kit of claim 16, wherein said control DNA of the katG gene is derived from an isoniazid-resistant mycobacterium strain.

18. A kit for the in vitro diagnostic of the resistance of a bacteria of a mycobacterium genus to rifampicin or its analogues, characterized in that it comprises:
    primers for the amplification of the DNA of the rpoB gene (SEQ ID NO:59), the β-sub-unit of the RNA polymerase of said mycobacteria, or a fragment thereof;
    reagents for amplifying said DNA;
    at least one detectably labeled probe capable of hybridizing with the amplified nucleotide sequence to be detected; and
    a control DNA of rpoB gene (SEQ ID NO:45) coding for the β-sub-unit of the RNA polymerase of a strain of said bacteria sensitive to rifampicin, or a fragment thereof.

19. The kit of claim 18, wherein said control DNA of the rpoB gene is derived from a rifampicin-resistant mycobacterium strain.

20. A kit for the in vitro diagnostic of the resistance of a bacteria of a mycobacterium genus to streptomycin or its analogues, characterized in that it comprises:

primers for the amplification of the DNA of the rpsL gene (SEQ ID NO:63) coding for the S 12 protein of the small ribosome sub-unit or a fragment thereof;

reagents for amplifying said DNA;

at least one detectably labeled probe capable of hybridizing with the amplified nucleotide sequence to be detected; and a control preparation of a DNA of rpsL gene (SEQ ID NO:65) coding for the S12 protein of the small sub-unit of the ribosome (SEQ ID NO:66) of the M. tuberculosis strain sensitive to streptomycin, or a fragment thereof.

21. The kit of claim 20, wherein said control DNA of the rpsL gene (SEQ ID NO:63) coding for the S 12 protein of the small sub-unit of the ribosome is derived from a streptomycin-resistant mycobacterium strain.

* * * * *

UNITED STATES PATENT AND TRADEMARK OFFICE
CERTIFICATE OF CORRECTION

PATENT NO.: 5,851,763

DATED: December 22, 1998

INVENTOR(S): Beate HEYM et al.

It is certified that an error appears in the above-identified patent and that said Letters Patent is hereby corrected as shown below:

Column 94, lines 1-3, claim 16 should read --A kit for the *in vitro* diagnosis of the resistance of a bacteria of a mycobacterium genus to isoniazid or its analogues, comprising:--.

Signed and Sealed this

Eleventh Day of April, 2000

*Attest:*

Q. TODD DICKINSON

*Attesting Officer*

*Director of Patents and Trademarks*

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TTCATCCGCA    TGGCCTGGCA    CGGCGCGGGC    ACCTACGC    39

( 2 ) INFORMATION FOR SEQ ID NO:2:

( i ) SEQUENCE CHARACTERISTICS:
        ( A ) LENGTH: 37 amino acids
        ( B ) TYPE: amino acid (C) STRANDEDNESS: single
(D) TOPOLOGY: linear (i i) MOLECULE TYPE: peptide (x i) SEQUENCE DESCRIPTION: SEQ ID NO:2:

| Ala | Pro | Leu | Asn | Ser | Trp | Pro | Asp | Asn | Ala | Ser | Leu | Asp | Lys | Ala | Arg |
|---|---|---|---|---|---|---|---|---|---|---|---|---|---|---|---|
| 1 | | | | 5 | | | | | 10 | | | | | 15 | |

| Arg | Leu | Leu | Trp | Pro | Ser | Lys | Lys | Tyr | Gly | Lys | Lys | Leu | Ser | Trp |
|---|---|---|---|---|---|---|---|---|---|---|---|---|---|---|
| | | | 20 | | | | 25 | | | | | 30 | | |

| Ala | Asp | Leu | Ile | Val |
|---|---|---|---|---|
| | | 35 | | |

(2) INFORMATION FOR SEQ ID NO:3:

(i) SEQUENCE CHARACTERISTICS:
(A) LENGTH: 37 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:3:

| Ala | Pro | Leu | Asn | Ser | Trp | Pro | Asp | Asn | Val | Ser | Leu | Asp | Lys | Ala | Arg |
|---|---|---|---|---|---|---|---|---|---|---|---|---|---|---|---|
| 1 | | | | 5 | | | | | 10 | | | | | 15 | |

| Arg | Leu | Leu | Trp | Pro | Ile | Lys | Gln | Lys | Tyr | Gly | Gln | Lys | Ile | Ser | Trp |
|---|---|---|---|---|---|---|---|---|---|---|---|---|---|---|---|
| | | | 20 | | | | | 25 | | | | | | 30 | |

| Ala | Asp | Leu | Phe | Ile |
|---|---|---|---|---|
| | | 35 | | |

(2) INFORMATION FOR SEQ ID NO:4:

(i) SEQUENCE CHARACTERISTICS:
(A) LENGTH: 36 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:4:

| Ala | Pro | Leu | Asn | Ser | Trp | Pro | Asp | Asn | Ala | Asn | Leu | Asp | Lys | Ala | Arg |
|---|---|---|---|---|---|---|---|---|---|---|---|---|---|---|---|
| 1 | | | | 5 | | | | | 10 | | | | | 15 | |

| Arg | Cys | Leu | Gly | Arg | Ser | Lys | Arg | Asn | Thr | Gly | Thr | Lys | Ser | Leu | Gly |
|---|---|---|---|---|---|---|---|---|---|---|---|---|---|---|---|
| | | | 20 | | | | | 25 | | | | | 30 | | |

| Pro | Ile | Cys | Ser |
|---|---|---|---|
| | | 35 | |

(2) INFORMATION FOR SEQ ID NO:5:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:5:

GCGGGGTTAT CGCCGATG 18

(2) INFORMATION FOR SEQ ID NO:6:

(i) SEQUENCE CHARACTERISTICS:
(A) LENGTH: 19 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GCCCTCGACG GGGTATTTC                   19

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AACGGCTGTC CCGTCGTG                    18

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTCGTGGATG CGGTAGGTG                   19

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TCGACTTGAC GCCCTGACG                   19

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CAGGTCCGCC CATGACAG                    18

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CCACAACGCC AGCTTCGAC 19

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGTTCACGTA GATCAGCCCC 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GCAGATGGGG CTGATCTACG 20

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

ACCTCGATGC CGCTGGTG 18

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GCTGGAGCAG ATGGGCTTG 19

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ATCCACCCGC AGCGAGAG 18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GCCACTGACC TCTCGCTG      18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CGCCCATGCG GTCGAAAC      18

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GCGAAGCAGA TTGCCAGCC      19

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

ACAGCCACCG AGCACGAC      18

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CAAACTGTCC TTCGCCGACC      20

( 2 ) INFORMATION FOR SEQ ID NO:22:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

CACCTACCAG CACCGTCATC 20

(2) INFORMATION FOR SEQ ID NO:23:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

TGCTCGACAA CGCGAACCTG 20

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

TCCGAGTTGG ACCCGAAGAC 20

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:25:

TACCAGGGCA AGGATGGCAG 20

(2) INFORMATION FOR SEQ ID NO:26:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:26:

GCAAACACCA GCACCCCG 18

(2) INFORMATION FOR SEQ ID NO:27:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: peptide ( i x ) FEATURE:
  ( A ) NAME/KEY: Modified-site
  ( B ) LOCATION: one-of(9, 10)
  ( D ) OTHER INFORMATION: /note= "Xaa=unknown."

( x i ) SEQUENCE DESCRIPTION: SEQ ID NO:27:

Asp Glu Thr Leu Ile Val Met Thr Xaa Xaa Leu Ile Val Met Leu Ile
1               5                   10                  15

Val Met Ser Thr Ala Gly Ser Ala Gly Leu Ile Val Met Ser Thr Ala
            20              25                  30

Gly His Ser Thr Ala Leu Ile Val Met Phe Tyr
            35              40

( 2 ) INFORMATION FOR SEQ ID NO:28:

( i ) SEQUENCE CHARACTERISTICS:
    ( A ) LENGTH: 26 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
  ( A ) NAME/KEY: Modified-site
  ( B ) LOCATION: one-of(5, 6, 7, 19, 23)
  ( D ) OTHER INFORMATION: /note= "Xaa=unknown."

( x i ) SEQUENCE DESCRIPTION: SEQ ID NO:28:

Ser Gly Ala Thr Xaa Xaa Xaa Leu Ile Val Met Ala Arg Leu Ile Val
1               5                   10                  15

Met Ala Xaa Phe Trp His Xaa Ser Ala Cys
            20              25

( 2 ) INFORMATION FOR SEQ ID NO:29:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
  ( A ) NAME/KEY: Modified-site
  ( B ) LOCATION: one-of(2, 3, 4, 5)
  ( D ) OTHER INFORMATION: /note= "Xaa=unknown."

( x i ) SEQUENCE DESCRIPTION: SEQ ID NO:29:

Gly Xaa Xaa Xaa Xaa Gly Lys Thr
1               5

( 2 ) INFORMATION FOR SEQ ID NO:30:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:30:

CAGGACGTCG AGGCGATCAC                                                                              20

( 2 ) INFORMATION FOR SEQ ID NO:31:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:31:

AACGACGACG TGGCCAGCGT 20

( 2 ) INFORMATION FOR SEQ ID NO:32:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:32:

CAGACGGTGT TTATGGGCGA 20

( 2 ) INFORMATION FOR SEQ ID NO:33:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

TCGGAGAAAC CGAAACGCTC 20

( 2 ) INFORMATION FOR SEQ ID NO:34:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

TCCTCGTCAG CGGTCAAGTA 20

( 2 ) INFORMATION FOR SEQ ID NO:35:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:35:

CTTCCCTATG ATGACTG 17

( 2 ) INFORMATION FOR SEQ ID NO:36:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear (  i  i  ) MOLECULE TYPE: DNA (genomic)

(  x  i  ) SEQUENCE DESCRIPTION: SEQ ID NO:36:

GGTGATCTGC TCACTGG                                                                       17

( 2 ) INFORMATION FOR SEQ ID NO:37:

(  i  ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:37:

GCCGCAGACG CTGATCA                                                                       17

( 2 ) INFORMATION FOR SEQ ID NO:38:

(  i  ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:38:

TTGACCGCTG ACGAGGA                                                                       17

( 2 ) INFORMATION FOR SEQ ID NO:39:

(  i  ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:39:

GCCAGCGTCG ATGGCCG                                                                       17

( 2 ) INFORMATION FOR SEQ ID NO:40:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:40:

CCCACCATTC AGCAGCTGGT                                                                    20

( 2 ) INFORMATION FOR SEQ ID NO:41:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:41:

GTCGAGCGAA CCGCGAATGA                                                                                              20

( 2 ) INFORMATION FOR SEQ ID NO:42:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

ATGACCATGA TTACGCCAAG CTTGCATGCC TGCAGGTCGA CTCTAGAGGA TCCCCATCCG    60
ACACTTCGCG ATCACATCCG TGATCACAGC CCGATAACAC CAACTCCTGG AAGGAATGCT   120
GTGCCCGAGC AACACCCACC CATTACAGAA ACCACCACCG GAGCCGCTAG CAACGGCTGT   180
CCCGTCGTGG GTCATATGAA ATACCCCGTC GAGGGCGGCG GAAACCAGGA CTGGTGGCCC   240
AACCGGCTCA ATCTGAAGGT ACTGCACCAA AACCCGGCCG TCGCTGACCC GATGGGTGCG   300
GCGTTCGACT ATGCCGCGGA GGTCGCGACC AGTCGACTTG ACGCCCTGAC GCGGGACATC   360

( 2 ) INFORMATION FOR SEQ ID NO:43:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

Met Thr Met Ile Thr Pro Ser Leu His Ala Cys Arg Ser Thr Leu Glu
  1               5                  10                  15

Asp Pro His Pro Thr Leu Arg Asp His Ile Arg Asp His Ser Pro Ile
             20                  25                  30

Thr Pro Thr Pro Gly Arg Asn Ala Met Pro Glu Gln His Pro Pro Ile
         35                  40                  45

Thr Glu Thr Thr Thr Gly Ala Ala Ser Asn Gly Cys Pro Val Val Gly
     50                  55                  60

His Met Lys Tyr Pro Val Glu Gly Gly Gly Asn Gln Asp Trp Trp Pro
 65                  70                  75                  80

Asn Arg Leu Asn Leu Lys Val Leu His Gln Asn Pro Ala Val Ala Asp
                 85                  90                  95

Pro Met Gly Ala Ala Phe Asp Tyr Ala Ala Glu Val Ala Thr Ser Arg
             100                 105                 110

Leu Asp Ala Leu Thr Arg Asp Ile
             115                 120

( 2 ) INFORMATION FOR SEQ ID NO:44:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

Met Ser Thr Ser Asp Asp Ile His Asn Thr Thr Ala Thr Gly Lys Cys
  1               5                  10                  15

|     |     |     |     |     |     |     |     |     |     |     |     |     |     |
| --- | --- | --- | --- | --- | --- | --- | --- | --- | --- | --- | --- | --- | --- |
| Pro | Phe | His | Gln | Gly | Gly | His | Asp | Gln | Ser | Ala | Gly | Ala | Gly | Thr | Thr |
|     |     |     | 20  |     |     |     |     | 25  |     |     |     |     | 30  |
| Thr | Arg | Asp | Trp | Trp | Pro | Asn | Gln | Leu | Arg | Val | Asp | Leu | Leu | Asn | Gln |
|     |     | 35  |     |     |     |     | 40  |     |     |     |     | 45  |
| His | Ser | Asn | Arg | Ser | Asn | Pro | Leu | Gly | Glu | Asp | Phe | Asp | Tyr | Arg | Lys |
|     |     | 50  |     |     |     | 55  |     |     |     |     | 60  |
| Glu | Phe | Ser | Lys | Leu | Asp | Tyr | Tyr | Gly | Leu | Lys | Lys | Asp | Leu |
| 65  |     |     |     |     | 70  |     |     |     |     | 75  |

( 2 ) INFORMATION FOR SEQ ID NO:45:

( i ) SEQUENCE CHARACTERISTICS:
        ( A ) LENGTH: 4795 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

```
GGTACCGTGA GGCGATGGGT GGCCCGGGGC CCGGCTGTCT GGTAAGCGCG GCCGCAAAAC      60
AGCTGTACTC TCGAATCCCA GTTAGTAACA ATGTGCTATG GAATCTCCAA TGACGAGCAC     120
ACTTCACCGA ACCCCATTAG CCACCGCGGG GCTGGCGCTC GTAGTGGCGC TGGGTGGCTG     180
CGGGGGCGGG GGCGGTGACA GTCGAGAGAC ACCGCCATAC GTGCCGAAAG CGACGACCGT     240
CGACGCAACA ACGCCGGCGC CGGCCGCCGA GCCACTGACG ATCGCCAGTC CATGTTCGC     300
CGACGGCGCC CCGATCCCGG TGCAATTCAG CTGCAAGGGG GCCAACGTGG CCGCCACCGT     360
TGACGTGGTC GTCGCCCGCG GCGAGCGAAC TGGCACTCGT CGTCGATGAC CCCGACGCGG     420
TCGGCGGACT GTACGTGCAC TGGATCGTGA CCGGAATCGC CCCTGGCTCT GGCAGCACGG     480
CGGATGGTCA GACTCCTGCT GGTGGGCACA GCGTGCCGAA TTCTGGTGGT CGGCAAGGAT     540
ACTTCGGTCC ATGCCCGCCG GCGGGCACCG GGACACACCA CTACCGGTTT ACCCTCTACC     600
ACCTTCCTGT CGCGCTCCAG CTGCCACCGG GAGCCACGGG AGTCCAAGCG GCACAGGCGA     660
TAGCACAGGC CGCCAGCGAC AGGCCCGGCT CGTCGGCACA TTCGAAGGCT GACGCCGCGG     720
CATCCCTGGC GAGGTGGTCG AAACCCTGGC TTCTCCAATT GCGCCTGGCG ACAATGATCA     780
ATATGGAATC GACAGTGGCG CACGCATTTC ACCGGTTCGC ACTGGCCATC TTGGGGCTGG     840
CGCTCCCCGT GGCGCTAGTT GCCTACGGTG GCAACGGTGA CAGTCGAAAG GCGGCGGCCG     900
TGGCGCCGAA AGCAGCAGCG CTCGGTCGGA GTATGCCCGA AACGCCTACC GGCGATGTAC     960
TGACAATCAG CAGTCCGGCA TTCGCCGACG GTGCGCCGAT CCCGGAACAG TACACCTGCA    1020
AAGGAGCCAA TATCGCGGCC TCCGTTGACC TGGTCGGCGC CGTTTGGCGG CGCACTCGTT    1080
GTCGATGATC CGGACCACCT CGCGAACCTT ACGTCCATTG GATCGTGATC GGGATCGCCC    1140
CTGGTGCTGG CAGCAGCCGA TGGTGAGACT CCCGGTGGCG GAATCAGCCT GCCGAACTCC    1200
AGCGGTCAGC CCGCATACAC CGGCCCCTGC CCGCCGGCGG GCACCGGGAC ACACCACTAC    1260
CGGTTTACCC TCTACCACCT TCCTGCCGTG CCTCCACTCG CGGGACTGGC TGGGACACAA    1320
GCGGCGCGGG TGATCGCGCA GGCCGCCACC ATGCAGGCCC GGCTCATCGG AACATACGAA    1380
GGCTGATCCA CCCGCCATCC CACGATCCAG CGGCCCCGGG CGATCGGGTC CTAGCAGACG    1440
CCTGTCACGC TAGCCAAAGT CTTGACTGAT TCCAGAAAAG GGAGTCATAT TGTCTAGTGT    1500
GTCCTCTATA CCGGACTACG CCGAACAGCT CCGGACGGCC GACCTGCGCG TGACCCGACC    1560
GCGCGTCGCC GTCCTGGAAG CAGTGAATGC GCATCCACAC GCCGACACGG AAACGATTTT    1620
CGGTGCCGTG CGTTTTGCGC TGCCCGACGT ATCCGGCAAG CCGTGTACGA CGTGCTGCAT    1680
```

```
GCCCTGACCG CCGCGGGCTT GGTGCGAAAG ATCCAACCCT CGGGCTCCGT CGCGCGCTAC  1740
GAGTCCAGGG TCGGCGACAA CCACCATCAC ATCGTCTGCC GGTCTTGCGG GGTTATCGCC  1800
GATGTCGACT GTGCTGTTGG CGAGGCACCC TGTCTGACGG CCTCGGACCA TAACGGCTTC  1860
CTGTTGGACG AGGCGGAGGT CATCTACTGG GGTCTATGTC CTGATTGTTC GATATCCGAC  1920
ACTTCGCGAT CACATCCGTG ATCACAGCCC GATAACACCA ACTCCTGGAA GGAATGCTGT  1980
GCCCGAGCAA CACCCACCCA TTACAGAAAC CACCACCGGA GCCGCTAGCA ACGGCTGTCC  2040
CGTCGTGGGT CATATGAAAT ACCCCGTCGA GGGCGGCGGA AACCAGGACT GGTGGCCCAA  2100
CCGGCTCAAT CTGAAGGTAC TGCACCAAAA CCCGGCCGTC GCTGACCCGA TGGGTGCGGC  2160
GTTCGACTAT GCCGCGGAGG TCGCGACCAG TCGACTTGAC GCCCTGACGC GGGACATCGA  2220
GGAAGTGATG ACCACCTCGC AGCCGTGGTG GCCCGCCGAC TACGGCCACT ACGGGCCGCT  2280
GTTTATCCGG ATGGCGTGGC ACGCTGCCGG CACCTACCGC ATCCACGACG GCCGCGGCGG  2340
CGCCGGGGGC GGCATGCAGC GGTTCGCGCC GCTTAACAGC TGGCCCGACA ACGCCAGCTT  2400
GGACAAGGCG CGCCGGCTGC TGTGGCCGGT CAAGAAGAAG TACGGCAAGA AGCTCTCATG  2460
GGCGGACCTG ATTGTTTTCG CCGGCAACCG CTGCGCTCGG AATCGATGGG CTTCAAGACG  2520
TTCGGGTTCG GCTTCGGGCG TCGACCAGTG GGAGACCGAT GAGGTCTATT GGGGCAAGGA  2580
AGCCACCTGG CTCGGCGATG ACGGTTACAG CGTAAGCGAT CTGGAGAACC CGCTGGCCGC  2640
GGTGCAGATG GGGCTGATCT ACGTGAACCC GGAGGCGCCG AACGGCAACC CGGACCCCAT  2700
GGCCGCGGCG GTCGACATTC GCGAGACGTT TCGGCGCATG GCCATGAACG ACGTCGAAAC  2760
AGCGGCGCTG ATCGTCGGCG GTCACACTTT CGGTAAGACC CATGGCGCCG GCCCGGCCGA  2820
TCTGGTCGGC CCCGAACCCG AGGCTGCTCC GCTGGAGCAG ATGGGCTTGG GCTGGAAGAG  2880
CTCGTATGGC ACCGGAACCG GTAAGGACGC GATCACCAGC GGCATCGAGG TCGTATGGAC  2940
GAACACCCCG ACGAAATGGG ACAACAGTTT CCTCGAGATC CTGTACGGCT ACGAGTGGGA  3000
GCTGACGAAG AGCCCTGCTG GCGCTTGGCA ATACACCGCC AAGGACGGCG CCGGTGCCGG  3060
CACCATCCCG GACCCGTTCG GCGGGCCAGG GCGCTCCCCG ACGATGCTGG CCACTGACCT  3120
CTCGCTGCGG GTGGATCCGA TCTATGAGCG GATCACGCGT CGCTGGCTGG AACACCCCGA  3180
GGAATTGGCC GACGAGTTCC GCAAGGCCTG GTACAAGCTG ATCCACCGAG ACATGGGTCC  3240
CGTTGCGAGA TACCTTGGGC CGCTGGTCCC CAAGCAGACC CTGCTGTGGC AGGATCCGGT  3300
CCCTGCGGTC AGCACGACCT CGTCGGCGAA GCAGATTGCC AGCCTTAAGA GCCAGATCCG  3360
GGCATCGGGA TTGACTGTCT CACAGCTAGT TTCGACCGCA TGGGCGGCGG CGTCGTCGTT  3420
CCGTGGTAGC GACAAGCGCG GCGGCGCCAA CGGTGGTCGC ATCCGCCTGC AGCCACAACT  3480
CGGGTGGGAG GTCAACGACC CCGACGGATC TGCGCAAGGT CATTCGCACC CTGAAGAGAT  3540
CCAGGAGTCA TTCACTCGGC GCGGGAACAT CAAAGTGTCC TTCGCCGACC TCGTCGTGCT  3600
CGGTGGCTGT GCGCCACTAG AGAAAGCAGC AAAGGCGGCT GGCCACAACA TCACGGTGCC  3660
CTTCACCCCG GGCCCGCACG ATGCGTCGCA GGAACAAACC GACGTGGAAT CCTTTGCCGT  3720
GCTGGAGCCC AAGGCAGATG GCTTCCGAAA CTACCTCGGA AAGGGCAACC GTTGCCGGCC  3780
GAGTACATCG CTGCTCGACA AGGCGAACCT GCTTACGCTC AGTGCCCCTG AGATGACGGT  3840
GCTGGTAGGT GGCCTGCGCG TCCTCGGCGC AAACTACAAG CGCTTACCGC TGGGCGTGTT  3900
CACCGAGGCC TCCGAGTCAC TGACCAACGA CTTCTTCGTG AACCTGCTCG ACATGGGTAT  3960
CACCTGGGAG CCCTCGCCAG CAGATGACGG GACCTACCAG GGCAAGGATG GCAGTGGCAA  4020
GGTGAAGTGG ACCGGCAGCC GCGTGGACCT GGTCTTCGGG TCCAACTCGG AGTTGCGGGC  4080
```

|  |  |  |  |  |  |  |
|---|---|---|---|---|---|---|
| GCTTGTCGAG | GTCTATGCGC | CGATGACGCG | GCAGGCGAAG | TTCGTGACAG | GATTCGTCGC | 4140 |
| TGCGTGGGAC | AAGGTGATGA | ACCTCGACAG | GTTCGACGTG | CGCTGATTCG | GGTTGATCGG | 4200 |
| CCCTGCCCGC | CGATCAACCA | CAACCCGCCG | CAGCACCCCG | CGAGCTGACC | GGCTCGCGGG | 4260 |
| GTGCTGGTGT | TTGCCCGGCG | CGATTTGTCA | GACCCCGCGT | GCATGGTGGT | CGCACGGACG | 4320 |
| CACGAGACGG | GGATGACGAG | ACGGGGATGA | GGAGAAAGGG | CGCCGAAATG | TGCTGGATGT | 4380 |
| GCGATCACCC | GGAAGCCACC | GCCGAGGAGT | ACCTCGACGA | GGTGTACGGG | ATAATGCTCA | 4440 |
| TGCATGGCTG | GGCGGTACAG | CACGTGGAGT | GCGAGCGACG | GCCATTTGCC | TACACGGTTG | 4500 |
| GTCTAACCCG | GCGCGGCTTG | CCCGAACTGG | TGGTGACTGG | CCTCTCGCCA | CGACGTGGGC | 4560 |
| AGCGGTTGTT | GAACATGCCG | TCGAGGGCTC | TGGTCGGTGA | CTTGCTGACT | CCCGGTATGT | 4620 |
| AGACCACCCT | CAAAGCCGGC | CCTCTTGTCG | AAACGGTCCA | GGCTACACAT | CCGGACGCGC | 4680 |
| ATTTGTATTG | TGCGATCGCC | ATCTTTGCGC | ACAAGGTGAC | GGCCTTGCAG | TTGGTGTGGG | 4740 |
| CCGACCGCGT | GGTCGCTGGC | CGTGGGCGGC | GGACTTCGAC | GAAGGTCGCG | GTACC | 4795 |

( 2 ) INFORMATION FOR SEQ ID NO:46:

( i ) SEQUENCE CHARACTERISTICS:
        ( A ) LENGTH: 700 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

|  |  |  |  |  |  |  |
|---|---|---|---|---|---|---|
| TTCGAAGGCT | GACGCCGCGG | CATCCCTGGC | GAGGTGGTCG | AAACCCTGGC | TTCTCCAATT | 60 |
| GCGCCTGGCG | ACAATGATCA | ATATGGAATC | GACAGTGGCG | CACGCATTTC | ACCGGTTCGC | 120 |
| ACTGGCCATC | TTGGGGCTGG | CGCTCCCCGT | GGCGCTAGTT | GCCTACGGTG | GCAACGGTGA | 180 |
| CAGTCGAAAG | GCGGCGGCCG | TGGCGCCGAA | AGCAGCAGCG | CTCGGTCGGA | GTATGCCCGA | 240 |
| AACGCCTACC | GGCGATGTAC | TGACAATCAG | CAGTCCGGCA | TTCGCCGACG | GTGCGCCGAT | 300 |
| CCCGGAACAG | TACACCTGCA | AAGGAGCCAA | TATCGCGGCC | TCCGTTGACC | TGGTCGGCGC | 360 |
| CGTTTGGCGG | CGCACTCGTT | GTCGATGATC | CGGACCACCT | CGCGAACCTT | ACGTCCATTG | 420 |
| GATCGTGATC | GGGATCGCCC | CTGGTGCTGG | CAGCAGCCGA | TGGTGAGACT | CCCGGTGGCG | 480 |
| GAATCAGCCT | GCCGAACTCC | AGCGGTCAGC | CCGCATACAC | CGGCCCTGC | CCGCCGGCGG | 540 |
| GCACCGGGAC | ACACCACTAC | CGGTTTACCC | TCTACCACCT | TCCTGCCGTG | CCTCCACTCG | 600 |
| CGGGACTGGC | TGGGACACAA | GCGGCGCGGG | TGATCGCGCA | GGCCGCCACC | ATGCAGGCCC | 660 |
| GGCTCATCGG | AACATACGAA | GGCTGATCCA | CCCGCCATCC |  |  | 700 |

( 2 ) INFORMATION FOR SEQ ID NO:47:

( i ) SEQUENCE CHARACTERISTICS:
        ( A ) LENGTH: 700 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

|  |  |  |  |  |  |  |
|---|---|---|---|---|---|---|
| GGTACCGTGA | GGCGATGGGT | GGCCCGGGGC | CCGGCTGTCT | GGTAAGCGCG | GCCGCAAAAC | 60 |
| AGCTGTACTC | TCGAATCCCA | GTTAGTAACA | ATGTGCTATG | GAATCTCCAA | TGACGAGCAC | 120 |
| ACTTCACCGA | ACCCCATTAG | CCACCGCGGG | GCTGGCGCTC | GTAGTGGCGC | TGGGTGGCTG | 180 |

| | | | | |
|---|---|---|---|---|
| CGGGGGCGGG | GGCGGTGACA | GTCGAGAGAC | ACCGCCATAC | GTGCCGAAAG | CGACGACCGT | 240 |
| CGACGCAACA | ACGCCGGCGC | CGGCCGCCGA | GCCACTGACG | ATCGCCAGTC | CCATGTTCGC | 300 |
| CGACGGCGCC | CCGATCCCGG | TGCAATTCAG | CTGCAAGGGG | GCCAACGTGG | CCGCCACCGT | 360 |
| TGACGTGGTC | GTCGCCCGCG | GCGAGCGAAC | TGGCACTCGT | CGTCGATGAC | CCCGACGCGG | 420 |
| TCGGCGGACT | GTACGTGCAC | TGGATCGTGA | CCGGAATCGC | CCCTGGCTCT | GGCAGCACGG | 480 |
| CGGATGGTCA | GACTCCTGCT | GGTGGGCACA | GCGTGCCGAA | TTCTGGTGGT | CGGCAAGGAT | 540 |
| ACTTCGGTCC | ATGCCCGCCG | GCGGGCACCG | GGACACACCA | CTACCGGTTT | ACCCTCTACC | 600 |
| ACCTTCCTGT | CGCGATCCAG | CTGCCACCGG | GAGCCACGGG | AGTCCAAGCG | GCACAGGCGA | 660 |
| TAGCACAGGC | CGCCAGCGAC | AGGCCCGGCT | CGTCGGCACA | | | 700 |

( 2 ) INFORMATION FOR SEQ ID NO:48:

( i ) SEQUENCE CHARACTERISTICS:
        ( A ) LENGTH: 735 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Met Pro Glu Gln His Pro Pro Ile Thr Glu Thr Thr Thr Gly Ala Ala
 1               5                  10                  15
Ser Asn Gly Cys Pro Val Val Gly His Met Lys Tyr Pro Val Glu Gly
            20                  25                  30
Gly Gly Asn Gln Asp Trp Trp Pro Asn Arg Leu Asn Leu Lys Val Leu
        35                  40                  45
His Gln Asn Pro Ala Val Ala Asp Pro Met Gly Ala Ala Phe Asp Tyr
    50                  55                  60
Ala Ala Glu Val Ala Thr Ser Arg Leu Asp Ala Leu Thr Arg Asp Ile
65                  70                  75                  80
Glu Glu Val Met Thr Thr Ser Gln Pro Trp Trp Pro Ala Asp Tyr Gly
                85                  90                  95
His Tyr Gly Pro Leu Phe Ile Arg Met Ala Trp His Ala Ala Gly Thr
            100                 105                 110
Tyr Arg Ile His Asp Gly Arg Gly Gly Ala Gly Gly Gly Met Gln Arg
        115                 120                 125
Phe Ala Pro Leu Asn Ser Trp Pro Asp Asn Ala Ser Leu Asp Lys Ala
    130                 135                 140
Arg Arg Leu Leu Trp Pro Val Lys Lys Tyr Gly Lys Lys Leu Ser
145                 150                 155                 160
Trp Ala Asp Leu Ile Val Phe Ala Gly Asn Arg Cys Ala Arg Asn Arg
                165                 170                 175
Trp Ala Ser Arg Arg Ser Gly Ser Ala Ser Gly Val Asp Gln Trp Glu
            180                 185                 190
Thr Asp Glu Val Tyr Trp Gly Lys Glu Ala Thr Trp Leu Gly Asp Asp
        195                 200                 205
Gly Tyr Ser Val Ser Asp Leu Glu Asn Pro Leu Ala Ala Val Gln Met
    210                 215                 220
Gly Leu Ile Tyr Val Asn Pro Glu Ala Pro Asn Gly Asn Pro Asp Pro
225                 230                 235                 240
Met Ala Ala Ala Val Asp Ile Arg Glu Thr Phe Arg Arg Met Ala Met
                245                 250                 255
```

-continued

| | | | | | | | | | | | | | |
|---|---|---|---|---|---|---|---|---|---|---|---|---|---|
| Asn | Asp | Val | Glu 260 | Thr | Ala | Ala | Leu | Ile 265 | Val | Gly | Gly | His | Thr | Phe 270 | Gly |
| Lys | Thr | His 275 | Gly | Ala | Gly | Pro | Ala 280 | Asp | Leu | Val | Gly | Pro 285 | Glu | Pro | Glu |
| Ala | Ala 290 | Pro | Leu | Glu | Gln | Met 295 | Gly | Leu | Gly | Trp | Lys 300 | Ser | Ser | Tyr | Gly |
| Thr 305 | Gly | Thr | Gly | Lys | Asp 310 | Ala | Ile | Thr | Ser | Gly 315 | Ile | Glu | Val | Val | Trp 320 |
| Thr | Asn | Thr | Pro | Thr 325 | Lys | Trp | Asp | Asn | Ser 330 | Phe | Leu | Glu | Ile | Leu 335 | Tyr |
| Gly | Tyr | Glu | Trp 340 | Glu | Leu | Thr | Lys | Ser 345 | Pro | Ala | Gly | Ala | Trp 350 | Gln | Tyr |
| Thr | Ala | Lys 355 | Asp | Gly | Ala | Gly | Ala 360 | Gly | Thr | Ile | Pro | Asp 365 | Pro | Phe | Gly |
| Gly | Pro 370 | Gly | Arg | Ser | Pro | Thr 375 | Met | Leu | Ala | Thr | Asp 380 | Leu | Ser | Leu | Arg |
| Val 385 | Asp | Pro | Ile | Tyr | Glu 390 | Arg | Ile | Thr | Arg | Arg 395 | Trp | Leu | Glu | His | Pro 400 |
| Glu | Glu | Leu | Ala | Asp 405 | Glu | Phe | Arg | Lys | Ala 410 | Trp | Tyr | Lys | Leu | Ile 415 | His |
| Arg | Asp | Met | Gly 420 | Pro | Val | Ala | Arg | Tyr 425 | Leu | Gly | Pro | Leu | Val 430 | Pro | Lys |
| Gln | Thr | Leu 435 | Leu | Trp | Gln | Asp | Pro 440 | Val | Pro | Ala | Val | Ser 445 | Thr | Thr | Ser |
| Ser | Ala 450 | Lys | Gln | Ile | Ala | Ser 455 | Leu | Lys | Ser | Gln | Ile 460 | Arg | Ala | Ser | Gly |
| Leu 465 | Thr | Val | Ser | Gln | Leu 470 | Val | Ser | Thr | Ala | Trp 475 | Ala | Ala | Ala | Ser | Ser 480 |
| Phe | Arg | Gly | Ser | Asp 485 | Lys | Arg | Gly | Gly | Ala 490 | Asn | Gly | Gly | Arg | Ile 495 | Arg |
| Leu | Gln | Pro | Gln | Val 500 | Gly | Trp | Glu | Val 505 | Asn | Asp | Pro | Asp | Gly 510 | Ser | Ala |
| Gln | Gly | His 515 | Ser | His | Pro | Glu | Glu 520 | Ile | Gln | Glu | Ser | Phe 525 | Thr | Arg | Arg |
| Gly | Asn | Ile | Lys 530 | Val | Ser | Phe 535 | Ala | Asp | Leu | Val | Val 540 | Leu | Gly | Gly | Cys |
| Ala 545 | Pro | Leu | Glu | Lys | Ala 550 | Ala | Lys | Ala | Ala | Gly 555 | His | Asn | Ile | Thr | Val 560 |
| Pro | Phe | Thr | Pro | Gly 565 | Pro | His | Asp | Ala | Ser 570 | Gln | Glu | Gln | Thr | Asp 575 | Val |
| Glu | Ser | Phe | Ala 580 | Val | Leu | Glu | Pro | Lys 585 | Ala | Asp | Gly | Phe | Arg 590 | Asn | Tyr |
| Leu | Gly | Lys 595 | Gly | Asn | Arg | Cys | Arg 600 | Pro | Ser | Thr | Ser | Leu 605 | Leu | Asp | Lys |
| Ala | Asn 610 | Leu | Leu | Thr | Leu | Ser 615 | Ala | Pro | Glu | Met | Thr 620 | Val | Leu | Val | Gly |
| Gly 625 | Leu | Arg | Val | Leu | Gly 630 | Ala | Asn | Tyr | Lys | Arg 635 | Leu | Pro | Leu | Gly | Val 640 |
| Phe | Thr | Glu | Ala | Ser 645 | Glu | Ser | Leu | Thr | Asn 650 | Asp | Phe | Phe | Val | Asn 655 | Leu |
| Leu | Asp | Met | Gly 660 | Ile | Thr | Trp | Glu | Pro 665 | Ser | Pro | Ala | Asp | Gly 670 | Thr |
| Tyr | Gln | Gly 675 | Lys | Asp | Gly | Ser | Gly 680 | Lys | Val | Lys | Trp | Thr 685 | Gly | Ser | Arg |

|     |     |     |     |     |     |     |     |     |     |     |     |     |     |     |
|-----|-----|-----|-----|-----|-----|-----|-----|-----|-----|-----|-----|-----|-----|-----|
| Val | Asp | Leu | Val | Phe | Gly | Ser | Asn | Ser | Glu | Leu | Arg | Ala | Leu | Val | Glu |
| 690 |     |     |     |     | 695 |     |     |     |     | 700 |     |     |     |     |
| Val | Tyr | Ala | Pro | Met | Thr | Arg | Gln | Ala | Lys | Phe | Val | Thr | Gly | Phe | Val |
| 705 |     |     |     |     | 710 |     |     |     |     | 715 |     |     |     |     | 720 |
| Ala | Ala | Trp | Asp | Lys | Val | Met | Asn | Leu | Asp | Arg | Phe | Asp | Val | Arg |
|     |     |     |     | 725 |     |     |     |     | 730 |     |     |     |     | 735 |

( 2 ) INFORMATION FOR SEQ ID NO:49:

( i ) SEQUENCE CHARACTERISTICS:
        ( A ) LENGTH: 726 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

| Met | Ser | Thr | Ser | Asp | Ile | His | Asn | Thr | Ala | Thr | Gly | Lys | Cys |
|-----|-----|-----|-----|-----|-----|-----|-----|-----|-----|-----|-----|-----|-----|
| 1   |     |     |     | 5   |     |     |     | 10  |     |     |     |     | 15  |
| Pro | Phe | His | Gln | Gly | Gly | His | Asp | Gln | Ser | Ala | Gly | Ala | Gly | Thr | Thr |
|     |     |     | 20  |     |     |     |     | 25  |     |     |     |     | 30  |     |     |
| Thr | Arg | Asp | Trp | Trp | Pro | Asn | Gln | Leu | Arg | Val | Asp | Leu | Leu | Asn | Gln |
|     |     | 35  |     |     |     |     | 40  |     |     |     |     | 45  |     |     |     |
| His | Ser | Asn | Arg | Ser | Asn | Pro | Leu | Gly | Glu | Asp | Phe | Asp | Tyr | Arg | Lys |
|     | 50  |     |     |     |     | 55  |     |     |     |     | 60  |     |     |     |     |
| Glu | Phe | Ser | Lys | Leu | Asp | Tyr | Tyr | Gly | Leu | Lys | Lys | Asp | Leu | Lys | Ala |
| 65  |     |     |     |     | 70  |     |     |     |     | 75  |     |     |     |     | 80  |
| Leu | Leu | Thr | Glu | Ser | Gln | Pro | Trp | Trp | Pro | Ala | Asp | Trp | Gly | Ser | Tyr |
|     |     |     |     | 85  |     |     |     |     | 90  |     |     |     |     | 95  |
| Ala | Gly | Leu | Phe | Ile | Arg | Met | Ala | Trp | His | Gly | Ala | Gly | Thr | Tyr | Arg |
|     |     |     | 100 |     |     |     |     | 105 |     |     |     |     | 110 |     |     |
| Ser | Ile | Asp | Gly | Arg | Gly | Gly | Ala | Gly | Arg | Gly | Gln | Gln | Arg | Phe | Ala |
|     |     |     | 115 |     |     |     |     | 120 |     |     |     |     | 125 |     |     |
| Pro | Leu | Asn | Ser | Trp | Pro | Asp | Asn | Val | Ser | Leu | Asp | Lys | Ala | Arg | Arg |
|     | 130 |     |     |     |     | 135 |     |     |     |     | 140 |     |     |     |     |
| Leu | Leu | Trp | Pro | Ile | Lys | Gln | Lys | Tyr | Gly | Gln | Lys | Ile | Ser | Trp | Ala |
| 145 |     |     |     |     | 150 |     |     |     |     | 155 |     |     |     |     | 160 |
| Asp | Leu | Phe | Ile | Leu | Ala | Gly | Asn | Val | Ala | Leu | Glu | Asn | Ser | Gly | Phe |
|     |     |     |     | 165 |     |     |     |     | 170 |     |     |     |     | 175 |
| Arg | Thr | Phe | Gly | Phe | Gly | Ala | Gly | Arg | Glu | Asp | Val | Trp | Glu | Pro | Asp |
|     |     |     | 180 |     |     |     |     | 185 |     |     |     |     | 190 |     |     |
| Leu | Asp | Val | Asn | Trp | Gly | Asp | Glu | Lys | Ala | Trp | Leu | Thr | His | Arg | His |
|     |     | 195 |     |     |     |     | 200 |     |     |     |     | 205 |     |     |     |
| Pro | Glu | Ala | Leu | Ala | Lys | Ala | Pro | Leu | Gly | Ala | Thr | Glu | Met | Gly | Leu |
|     | 210 |     |     |     |     | 215 |     |     |     |     | 220 |     |     |     |     |
| Ile | Tyr | Val | Asn | Pro | Glu | Gly | Pro | Asp | His | Ser | Gly | Glu | Pro | Leu | Ser |
| 225 |     |     |     |     | 230 |     |     |     |     | 235 |     |     |     |     | 240 |
| Ala | Ala | Ala | Ala | Ile | Arg | Ala | Thr | Phe | Gly | Asn | Met | Gly | Met | Asn | Asp |
|     |     |     |     | 245 |     |     |     |     | 250 |     |     |     |     | 255 |
| Glu | Glu | Thr | Val | Ala | Leu | Ile | Ala | Gly | Gly | His | Thr | Leu | Gly | Lys | Thr |
|     |     |     | 260 |     |     |     |     | 265 |     |     |     |     | 270 |     |
| His | Gly | Ala | Gly | Pro | Thr | Ser | Asn | Val | Gly | Pro | Asp | Pro | Glu | Ala | Ala |
|     |     |     | 275 |     |     |     |     | 280 |     |     |     |     | 285 |     |     |
| Pro | Ile | Glu | Glu | Gln | Gly | Leu | Gly | Trp | Ala | Ser | Thr | Tyr | Gly | Ser | Gly |
|     |     |     | 290 |     |     |     |     | 295 |     |     |     |     | 300 |     |     |

-continued

| | | | | | | | | | | | | | | |
|---|---|---|---|---|---|---|---|---|---|---|---|---|---|---|
| Val | Gly | Ala | Asp | Ala | Ile | Thr | Ser | Gly | Leu | Glu | Val | Val | Trp | Thr | Gln |
| 305 | | | | 310 | | | | 315 | | | | | | 320 |
| Thr | Pro | Thr | Gln | Trp | Ser | Asn | Tyr | Phe | Phe | Glu | Asn | Leu | Phe | Lys | Tyr |
| | | | | 325 | | | | 330 | | | | | 335 | |
| Glu | Trp | Val | Gln | Thr | Arg | Ser | Pro | Ala | Gly | Ala | Ile | Gln | Phe | Glu | Ala |
| | | | 340 | | | | 345 | | | | | 350 | | | |
| Val | Asp | Ala | Pro | Glu | Ile | Ile | Pro | Asp | Pro | Phe | Asp | Pro | Ser | Lys | Lys |
| | | 355 | | | | 360 | | | | 365 | | | | | |
| Arg | Lys | Pro | Thr | Met | Leu | Val | Thr | Asp | Leu | Thr | Leu | Arg | Phe | Asp | Pro |
| | 370 | | | | 375 | | | | 380 | | | | | | |
| Glu | Phe | Glu | Lys | Ile | Ser | Arg | Arg | Phe | Leu | Asn | Asp | Pro | Gln | Ala | Phe |
| 385 | | | | 390 | | | | 395 | | | | | 400 | | |
| Asn | Glu | Ala | Phe | Ala | Arg | Ala | Trp | Phe | Lys | Leu | Thr | His | Arg | Asp | Met |
| | | | | 405 | | | | 410 | | | | 415 | | | |
| Gly | Pro | Lys | Ser | Arg | Tyr | Ile | Gly | Pro | Glu | Val | Pro | Lys | Glu | Asp | Leu |
| | | | 420 | | | | 425 | | | | | 430 | | | |
| Ile | Trp | Gln | Asp | Pro | Leu | Pro | Gln | Pro | Ile | Tyr | Asn | Pro | Thr | Glu | Gln |
| | | | 435 | | | | 440 | | | | 445 | | | | |
| Asp | Ile | Ile | Asp | Leu | Lys | Phe | Ala | Ile | Ala | Asp | Ser | Gly | Leu | Ser | Val |
| | 450 | | | | | 455 | | | | 460 | | | | | |
| Ser | Glu | Leu | Val | Ser | Val | Ala | Trp | Ala | Ser | Ala | Ser | Thr | Phe | Arg | Gly |
| 465 | | | | | 470 | | | | | 475 | | | | | 480 |
| Gly | Asp | Lys | Arg | Gly | Gly | Ala | Asn | Gly | Ala | Arg | Leu | Ala | Leu | Met | Pro |
| | | | | 485 | | | | | 490 | | | | | 495 | |
| Gln | Arg | Asp | Trp | Asp | Val | Asn | Ala | Ala | Ala | Val | Arg | Ala | Leu | Pro | Val |
| | | | | 500 | | | | 505 | | | | | 510 | | |
| Leu | Glu | Lys | Ile | Gln | Lys | Glu | Ser | Gly | Lys | Ala | Ser | Leu | Ala | Asp | Ile |
| | | | 515 | | | | 520 | | | | | 525 | | | |
| Ile | Val | Leu | Ala | Gly | Val | Val | Gly | Val | Glu | Lys | Ala | Ala | Ser | Ala | Ala |
| | 530 | | | | | 535 | | | | | 540 | | | | |
| Gly | Leu | Ser | Ile | His | Val | Pro | Phe | Ala | Pro | Gly | Arg | Val | Asp | Ala | Arg |
| 545 | | | | | 550 | | | | | 555 | | | | | 560 |
| Gln | Asp | Gln | Thr | Asp | Ile | Glu | Met | Phe | Glu | Leu | Leu | Glu | Pro | Ile | Ala |
| | | | | 565 | | | | 570 | | | | | | 575 | |
| Asp | Gly | Phe | Arg | Asn | Tyr | Arg | Ala | Arg | Leu | Asp | Val | Ser | Thr | Thr | Glu |
| | | | | 580 | | | | 585 | | | | | 590 | | |
| Ser | Leu | Leu | Ile | Asp | Lys | Ala | Gln | Gln | Leu | Thr | Leu | Thr | Ala | Pro | Glu |
| | | | | 595 | | | | 600 | | | | | 605 | | |
| Met | Thr | Ala | Leu | Val | Gly | Gly | Met | Arg | Val | Leu | Gly | Gly | Asn | Phe | Asp |
| | | 610 | | | | 615 | | | | | 620 | | | | |
| Gly | Ser | Lys | Asn | Gly | Val | Phe | Thr | Asp | Arg | Val | Gly | Val | Leu | Ser | Asn |
| 625 | | | | | 630 | | | | | 635 | | | | | 640 |
| Asp | Phe | Phe | Val | Asn | Leu | Leu | Asp | Met | Arg | Tyr | Glu | Trp | Lys | Ala | Thr |
| | | | | 645 | | | | 650 | | | | | | 655 | |
| Asp | Glu | Ser | Lys | Glu | Leu | Phe | Glu | Gly | Arg | Asp | Arg | Glu | Thr | Gly | Glu |
| | | | | 660 | | | | 665 | | | | | 670 | | |
| Val | Lys | Phe | Thr | Ala | Ser | Arg | Ala | Asp | Leu | Val | Phe | Gly | Ser | Asn | Ser |
| | | | 675 | | | | 680 | | | | | 685 | | | |
| Val | Leu | Arg | Ala | Val | Ala | Glu | Val | Tyr | Ala | Ser | Ser | Asp | Ala | His | Glu |
| | | 690 | | | | | 695 | | | | | 700 | | | |
| Lys | Phe | Val | Lys | Asp | Phe | Val | Ala | Ala | Trp | Val | Lys | Val | Met | Asn | Leu |
| 705 | | | | | 710 | | | | | 715 | | | | | 720 |
| Asp | Arg | Phe | Asp | Leu | Leu | | | | | | | | | | |
| | | | | 725 | | | | | | | | | | | |

( 2 ) INFORMATION FOR SEQ ID NO:50:

( i ) SEQUENCE CHARACTERISTICS:
        ( A ) LENGTH: 729 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
Met Ser Thr Thr Asp Asp Thr His Asn Thr Leu Ser Thr Gly Lys Cys
 1               5                  10                  15

Pro Phe His Gln Gly Gly His Asp Arg Ser Ala Gly Ala Gly Thr Ala
                20                  25                  30

Ser Arg Asp Trp Trp Pro Asn Gln Leu Arg Val Asp Leu Leu Asn Gln
            35                  40                  45

His Ser Asn Arg Ser Asn Pro Leu Gly Glu Asp Phe Asp Tyr Arg Lys
        50                  55                  60

Glu Phe Ser Lys Leu Asp Tyr Tyr Ser Ala Leu Lys Gly Asp Leu Lys
65                  70                  75                  80

Ala Leu Leu Thr Asp Ser Gln Pro Trp Trp Pro Ala Asp Trp Gly Ser
                85                  90                  95

Tyr Val Gly Leu Phe Ile Arg Met Ala Trp His Gly Ala Gly Thr Tyr
                100                 105                 110

Arg Ser Ile Asp Gly Arg Gly Ala Gly Arg Gly Gln Gln Arg Phe
            115                 120                 125

Ala Pro Leu Asn Ser Trp Pro Asp Thr Val Ser Leu Asp Lys Ala Arg
130                 135                 140

Arg Leu Leu Trp Pro Ile Lys Gln Lys Tyr Gly Gln Lys Ile Ser Trp
145                 150                 155                 160

Ala Asp Leu Phe Ile Leu Ala Gly Asn Val Ala Leu Glu Asn Ser Gly
                165                 170                 175

Phe Arg Thr Phe Gly Phe Gly Ala Gly Arg Glu Asp Val Trp Glu Pro
                180                 185                 190

Asp Leu Asp Val Asn Trp Gly Asp Glu Lys Ala Trp Leu Thr His Arg
            195                 200                 205

His Pro Glu Ala Leu Ala Lys Ala Pro Leu Gly Ala Thr Glu Met Asp
        210                 215                 220

Leu Ile Tyr Val Thr Pro Glu Gly Pro Asn His Ser Gly Glu Pro Leu
225                 230                 235                 240

Ser Ala Ala Ala Ala Ile Arg Ala Thr Phe Gly Asn Met Gly Met Asn
                245                 250                 255

Asp Glu Glu Thr Val Ala Leu Ile Ala Gly Gly His Thr Leu Gly Lys
                260                 265                 270

Thr His Gly Pro Ala Ala Ala Ser His Val Gly Ala Asp Pro Glu Ala
            275                 280                 285

Ala Pro Ile Glu Ala Gln Gly Leu Gly Trp Ala Ser Ser Tyr Gly Ser
        290                 295                 300

Gly Val Gly Ala Asp Ala Ile Thr Ser Gly Leu Glu Val Val Trp Thr
305                 310                 315                 320

Gln Thr Pro Thr Gln Trp Ser Asn Tyr Phe Phe Glu Asn Leu Phe Lys
                325                 330                 335

Tyr Glu Trp Val Gln Thr Arg Ser Pro Ala Gly Ala Ile Gln Phe Glu
                340                 345                 350
```

| | | | | | | | | | | | | | | |
|---|---|---|---|---|---|---|---|---|---|---|---|---|---|---|
|Ala|Val|Asp 355|Ala|Pro|Asp|Ile|Ile 360|Pro|Asp|Pro|Phe|Asp 365|Pro|Ser|Lys|
|Lys|Arg 370|Xaa|Xaa|Lys|Pro|Thr 375|Met|Leu|Val|Thr|Asp 380|Leu|Thr|Leu|Arg|
|Phe 385|Asp|Pro|Glu|Phe|Lys 390|Ile|Ser|Arg|Arg 395|Phe|Leu|Asn|Asp|Pro 400||
|Gln|Ala|Phe|Asn|Glu 405|Ala|Phe|Ala|Arg|Ala 410|Trp|Phe|Lys|Leu|Thr 415|His|
|Arg|Asp|Met|Gly 420|Pro|Lys|Ala|Arg|Tyr 425|Ile|Gly|Pro|Glu|Val 430|Pro|Lys|
|Glu|Asp|Leu|Ile 435|Trp|Gln|Asp|Pro 440|Leu|Pro|Gln|Pro|Leu 445|Tyr|Gln|Pro|
|Thr|Gln 450|Glu|Asp|Ile|Ile|Asn 455|Leu|Lys|Ala|Ala|Ile 460|Ala|Ala|Ser|Gly|
|Leu 465|Ser|Ile|Ser|Glu|Met 470|Val|Ser|Val|Ala|Trp 475|Ala|Ser|Ala|Ser|Thr 480|
|Phe|Arg|Gly|Gly|Asp 485|Lys|Arg|Gly|Gly|Ala 490|Asn|Gly|Ala|Arg|Leu 495|Ala|
|Leu|Ala|Pro|Gln 500|Arg|Asp|Trp|Asp|Val 505|Asn|Ala|Val|Ala|Arg 510|Val||
|Leu|Pro|Val 515|Leu|Glu|Glu|Ile|Gln 520|Lys|Thr|Thr|Asn|Lys 525|Ala|Ser|Leu|
|Ala|Asp 530|Ile|Ile|Val|Leu|Ala 535|Gly|Val|Val|Gly|Ile 540|Glu|Gln|Ala|Ala|
|Ala|Ala|Ala 545|Arg|Val|Ser|Ile 550|His|Val|Pro|Phe 555|Pro|Pro|Gly|Arg|Val 560|
|Asp|Ala|Arg|His|Asp 565|Gln|Thr|Asp|Ile|Glu 570|Met|Phe|Ser|Leu|Leu 575|Glu|
|Pro|Ile|Ala|Asp 580|Gly|Phe|Arg|Asn|Tyr 585|Arg|Ala|Arg|Leu|Asp 590|Val|Ser|
|Thr|Thr|Glu 595|Ser|Leu|Leu|Ile|Asp 600|Lys|Ala|Gln|Gln|Leu 605|Thr|Leu|Thr|
|Ala|Pro 610|Glu|Met|Thr|Val|Leu 615|Val|Gly|Gly|Met|Arg 620|Val|Leu|Gly|Thr|
|Asn 625|Phe|Asp|Gly|Ser|Gln 630|Asn|Gly|Val|Phe|Thr 635|Asp|Lys|Pro|Gly|Val 640|
|Leu|Ser|Thr|Asp|Phe 645|Phe|Ala|Asn|Leu|Leu 650|Asp|Met|Arg|Tyr|Glu 655|Trp|
|Lys|Pro|Thr|Asp 660|Asp|Ala|Asn|Glu|Leu 665|Phe|Glu|Gly|Arg|Asp 670|Arg|Leu|
|Thr|Gly|Glu 675|Val|Lys|Tyr|Thr|Ala 680|Thr|Arg|Ala|Asp|Leu 685|Val|Phe|Gly|
|Ser|Asn 690|Ser|Val|Leu|Arg|Ala 695|Leu|Ala|Glu|Val|Tyr 700|Ala|Cys|Ser|Asp|
|Ala 705|His|Glu|Lys|Phe|Val 710|Lys|Asp|Phe|Val|Ala 715|Ala|Trp|Val|Lys|Val 720|
|Met|Asn|Leu|Asp|Arg 725|Phe|Asp|Leu|Gln| | | | | | | |

( 2 ) INFORMATION FOR SEQ ID NO:51:

( i ) SEQUENCE CHARACTERISTICS:
        ( A ) LENGTH: 731 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

| Met | Glu | Asn | Gln | Asn | Arg | Gln | Asn | Ala | Ala | Gln | Cys | Pro | Phe | His | Glu |
| 1 | | | | 5 | | | | | 10 | | | | | 15 | |

| Ser | Val | Thr | Asn | Gln | Ser | Ser | Asn | Arg | Thr | Thr | Asn | Lys | Asp | Trp | Trp |
| | | | 20 | | | | | 25 | | | | | 30 | | |

| Pro | Asn | Gln | Leu | Asn | Leu | Ser | Ile | Leu | His | Gln | His | Asp | Arg | Lys | Thr |
| | | | 35 | | | | | 40 | | | | | 45 | | |

| Asn | Pro | His | Asp | Glu | Glu | Phe | Asn | Tyr | Ala | Glu | Glu | Phe | Gln | Lys | Leu |
| | | 50 | | | | | 55 | | | | | 60 | | | |

| Asp | Tyr | Trp | Ala | Leu | Lys | Glu | Asp | Leu | Arg | Lys | Leu | Met | Thr | Glu | Ser |
| 65 | | | | | 70 | | | | | 75 | | | | | 80 |

| Gln | Asp | Trp | Trp | Pro | Ala | Asp | Tyr | Gly | His | Tyr | Gly | Pro | Leu | Phe | Ile |
| | | | | 85 | | | | | 90 | | | | | 95 | |

| Arg | Met | Ala | Trp | His | Ser | Ala | Gly | Thr | Tyr | Arg | Ile | Gly | Asp | Gly | Arg |
| | | | 100 | | | | | 105 | | | | | 110 | | |

| Gly | Gly | Ala | Ser | Thr | Gly | Thr | Gln | Arg | Phe | Ala | Pro | Leu | Asn | Ser | Trp |
| | | | 115 | | | | | 120 | | | | | 125 | | |

| Pro | Asp | Asn | Ala | Asn | Leu | Asp | Lys | Ala | Arg | Arg | Cys | Tyr | Gly | Arg | Ser |
| | | 130 | | | | | 135 | | | | | 140 | | | |

| Lys | Arg | Asn | Thr | Gly | Thr | Lys | Ser | Leu | Gly | Pro | Ile | Cys | Ser | Phe | Trp |
| 145 | | | | | 150 | | | | | 155 | | | | | 160 |

| Arg | Ala | Met | Ser | Leu | Leu | Asn | Arg | Trp | Val | Glu | Lys | Arg | Leu | Asp | Ser |
| | | | | 165 | | | | | 170 | | | | | 175 | |

| Ala | Ala | Gly | Pro | Leu | Thr | Ser | Gly | Ile | Arg | Lys | Lys | Thr | Phe | Ile | Gly |
| | | | 180 | | | | | 185 | | | | | 190 | | |

| Asp | Arg | Lys | Lys | Ser | Gly | Ser | Pro | Leu | Asn | Ala | Ile | Pro | Val | Ile | Ala |
| | | 195 | | | | | 200 | | | | | 205 | | | |

| Ser | Ser | Lys | Thr | Arg | Ser | Pro | Arg | Ala | Asn | Gly | Val | Asn | Leu | Arg | Gln |
| 210 | | | | | 215 | | | | | 220 | | | | | |

| Pro | Arg | Arg | Ala | Gly | Arg | Gln | Ala | Gly | Ser | Lys | Ser | Arg | Gly | Ile | Ser |
| 225 | | | | | 230 | | | | | 235 | | | | | 240 |

| Ala | Glu | Thr | Phe | Arg | Arg | Met | Gly | Met | Asn | Asp | Glu | Glu | Thr | Val | Ala |
| | | | | 245 | | | | | 250 | | | | | 255 | |

| Leu | Ile | Ala | Gly | Gly | His | Thr | Phe | Gly | Lys | Ala | His | Arg | Gly | Gly | Pro |
| | | | 260 | | | | | 265 | | | | | 270 | | |

| Ala | Thr | His | Val | Gly | Pro | Glu | Pro | Glu | Ala | Ala | Pro | Ile | Glu | Ala | Gln |
| | | 275 | | | | | 280 | | | | | 285 | | | |

| Gly | Leu | Gly | Trp | Ile | Ser | Ser | Tyr | Gly | Lys | Gly | Lys | Gly | Ser | Asp | Thr |
| | 290 | | | | | 295 | | | | | 300 | | | | |

| Ile | Thr | Ser | Gly | Ile | Glu | Gly | Ala | Trp | Thr | Pro | Thr | Pro | Thr | Gln | Trp |
| 305 | | | | | 310 | | | | | 315 | | | | | 320 |

| Asp | Thr | Ser | Tyr | Phe | Asp | Met | Leu | Phe | Gly | Tyr | Asp | Trp | Trp | Leu | Thr |
| | | | | 325 | | | | | 330 | | | | | 335 | |

| Lys | Ser | Pro | Ala | Gly | Ala | Trp | Gln | Trp | Met | Ala | Val | Asp | Pro | Asp | Glu |
| | | | 340 | | | | | 345 | | | | | 350 | | |

| Lys | Asp | Leu | Ala | Pro | Asp | Ala | Glu | Asp | Pro | Ser | Lys | Lys | Val | Pro | Thr |
| | | | 355 | | | | | 360 | | | | | 365 | | |

| Met | Met | Met | Thr | Thr | Asp | Leu | Ala | Leu | Arg | Phe | Asp | Pro | Glu | Tyr | Glu |
| | | | 370 | | | | | 375 | | | | | 380 | | |

| Lys | Ile | Ala | Arg | Arg | Phe | His | Gln | Asn | Pro | Glu | Glu | Phe | Ala | Glu | Ala |
| 385 | | | | | 390 | | | | | 395 | | | | | 400 |

| | | | | | | | | | | | | | | |
|---|---|---|---|---|---|---|---|---|---|---|---|---|---|---|
| Phe | Ala | Arg | Ala | Trp<br>405 | Phe | Lys | Leu | Thr | His<br>410 | Arg | Asp | Met | Gly | Pro<br>415 | Lys |
| Thr | Arg | Tyr | Leu<br>420 | Gly | Pro | Glu | Val<br>425 | Pro | Lys | Glu | Asp | Phe | Ile<br>430 | Trp | Gln |
| Asp | Pro | Ile<br>435 | Pro | Glu | Val | Asp | Tyr<br>440 | Glu | Leu | Thr | Glu | Ala<br>445 | Glu | Ile | Glu |
| Glu | Ile<br>450 | Lys | Ala | Lys | Ile | Leu<br>455 | Asn | Ser | Gly | Leu | Thr<br>460 | Val | Ser | Glu | Leu |
| Val<br>465 | Lys | Thr | Ala | Trp | Ala<br>470 | Ser | Ala | Ala | Arg | Ser<br>475 | Ala | Thr | Arg | Ile | Ser<br>480 |
| Ala | Ala | Thr | Asn | Gly<br>485 | Arg | Arg | Ile | Arg | Leu<br>490 | Ala | Pro | Gln | Lys | Asp<br>495 | Trp |
| Glu | Val | Asn | Glu<br>500 | Pro | Glu | Arg | Leu | Ala<br>505 | Lys | Val | Leu | Ser | Val<br>510 | Leu | Arg |
| Gly | His | Pro<br>515 | Ala | Arg | Thr | Ala | Glu<br>520 | Lys | Ser | Lys | His | Arg<br>525 | Arg | Leu | Asp |
| Arg | Leu<br>530 | Gly | Gly | Thr | Leu | Arg<br>535 | Trp | Lys | Arg | Gln | Pro<br>540 | Ala | Thr | Pro | Ala |
| Leu<br>545 | Met | Ser | Lys | Cys | His<br>550 | Phe | Ser | Leu | Ala | Ala<br>555 | Ala | Met | Arg | His | Lys<br>560 |
| Ser | Lys | Pro | Met | Ser<br>565 | Lys | Ala | Leu | Pro | Cys<br>570 | Trp | Asn | Arg | Ser | Gln<br>575 | Met |
| Ala | Ser | Ala | Thr<br>580 | Ile | Lys | Ser | Lys | Ser<br>585 | Thr | Arg | Phe | Arg | Arg<br>590 | Lys | Ser |
| Cys | Ser | Ser<br>595 | Thr | Lys | Pro | Ser | Ser<br>600 | Ser | Ala | Asp | Arg | Pro<br>605 | Arg | Asn | Asp |
| Gly | Leu | Ser<br>610 | Trp | Arg | Phe | Ala<br>615 | Arg | Val | Gly | Pro | Asn<br>620 | Tyr | Arg | His | Leu |
| Pro<br>625 | His | Gly | Val | Phe | Thr<br>630 | Asp | Arg | Ile | Gly | Val<br>635 | Leu | Thr | Asn | Asp | Phe<br>640 |
| Phe | Val | Asn | Leu | Leu<br>645 | Asp | Met | Asn | Tyr | Glu<br>650 | Trp | Val | Pro | Thr | Asp<br>655 | Ser |
| Gly | Ile | Tyr | Glu<br>660 | Ile | Arg | Asp | Arg | Lys<br>665 | Thr | Gly | Glu | Val | Arg<br>670 | Trp | Thr |
| Ala | Thr | Arg<br>675 | Val | Asp | Leu | Ile | Phe<br>680 | Gly | Ser | Asn | Ser | Ile<br>685 | Leu | Arg | Ser |
| Tyr | Ala<br>690 | Glu | Phe | Tyr | Ala | Gln<br>695 | Asp | Asp | Asn | Gln | Glu<br>700 | Lys | Phe | Val | Arg |
| Asp<br>705 | Phe | Ile | Asn | Ala | Trp<br>710 | Val | Lys | Val | Met | Asn<br>715 | Ala | Asp | Arg | Phe | Asp<br>720 |
| Leu | Val | Lys | Lys | Ala<br>725 | Arg | Glu | Ser | Val | Thr<br>730 | Ala | | | | | |

( 2 ) INFORMATION FOR SEQ ID NO:52:

( i ) SEQUENCE CHARACTERISTICS:
        ( A ) LENGTH: 293 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

| | | | | | | | | | | | | | | |
|---|---|---|---|---|---|---|---|---|---|---|---|---|---|---|
| Thr<br>1 | Thr | Pro | Leu | Val<br>5 | His | Val | Ala | Ser | Val<br>10 | Glu | Lys | Gly | Arg | Ser<br>15 | Tyr |

```
Glu  Asp  Phe  Gln  Lys  Val  Tyr  Asn  Ala  Ile  Ala  Leu  Lys  Leu  Arg  Glu
               20                  25                      30

Asp  Asp  Glu  Tyr  Asp  Asn  Tyr  Ile  Gly  Tyr  Gly  Pro  Val  Leu  Val  Arg
          35                       40                 45

Leu  Ala  Trp  His  Ile  Ser  Gly  Thr  Trp  Asp  Lys  His  Asp  Asn  Thr  Gly
     50                       55                      60

Gly  Ser  Tyr  Gly  Gly  Thr  Tyr  Arg  Phe  Lys  Lys  Glu  Phe  Asn  Asp  Pro
65                       70                      75                          80

Ser  Asn  Ala  Gly  Leu  Gln  Asn  Gly  Phe  Lys  Phe  Leu  Glu  Pro  Ile  His
               85                       90                              95

Lys  Glu  Phe  Pro  Trp  Ile  Ser  Ser  Gly  Asp  Leu  Phe  Ser  Leu  Gly  Gly
               100                      105                     110

Val  Thr  Ala  Val  Glu  Met  Gln  Gly  Pro  Lys  Ile  Pro  Trp  Arg  Cys  Gly
               115                      120                     125

Arg  Val  Asp  Thr  Pro  Glu  Asp  Thr  Thr  Pro  Asp  Asn  Gly  Arg  Leu  Pro
     130                      135                      140

Asp  Ala  Asp  Lys  Asp  Ala  Gly  Tyr  Val  Arg  Thr  Phe  Phe  Gln  Arg  Leu
145                      150                      155                          160

Asn  Met  Asn  Asp  Arg  Glu  Val  Val  Ala  Leu  Met  Gly  Ala  His  Ala  Leu
               165                      170                         175

Gly  Lys  Thr  His  Leu  Lys  Asn  Ser  Gly  Tyr  Glu  Gly  Pro  Trp  Gly  Ala
               180                      185                     190

Ala  Asn  Asn  Val  Phe  Thr  Asn  Glu  Phe  Tyr  Leu  Asn  Leu  Leu  Asn  Glu
          195                      200                     205

Asp  Trp  Lys  Leu  Glu  Lys  Asn  Asp  Ala  Asn  Asn  Glu  Gln  Trp  Asp  Ser
     210                      215                     220

Lys  Ser  Gly  Tyr  Met  Met  Leu  Pro  Thr  Asp  Tyr  Ser  Leu  Ile  Gln  Asp
225                           230                     235                     240

Pro  Lys  Tyr  Leu  Ser  Ile  Val  Lys  Glu  Tyr  Ala  Asn  Asp  Gln  Asp  Lys
                    245                      250                         255

Phe  Phe  Lys  Asp  Phe  Ser  Lys  Ala  Phe  Glu  Lys  Leu  Leu  Glu  Asn  Gly
               260                      265                     270

Ile  Thr  Phe  Pro  Lys  Asp  Ala  Pro  Ser  Pro  Phe  Ile  Phe  Lys  Thr  Leu
               275                      280                     285

Glu  Glu  Gln  Gly  Leu
               290
```

( 2 ) INFORMATION FOR SEQ ID NO:53:

( i ) SEQUENCE CHARACTERISTICS:
        ( A ) LENGTH: 652 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:53:

```
Met  Ser  Thr  Asp  Asp  Thr  His  Asn  Thr  Thr  Lys  Cys  Pro  Phe  His  Gln
1                   5                        10                         15

Gly  Gly  His  Asp  Gln  Ser  Ala  Gly  Ala  Gly  Thr  Thr  Asn  Arg  Asp  Trp
               20                       25                      30

Trp  Pro  Asn  Gln  Leu  Asp  Leu  Leu  His  Gln  His  Ser  Asn  Arg  Ser  Asn
          35                       40                      45

Pro  Leu  Gly  Glu  Asp  Phe  Asp  Tyr  Lys  Glu  Phe  Ser  Lys  Leu  Asp  Tyr
     50                       55                      60
```

```
Tyr Ala Leu Lys Asp Leu Lys Ala Leu Leu Thr Glu Ser Gln Pro Trp
 65                  70                  75                  80

Trp Pro Ala Asp Tyr Gly Tyr Gly Pro Leu Phe Ile Arg Met Ala Trp
                 85                  90                  95

His Gly Ala Gly Thr Tyr Arg Asp Gly Arg Gly Ala Gly Gly Gln
            100                 105                 110

Arg Phe Ala Pro Leu Asn Ser Trp Pro Asp Asn Ala Ser Leu Asp Lys
            115                 120                 125

Ala Arg Arg Leu Leu Trp Pro Ile Lys Lys Tyr Gly Gln Lys Ile Ser
        130                 135                 140

Trp Ala Asp Leu Phe Ile Leu Ala Gly Asn Val Ala Leu Glu Asn Phe
145                 150                 155                 160

Arg Gly Phe Ala Gly Arg Thr Glu Asp Val Trp Glu Pro Asp Leu Asp
                165                 170                 175

Val Asn Trp Gly Glu Lys Ala Trp Leu Thr His Arg His Pro Glu Leu
            180                 185                 190

Ala Lys Ala Pro Leu Gly Ala Thr Glu Met Gly Leu Ile Tyr Val Asn
        195                 200                 205

Pro Glu Gly Pro Asn His Ser Pro Leu Ser Ala Ala Ala Ile Arg
210                 215                 220

Thr Phe Arg Met Gly Met Asn Asp Glu Glu Thr Val Ala Leu Ile Ala
225                 230                 235                 240

Gly Gly His Thr Leu Gly Lys Thr His Gly Ala Gly Pro Ala Ser His
                245                 250                 255

Val Gly Pro Pro Glu Ala Ala Pro Ile Glu Ala Gln Gly Leu Gly Trp
            260                 265                 270

Ala Ser Ser Tyr Gly Ser Gly Val Gly Ala Asp Ala Ile Thr Ser Gly
        275                 280                 285

Glu Val Val Trp Thr Gln Thr Pro Thr Gln Trp Asn Phe Phe Glu Asn
290                 295                 300

Leu Phe Tyr Glu Trp Val Leu Thr Lys Ser Pro Ala Gly Ala Gln Glu
305                 310                 315                 320

Ala Val Asp Gly Ala Pro Asp Ile Ile Pro Asp Pro Phe Asp Pro Ser
                325                 330                 335

Lys Lys Arg Lys Pro Thr Met Leu Val Thr Asp Leu Leu Arg Phe Asp
            340                 345                 350

Pro Glu Tyr Glu Lys Ile Ser Arg Arg Phe Leu Asn Asp Pro Glu Phe
            355                 360                 365

Glu Ala Phe Ala Arg Ala Trp Phe Lys Leu Thr His Arg Asp Met Gly
        370                 375                 380

Pro Lys Arg Tyr Ile Gly Pro Glu Val Pro Lys Glu Asp Leu Ile Trp
385                 390                 395                 400

Gln Asp Pro Pro Gln Tyr Pro Thr Glu Asp Ile Ile Leu Lys Ala Ala
                405                 410                 415

Ile Ala Ala Ser Gly Leu Val Ser Glu Leu Val Ser Ala Trp Ala Ser
            420                 425                 430

Ala Ser Thr Phe Arg Gly Gly Asp Lys Arg Gly Gly Ala Asn Gly Ala
        435                 440                 445

Arg Leu Ala Pro Gln Arg Asp Trp Val Asn Pro Ala Ala Arg Val Leu
        450                 455                 460

Val Leu Glu Glu Ile Gln Thr Lys Ala Ser Leu Ala Asp Ile Val Leu
465                 470                 475                 480

Gly Val Val Gly Glu Lys Ala Ala Ala Ala Gly Leu Ser Ile His
                485                 490                 495
```

| | | | | | | | | | | | | | |
|---|---|---|---|---|---|---|---|---|---|---|---|---|---|
| Val | Pro | Phe | Ala | Pro | Gly | Arg | Asp | Ala | Arg | Gln | Asp | Gln | Thr | Asp | Ile |
| | | | 500 | | | | 505 | | | | | 510 | |
| Glu | Met | Phe | Leu | Leu | Glu | Pro | Ile | Ala | Asp | Gly | Phe | Arg | Asn | Tyr | Arg |
| | | 515 | | | | 520 | | | | 525 | | |
| Ala | Leu | Asp | Val | Ser | Thr | Thr | Glu | Ser | Leu | Ile | Asp | Lys | Ala | Gln | Gln |
| | 530 | | | | 535 | | | | 540 | | | |
| Leu | Thr | Leu | Ala | Pro | Glu | Met | Thr | Val | Leu | Val | Gly | Gly | Met | Arg | Val |
| 545 | | | | | 550 | | | | 555 | | | | 560 |
| Leu | Gly | Asn | Asp | Gly | Pro | Asn | Gly | Val | Phe | Thr | Asp | Arg | Gly | Val | Leu |
| | | | 565 | | | | 570 | | | | 575 | |
| Asn | Asp | Phe | Phe | Val | Asn | Leu | Leu | Asp | Met | Arg | Tyr | Glu | Trp | Lys | Pro |
| | | | 580 | | | | 585 | | | | 590 | | |
| Thr | Asp | Leu | Glu | Gly | Arg | Asp | Arg | Thr | Gly | Glu | Val | Lys | Trp | Thr | Ala |
| | | 595 | | | | 600 | | | | 605 | | |
| Arg | Asp | Leu | Val | Phe | Gly | Ser | Asn | Ser | Val | Leu | Arg | Ala | Leu | Ala | Glu |
| | 610 | | | | | 615 | | | | 620 | | | |
| Val | Tyr | Ala | Ser | Asp | Ala | Glu | Lys | Phe | Val | Lys | Asp | Phe | Val | Ala | Ala |
| 625 | | | | 630 | | | | 635 | | | | 640 |
| Trp | Val | Lys | Val | Met | Asn | Leu | Asp | Arg | Phe | Asp | Leu |
| | | | | 645 | | | | | 650 | | |

( 2 ) INFORMATION FOR SEQ ID NO:54:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

CAGTTCATGG ATCAGAACAA CCCTCTGTCG GGCCTGACCC ACAAGCGCCG GCTGTCG    57

( 2 ) INFORMATION FOR SEQ ID NO:55:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

| | | | | | | | | | | | | | | | |
|---|---|---|---|---|---|---|---|---|---|---|---|---|---|---|---|
| Phe | Phe | Gly | Ser | Ser | Gln | Leu | Ser | Gln | Phe | Met | Asp | Gln | Asn | Asn | Pro |
| 1 | | | | 5 | | | | | 10 | | | | | 15 | |
| Leu | Ser | Glu | Ile | Thr | His | Lys | Arg | Arg | Ile | Ser | Ala | Leu | Gly | Pro | Gly |
| | | | 20 | | | | | 25 | | | | | 30 | | |
| Gly |

( 2 ) INFORMATION FOR SEQ ID NO:56:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Phe Phe Gly Thr Ser Gln Leu Ser Gln Phe Met Asp Gln Asn Asn Pro
 1               5                   10                  15

Leu Ser Gly Leu Thr His Lys Arg Arg Leu Ser Ala Leu Gly Pro Gly
            20                  25                  30

Gly
```

( 2 ) INFORMATION FOR SEQ ID NO:57:

( i ) SEQUENCE CHARACTERISTICS:
        ( A ) LENGTH: 3447 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

```
GTGCCCGGCG CGCCCAACCG AATTTCATTT GCCAAGCTCC GCGAACCGCT TGAGGTTCCG      60
GGGCTACTTG ATGTGCAGAC TGATTCATTT GAGTGGTTGA TCGGATCGCC GTGCTGGCGT     120
GCAGCGGCCG CAAGCCGCGG CGATCTCAAG CCGGTGGGTG GTCTCGAAGA GGTGCTCTAC     180
GAGCTGTCGC CGATCGAGGA TTTCTCCGGC TCAATGTCAT TGTCTTTCTC CGATCCCCGT     240
TTTGACGAAG TCAAGGCGCC CGTCGAAGAG TGCAAAGACA AGGACATGAC GTACGCGGCC     300
CCGCTGTTCG TCACGGCCGA GTTCATCAAC AACAACACCG GGGAGATCAA GAGCCAGACG     360
GTGTTTATGG GCGACTTCCC TATGATGACT GAGAAGGGAA CCTTCATCAT CAACGGGACC     420
GAGCGTGTCG TCGTTAGCCA GCTGGTGCGC TCCCCTGGAG TATACTTCGA CGAGACGATC     480
GACAAGTCCA CAGAAAAGAC GCTGCATAGT GTCAAGGTGA TTCCCAGCCG CGGTGCCTGG     540
TTGGAATTCG ATGTCGATAA ACGCGACACC GTCGGTGTCC GCATTGACCG GAAGCGCCGG     600
CAACCCGTCA CGGTGCTTCT CAAAGCGCTA GGTTGGACCA GTGAGCAGAT CACCGAGCGT     660
TTCGGTTTCT CCGAGATCAT GCGCTCGACG CTGGAGAAGG ACAACACAGT TGGCACCGAC     720
GAGGCGCTGC TAGACATCTA TCGTAAGTTG CGCCCAGGTG AGCCGCCGAC TAAGGAGTCC     780
GCGCAGACGC TGTTGGAGAA CCTGTTCTTC AAGGAGAAAC GCTACGACCT GGCCAGGGTT     840
GGTCGTTACA AGGTCAACAA GAAGCTCGGG TTGCACGCCG GTGAGTTGAT CACGTCGTCC     900
ACGCTGACCG AAGAGGATGT CGTCGCCACC ATAGAGTACC TGGTTCGTCT GCATGAGGGT     960
CAGTCGACAA TGACTGTCCC AGGTGGGGTA GAAGTGCCAG TGGAAACTGA CGATATCGAC    1020
CACTTCGGCA ACCGCCGGCT GCGCACGGTC GGCGAATTGA TCCAGAACCA GATCCGGGTC    1080
GGTATGTCGC GGATGGAGCG GGTGGTCCGG GAGCGGATGA CCACCCAGGA CGTCGAGGCG    1140
ATCACGCCGC AGACGCTGAT CAATATCCGT CCGGTGGTCG CCGCTATCAA GGAATTCTTC    1200
GGCACCAGCC AGCTGTCGCA GTTCATGGAT CAGAACAACC CTCTGTCGGG CCTGACCCAC    1260
AAGCGCCGGC TGTCGGCGCT GGGCCCGGGT GGTTTGTCGC GTGAGCGTGC CGGGCTAGAG    1320
GTCCGTGACG TGCACCCTTC GCACTACGGC CGGATGTGCC CGATCGAGAC TCCGGAGGGC    1380
CCGAACATAG GTCTGATCGG TTCATTGTCG GTGTACGCGC GGGTCAACCC CTTCGGGTTC    1440
ATCGAAACAC CGTACCGCAA AGTGGTTGAC GGTGTGGTCA GCGACGAGAT CGAATACTTG    1500
ACCGCTGACG AGGAAGACCG CCATGTCGTG GCGCAGGCCA ACTCGCCGAT CGACGAGGCC    1560
GGCCGTTCCT CGAGCCGCGC GTGTTGGGTG CGCCGCAAGG CGGGCGAGGT GGAGTACGTG    1620
GCCTCGTCCG AGGTGGATTA CATGGATGTC TCGCCACGCC AGATGGTGTC GGTGGCCACA    1680
GCGATGATTC CGTTCCTTGA GCACGACGAC GCCAACCGTG CCCTGATGGG CGCTAACATG    1740
CAGCGCCAAG CGGTTCCGTT GGTGCGCAGC GAACGACCGT TGGTGGGTAC CGGTATGGAG    1800
```

-continued

| | | | | | |
|---|---|---|---|---|---|
| TTGCGCGCGG | CCATCGACGC | TGGCCACGTC | GTCGTTGCGG | AGAAGTCCGG | GGTGATCGAG | 1860 |
| GAGGTTTCCG | CCGACTACAT | CACCGTGATG | GCCGATGACG | GCACCCGGCG | GACTTATCGG | 1920 |
| ATGCGTAAGT | TCGCGCGCTC | CAACCACGGC | ACCTGCGCCA | ACCAGTCCCC | GATCGTGGAT | 1980 |
| GCGGGGGATC | GGGTCGAGGC | CGGCCAAGTG | ATTGCTGACG | GTCCGTGCAC | TGAGAACGGC | 2040 |
| GAGATGGCGT | TGGGCAAGAA | CTTGCTGGTG | GCGATCAATG | CCGTGGGAGG | GTCAACAACT | 2100 |
| AACGAGGATG | CGATCATCCT | GTCTAACCGA | CTGGTCGAAG | AGGACGTGCT | TACTTCGATT | 2160 |
| CACATTGAGG | AGCATGAGAT | CGACGCCCGT | GACACCAAGC | TGGGTGCTGA | GGAGATCACC | 2220 |
| CGGGACATTC | CCAACGTCTC | CGATGAGGTG | CTAGCCGACT | GGACGAGCG | GGGCATCGTG | 2280 |
| CGGATTGGCG | CGGAGGTTCG | TGACGGTGAT | ATCCTGGTTG | GCAAGGTCAC | CCCGAAGGGG | 2340 |
| GAAACTGAGC | TGACACCGGA | AGAGCGGTTG | CTGCGGGCGA | TCTTCGGCGA | AAAGGCCCGC | 2400 |
| GAGGTCCGTG | ACACGTCGCT | GAAGGTGCCA | CACGGCGAAT | CCGGCAAGGT | GATCGGCATT | 2460 |
| CGGGTGTTCT | CCCATGAGGA | TGACGACGAG | CTGCCCGCCG | GCGTCAACGA | GCTGGTCCGT | 2520 |
| GTCTACGTAG | CCCAGAAGCG | CAAGATCTCT | GACGGTGACA | AGCTGGCTGG | GCGGCACGGC | 2580 |
| AACAAGGGCG | TGATCGGCAA | GATCCTGCCT | GCCGAGGATA | TGCCGTTTCT | GCCAGACGGC | 2640 |
| ACCCCGGTGG | ACATCATCCT | CAACACTCAC | GGGGTGCCGC | GGCGGATGAA | CGTCGGTCAG | 2700 |
| ATCTTGGAAA | CCCACCTTGG | GTGGGTAGCC | AAGTCCGGCT | GGAAGATCGA | CGTGGCCGGC | 2760 |
| GGTATACCGG | ATTGGGCGGT | CAACTTGCCT | GAGGAGTTGT | TGCACGCTGC | GCCCAACCAG | 2820 |
| ATCGTGTCGA | CCCCGGTGTT | CGACGGCGCC | AAGGAAGAGG | AACTACAGGG | CCTGTTGTCC | 2880 |
| TCCACGTTGC | CCAACCGCGA | CGGCGATGTG | ATGGTGGGCG | GCGACGGCAA | GGCGGTGCTC | 2940 |
| TTCGATGGGC | GCAGCGGTGA | GCCGTTCCCT | TATCCGGTGA | CGGTTGGCTA | CATGTACATC | 3000 |
| ATGAAGCTGC | ACCACTTGGT | GGACGACAAG | ATCCACGCCC | GCTCCACCGG | CCCGTACTCG | 3060 |
| ATGATTACCC | AGCAGCCGTT | GGGTGGTAAG | GCACAGTTCG | GTGGCCAGCG | ATTCGGTGAG | 3120 |
| ATGGAGTGCT | GGGCCATGCA | GGCCTACGGT | GCGGCCTACA | CGCTGCAGGA | GCTGTTGACC | 3180 |
| ATCAAGTCCG | ACGACACCGT | CGGTCGGGTC | AAGGTTTACG | AGGCTATCGT | TAAGGGTGAG | 3240 |
| AACATCCCCG | AGCCGGGCAT | CCCCGAGTCG | TTCAAGGTGC | TGCTCAAGGA | GTTACAGTCG | 3300 |
| CTGTGTCTCA | ACGTCGAGGT | GCTGTCGTCC | GACGGTGCGG | CGATCGAGTT | GCGCGAAGGT | 3360 |
| GAGGATGAGG | ACCTCGAGCG | GGCTGCGGCC | AACCTCGGTA | TCAACTTGTC | CCGCAACGAA | 3420 |
| TCGGCGTCCA | TAGAAGATCT | GGCTTAG | | | | 3447 |

( 2 ) INFORMATION FOR SEQ ID NO:58:

( i ) SEQUENCE CHARACTERISTICS:
        ( A ) LENGTH: 1148 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Val Pro Gly Ala Pro Asn Arg Ile Ser Phe Ala Lys Leu Arg Glu Pro
 1               5                  10                  15

Leu Glu Val Pro Gly Leu Leu Asp Val Gln Thr Asp Ser Phe Glu Trp
            20                  25                  30

Leu Ile Gly Ser Pro Cys Trp Arg Ala Ala Ala Ala Ser Arg Gly Asp
        35                  40                  45
```

| | | | | | | | | | | | | | | |
|---|---|---|---|---|---|---|---|---|---|---|---|---|---|---|
| Leu | Lys | Pro | Val | Gly | Gly | Leu | Glu | Glu | Val | Leu | Tyr | Glu | Leu | Ser | Pro |
| | 50 | | | | 55 | | | | | 60 | | | | |
| Ile | Glu | Asp | Phe | Ser | Gly | Ser | Met | Ser | Leu | Ser | Phe | Ser | Asp | Pro | Arg |
| 65 | | | | | 70 | | | | 75 | | | | | 80 |
| Phe | Asp | Glu | Val | Lys | Ala | Pro | Val | Glu | Glu | Cys | Lys | Asp | Lys | Asp | Met |
| | | | | 85 | | | | | 90 | | | | | 95 |
| Thr | Tyr | Ala | Ala | Pro | Leu | Phe | Val | Thr | Ala | Glu | Phe | Ile | Asn | Asn | Asn |
| | | | | 100 | | | | 105 | | | | | 110 | |
| Thr | Gly | Glu | Ile | Lys | Ser | Gln | Thr | Val | Phe | Met | Gly | Asp | Phe | Pro | Met |
| | | | 115 | | | | 120 | | | | | 125 | | |
| Met | Thr | Glu | Lys | Gly | Thr | Phe | Ile | Ile | Asn | Gly | Thr | Glu | Arg | Val | Val |
| | | 130 | | | | 135 | | | | | 140 | | | | |
| Val | Ser | Gln | Leu | Val | Arg | Ser | Pro | Gly | Val | Tyr | Phe | Asp | Glu | Thr | Ile |
| 145 | | | | | 150 | | | | | 155 | | | | | 160 |
| Asp | Lys | Ser | Thr | Glu | Lys | Thr | Leu | His | Ser | Val | Lys | Val | Ile | Pro | Ser |
| | | | | 165 | | | | 170 | | | | | 175 | | |
| Arg | Gly | Ala | Trp | Leu | Glu | Phe | Asp | Val | Asp | Lys | Arg | Asp | Thr | Val | Gly |
| | | | 180 | | | | | 185 | | | | | 190 | | |
| Val | Arg | Ile | Asp | Arg | Lys | Arg | Gln | Pro | Val | Thr | Val | Leu | Leu | Lys |
| | | 195 | | | | | 200 | | | | | 205 | | |
| Ala | Leu | Gly | Trp | Thr | Ser | Glu | Gln | Ile | Thr | Glu | Arg | Phe | Gly | Phe | Ser |
| | 210 | | | | | 215 | | | | | 220 | | | | |
| Glu | Ile | Met | Arg | Ser | Thr | Leu | Glu | Lys | Asp | Asn | Thr | Val | Gly | Thr | Asp |
| 225 | | | | | 230 | | | | | 235 | | | | | 240 |
| Glu | Ala | Leu | Leu | Asp | Ile | Tyr | Arg | Lys | Leu | Arg | Pro | Gly | Glu | Pro | Pro |
| | | | | 245 | | | | | 250 | | | | | 255 | |
| Thr | Lys | Glu | Ser | Ala | Gln | Thr | Leu | Leu | Glu | Asn | Leu | Phe | Phe | Lys | Glu |
| | | | | 260 | | | | | 265 | | | | | 270 | |
| Lys | Arg | Tyr | Asp | Leu | Ala | Arg | Val | Gly | Arg | Tyr | Lys | Val | Asn | Lys | Lys |
| | | | 275 | | | | | 280 | | | | | 285 | | |
| Leu | Gly | Leu | His | Ala | Gly | Glu | Leu | Ile | Thr | Ser | Ser | Thr | Leu | Thr | Glu |
| | 290 | | | | | 295 | | | | | 300 | | | | |
| Glu | Asp | Val | Val | Ala | Thr | Ile | Glu | Tyr | Leu | Val | Arg | Leu | His | Glu | Gly |
| 305 | | | | | 310 | | | | | 315 | | | | | 320 |
| Gln | Ser | Thr | Met | Thr | Val | Pro | Gly | Gly | Val | Glu | Val | Pro | Val | Glu | Thr |
| | | | | 325 | | | | | 330 | | | | | 335 | |
| Asp | Asp | Ile | Asp | His | Phe | Gly | Asn | Arg | Arg | Leu | Arg | Thr | Val | Gly | Glu |
| | | | 340 | | | | | 345 | | | | | 350 | | |
| Leu | Ile | Gln | Asn | Gln | Ile | Arg | Val | Gly | Met | Ser | Arg | Met | Glu | Arg | Val |
| | | | 355 | | | | | 360 | | | | | 365 | | |
| Val | Arg | Glu | Arg | Met | Thr | Thr | Gln | Asp | Val | Glu | Ala | Ile | Thr | Pro | Gln |
| | 370 | | | | | 375 | | | | | 380 | | | | |
| Thr | Leu | Ile | Asn | Ile | Arg | Pro | Val | Val | Ala | Ala | Ile | Lys | Glu | Phe | Phe |
| 385 | | | | | 390 | | | | | 395 | | | | | 400 |
| Gly | Thr | Ser | Gln | Leu | Ser | Gln | Phe | Met | Asp | Gln | Asn | Asn | Pro | Leu | Ser |
| | | | | 405 | | | | | 410 | | | | | 415 | |
| Gly | Leu | Thr | His | Lys | Arg | Arg | Leu | Ser | Ala | Leu | Gly | Pro | Gly | Gly | Leu |
| | | | | 420 | | | | | 425 | | | | | 430 | |
| Ser | Arg | Glu | Arg | Ala | Gly | Leu | Glu | Val | Arg | Asp | Val | His | Pro | Ser | His |
| | | | 435 | | | | | 440 | | | | | 445 | | |
| Tyr | Gly | Arg | Met | Cys | Pro | Ile | Glu | Thr | Pro | Glu | Gly | Pro | Asn | Ile | Gly |
| | | | 450 | | | | | 455 | | | | | 460 | | |
| Leu | Ile | Gly | Ser | Leu | Ser | Val | Tyr | Ala | Arg | Val | Asn | Pro | Phe | Gly | Phe |
| 465 | | | | | 470 | | | | | 475 | | | | | 480 |

| | | | | | | | | | | | | | | |
|---|---|---|---|---|---|---|---|---|---|---|---|---|---|---|
| Ile | Glu | Thr | Pro | Tyr 485 | Arg | Lys | Val | Val | Asp 490 | Gly | Val | Val | Ser | Asp Glu 495 |
| Ile | Glu | Tyr | Leu 500 | Thr | Ala | Asp | Glu | Asp 505 | Arg | His | Val | Val 510 | Ala | Gln |
| Ala | Asn | Ser 515 | Pro | Ile | Asp | Glu | Ala 520 | Gly | Arg | Ser | Ser 525 | Ser | Arg | Ala Cys |
| Trp | Val 530 | Arg | Arg | Lys | Ala | Gly 535 | Glu | Val | Glu | Tyr | Val 540 | Ala | Ser | Ser Glu |
| Val 545 | Asp | Tyr | Met | Asp | Val 550 | Ser | Pro | Arg | Gln | Met 555 | Val | Ser | Val | Ala Thr 560 |
| Ala | Met | Ile | Pro | Phe 565 | Leu | Glu | His | Asp | Asp 570 | Ala | Asn | Arg | Ala | Leu Met 575 |
| Gly | Ala | Asn | Met 580 | Gln | Arg | Gln | Ala | Val 585 | Pro | Leu | Val | Arg 590 | Ser | Glu Arg |
| Pro | Leu | Val 595 | Gly | Thr | Gly | Met | Glu 600 | Leu | Arg | Ala | Ala | Ile 605 | Asp | Ala Gly |
| His | Val 610 | Val | Val | Ala | Glu | Lys 615 | Ser | Gly | Val | Ile | Glu 620 | Glu | Val | Ser Ala |
| Asp 625 | Tyr | Ile | Thr | Val | Met 630 | Ala | Asp | Asp | Gly | Thr 635 | Arg | Arg | Thr | Tyr Arg 640 |
| Met | Arg | Lys | Phe | Ala 645 | Arg | Ser | Asn | His | Gly 650 | Thr | Cys | Ala | Asn | Gln Ser 655 |
| Pro | Ile | Val | Asp 660 | Ala | Gly | Asp | Arg | Val 665 | Glu | Ala | Gly | Gln 670 | Val | Ile Ala |
| Asp | Gly | Pro 675 | Cys | Thr | Glu | Asn | Gly 680 | Glu | Met | Ala | Leu | Gly 685 | Lys | Asn Leu |
| Leu | Val 690 | Ala | Ile | Asn | Ala | Val 695 | Gly | Gly | Ser | Thr | Thr 700 | Asn | Glu | Asp Ala |
| Ile 705 | Ile | Leu | Ser | Asn | Arg 710 | Leu | Val | Glu | Glu | Asp 715 | Val | Leu | Thr | Ser Ile 720 |
| His | Ile | Glu | Glu | His 725 | Glu | Ile | Asp | Ala | Arg 730 | Asp | Thr | Lys | Leu | Gly Ala 735 |
| Glu | Glu | Ile | Thr 740 | Arg | Asp | Ile | Pro | Asn 745 | Val | Ser | Asp | Glu 750 | Val | Leu Ala |
| Asp | Leu | Asp 755 | Glu | Arg | Gly | Ile | Val 760 | Arg | Ile | Gly | Ala | Glu 765 | Val | Arg Asp |
| Gly | Asp 770 | Ile | Leu | Val | Gly | Lys 775 | Val | Thr | Pro | Lys | Gly 780 | Glu | Thr | Glu Leu |
| Thr 785 | Pro | Glu | Glu | Arg | Leu 790 | Leu | Arg | Ala | Ile | Phe 795 | Gly | Glu | Lys | Ala Arg 800 |
| Glu | Val | Arg | Asp | Thr 805 | Ser | Leu | Lys | Val | Pro 810 | His | Gly | Glu | Ser | Gly Lys 815 |
| Val | Ile | Gly | Ile 820 | Arg | Val | Phe | Ser | His 825 | Glu | Asp | Asp | Glu 830 | Leu | Pro |
| Ala | Gly | Val 835 | Asn | Glu | Leu | Val | Arg 840 | Val | Tyr | Val | Ala | Gln 845 | Lys | Arg Lys |
| Ile | Ser | Asp 850 | Gly | Asp | Lys | Leu | Ala 855 | Gly | Arg | His | Gly | Asn 860 | Lys | Gly Val |
| Ile | Gly 865 | Lys | Ile | Leu | Pro | Ala 870 | Glu | Asp | Met | Pro | Phe 875 | Leu | Pro | Asp Gly 880 |
| Thr | Pro | Val | Asp | Ile 885 | Ile | Leu | Asn | Thr | His 890 | Gly | Val | Pro | Arg | Arg Met 895 |

```
Asn  Val  Gly  Gln  Ile  Leu  Glu  Thr  His  Leu  Gly  Trp  Val  Ala  Lys  Ser
               900                      905                      910

Gly  Trp  Lys  Ile  Asp  Val  Ala  Gly  Gly  Ile  Pro  Asp  Trp  Ala  Val  Asn
     915                      920                      925

Leu  Pro  Glu  Glu  Leu  Leu  His  Ala  Ala  Pro  Asn  Gln  Ile  Val  Ser  Thr
          930                      935                      940

Pro  Val  Phe  Asp  Gly  Ala  Lys  Glu  Glu  Glu  Leu  Gln  Gly  Leu  Leu  Ser
945                           950                      955                960

Ser  Thr  Leu  Pro  Asn  Arg  Asp  Gly  Asp  Val  Met  Val  Gly  Gly  Asp  Gly
                    965                      970                      975

Lys  Ala  Val  Leu  Phe  Asp  Gly  Arg  Ser  Gly  Glu  Pro  Phe  Pro  Tyr  Pro
               980                      985                      990

Val  Thr  Val  Gly  Tyr  Met  Tyr  Ile  Met  Lys  Leu  His  His  Leu  Val  Asp
          995                      1000                     1005

Asp  Lys  Ile  His  Ala  Arg  Ser  Thr  Gly  Pro  Tyr  Ser  Met  Ile  Thr  Gln
     1010                     1015                     1020

Gln  Pro  Leu  Gly  Gly  Lys  Ala  Gln  Phe  Gly  Gly  Gln  Arg  Phe  Gly  Glu
1025                     1030                     1035                     1040

Met  Glu  Cys  Trp  Ala  Met  Gln  Ala  Tyr  Gly  Ala  Ala  Tyr  Thr  Leu  Gln
                    1045                     1050                     1055

Glu  Leu  Leu  Thr  Ile  Lys  Ser  Asp  Asp  Thr  Val  Gly  Arg  Val  Lys  Val
               1060                     1065                     1070

Tyr  Glu  Ala  Ile  Val  Lys  Gly  Glu  Asn  Ile  Pro  Glu  Pro  Gly  Ile  Pro
          1075                     1080                     1085

Glu  Ser  Phe  Lys  Val  Leu  Leu  Lys  Glu  Leu  Gln  Ser  Leu  Cys  Leu  Asn
     1090                     1095                     1100

Val  Glu  Val  Leu  Ser  Ser  Asp  Gly  Ala  Ala  Ile  Glu  Leu  Arg  Glu  Gly
1105                     1110                     1115                     1120

Glu  Asp  Glu  Asp  Leu  Glu  Arg  Ala  Ala  Ala  Asn  Leu  Gly  Ile  Asn  Leu
                    1125                     1130                     1135

Ser  Arg  Asn  Glu  Ser  Ala  Ser  Ile  Glu  Asp  Leu  Ala
                    1140                     1145
```

( 2 ) INFORMATION FOR SEQ ID NO:59:

( i ) SEQUENCE CHARACTERISTICS:
        ( A ) LENGTH: 432 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

```
GGCAACCGCC  GCCTGCGTAC  GGTCGGCGAG  CTGATCCAAA  ACCAGATCCG  GGTCGGCATG    60
TCGCGGATGG  AGCGGGTGGT  CCGGGAGCGG  ATGACCACCC  AGGACGTGGA  GGCGATCACA   120
CCGCAGACGT  TGATCAACAT  CCGGCCGGTG  GTCGCCGCGA  TCAAGGAGTT  CTTCGGCACC   180
AGCCAGCTGA  GCCAATTCAT  GGACCAGAAC  AACCCGCTGT  CGGGGTTGAC  GCACAAGCGC   240
CGACTGTCGG  CGCTGGGGCC  CGGCGGTCTG  TCACGTGAGC  GTGCCGGGCT  GGAGGTCCGC   300
GACGTGCACC  CGTCGCACTA  CGGCCGGATG  TGCCCGATCG  AAACCCCTGA  GGGGCCCAAC   360
ATCGGTCTGA  TCGGCTCGCT  GTCGGTGTAC  GCGCGGGTCA  ACCCGTTCGG  GTTCATCGAA   420
ACGCCGTACC  GC                                                          432
```

( 2 ) INFORMATION FOR SEQ ID NO:60:

(i) SEQUENCE CHARACTERISTICS:
(A) LENGTH: 144 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:60:

| Gly | Asn | Arg | Arg | Leu | Arg | Thr | Val | Gly | Glu | Leu | Ile | Gln | Asn | Gln | Ile |
|---|---|---|---|---|---|---|---|---|---|---|---|---|---|---|---|
| 1 | | | | 5 | | | | | 10 | | | | | 15 | |
| Arg | Val | Gly | Met | Ser | Arg | Met | Glu | Arg | Val | Val | Arg | Glu | Arg | Met | Thr |
| | | | 20 | | | | | 25 | | | | | 30 | | |
| Thr | Gln | Asp | Val | Glu | Ala | Ile | Thr | Pro | Gln | Thr | Leu | Ile | Asn | Ile | Arg |
| | | 35 | | | | | 40 | | | | | 45 | | | |
| Pro | Val | Val | Ala | Ala | Ile | Lys | Glu | Phe | Phe | Gly | Thr | Ser | Gln | Leu | Ser |
| | 50 | | | | | 55 | | | | | 60 | | | | |
| Gln | Phe | Met | Asp | Gln | Asn | Asn | Pro | Leu | Ser | Gly | Leu | Thr | His | Lys | Arg |
| 65 | | | | | 70 | | | | | 75 | | | | | 80 |
| Arg | Leu | Ser | Ala | Leu | Gly | Pro | Gly | Gly | Leu | Ser | Arg | Glu | Arg | Ala | Gly |
| | | | | 85 | | | | | 90 | | | | | 95 | |
| Leu | Glu | Val | Arg | Asp | Val | His | Pro | Ser | His | Tyr | Gly | Arg | Met | Cys | Pro |
| | | | 100 | | | | | 105 | | | | | 110 | | |
| Ile | Glu | Thr | Pro | Glu | Gly | Pro | Asn | Ile | Gly | Leu | Ile | Gly | Ser | Leu | Ser |
| | | 115 | | | | | 120 | | | | | 125 | | | |
| Val | Tyr | Ala | Arg | Val | Asn | Pro | Phe | Gly | Phe | Ile | Glu | Thr | Pro | Tyr | Arg |
| | 130 | | | | | 135 | | | | | 140 | | | | |

(2) INFORMATION FOR SEQ ID NO:61:

(i) SEQUENCE CHARACTERISTICS:
(A) LENGTH: 462 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:61:

```
ATGCCCGATC ACAGGGCACT GCGGCAGGGA ATAATTGCAC TACGCCAACA TGTTAACAAC      60
GAACACAATT TACCTGGGAG CCGGTATATG CCCACCATTC AGCAGCTGGT ACGCAAGGGT     120
CGTCGAGACA AGATTGGCAA GGTCAAGACT GCGGCTCTGA AGGGCAACCC ACAGCGTCGC     180
GGTGTTTGCA CCCGTGTGTA CACTTCCACC CCGAAGAAGC CGAACTCGGC GCTTCGCAAG     240
GTTGCCCGCG TGAAGCTGAC GAGTCAGGTT GAGGTCACAG CGTACATACC AGGCGAGGGT     300
CACAACCTAC AGGAACACTC CATGGTGTTG GTGCGTGGTG GCCGGGTGAA AGATCTGCCT     360
GGTGTGCGTT ACAAAATCAT TCGCGGTTCG CTCGACACCC AGGGTGTCAA GAACCGGAAG     420
CAGGCTCGTA GCCGCTATGG AGCCAAGAAG GAGAAGAGCT GA                        462
```

(2) INFORMATION FOR SEQ ID NO:62:

(i) SEQUENCE CHARACTERISTICS:
(A) LENGTH: 124 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:62:

```
        Met    Pro    Thr    Ile    Gln    Gln    Leu    Val    Arg    Lys    Gly    Arg    Arg    Asp    Lys    Ile
         1                           5                                  10                                         15

Gly    Lys    Val    Lys    Thr    Ala    Ala    Leu    Lys    Gly    Asn    Pro    Gln    Arg    Arg    Gly
                              20                           25                                  30

Val    Cys    Thr    Arg    Val    Tyr    Thr    Ser    Thr    Pro    Lys    Lys    Pro    Asn    Ser    Ala
                       35                                  40                                  45

Leu    Arg    Lys    Val    Ala    Arg    Val    Lys    Leu    Thr    Ser    Gln    Val    Glu    Val    Thr
                50                                  55                                  60

Ala    Tyr    Ile    Pro    Gly    Glu    Gly    His    Asn    Leu    Gln    Glu    His    Ser    Met    Val
        65                                  70                                  75                                  80

Leu    Val    Arg    Gly    Gly    Arg    Val    Lys    Asp    Leu    Pro    Gly    Val    Arg    Tyr    Lys
                                    85                                  90                                  95

Ile    Ile    Arg    Gly    Ser    Leu    Asp    Thr    Gln    Gly    Val    Lys    Asn    Arg    Lys    Gln
                              100                                 105                                110

Ala    Arg    Ser    Arg    Tyr    Gly    Ala    Lys    Lys    Glu    Lys    Ser
                              115                                 120
```

( 2 ) INFORMATION FOR SEQ ID NO:63:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

```
CCCACCATTC   AGCAGCTGGT   CCGCAAGGGT   CGTCGGGACA   AGATCAGTAA   GGTCAAGACC        60
GCGGCTCTGA   AGGGCAGCCC   GCAGCGTCGT   GGTGTATGCA   CCCGCGTGTA   CACCACCACT       120
CCGAAGAAGC   CGAACTCGGC   GCTTCGGAAG   GTTGCCCGCG   TGAAGTTGAC   GAGTCAGGTC       180
GAGGTCACGG   CGTACATTCC   CGGCGAGGCG   CACAACCTGC   AGGAGCACTC   GATGGTGCTG       240
GTGCGCGGCG   GCCGGGTGAA   GGACCTGCCT   GGTGTGCGCT   ACAAGATCAT   TCGCGGTTCG       300
CTCGAC                                                                            306
```

( 2 ) INFORMATION FOR SEQ ID NO:64:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

```
        Pro    Thr    Ile    Gln    Gln    Leu    Val    Arg    Lys    Gly    Arg    Arg    Asp    Lys    Ile    Ser
         1                           5                                  10                                         15

Lys    Val    Lys    Thr    Ala    Ala    Leu    Lys    Gly    Ser    Pro    Gln    Arg    Arg    Gly    Val
                              20                           25                                  30

Cys    Thr    Arg    Val    Tyr    Thr    Thr    Thr    Pro    Lys    Lys    Pro    Asn    Ser    Ala    Leu
                       35                                  40                                  45

Arg    Lys    Val    Ala    Arg    Val    Lys    Leu    Thr    Ser    Gln    Val    Glu    Val    Thr    Ala
                50                                  55                                  60

Tyr    Ile    Pro    Gly    Glu    Ala    His    Asn    Leu    Gln    Glu    His    Ser    Met    Val    Leu
        65                                  70                                  75                                  80

Val    Arg    Gly    Gly    Arg    Val    Lys    Asp    Leu    Pro    Gly    Val    Arg    Tyr    Lys    Ile
                                    85                                  90                                  95
```

```
                Ile  Arg  Gly  Ser  Leu  Asp
                               100
```

( 2 ) INFORMATION FOR SEQ ID NO:65:

( i ) SEQUENCE CHARACTERISTICS:
        ( A ) LENGTH: 264 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

```
CGCAAGGGTC  GTCGAGACAA  GATTGGCAAG  GTCAAGACCG  CGGCTCTGAA  GGGCAGCCCG        60

CAGCGTCGTG  GTGTATGCAC  CCGCGTGTAC  ACCACCACTC  CGAAGAAGCC  GAACTCGGCG       120

CTTCGGAAGG  TTGCCCGCGT  GAAGTTGACG  AGTCAGGTCG  AGGTCACGGC  GTACATTCCC       180

GGCGAGGCGC  ACAACCTGCA  GGAGCACTCG  ATGGTGCTGG  TGCGCGGCGG  CCGGGTGAAG       240

GACCTGCCTG  GTGTGCGCTA  CAAG                                                 264
```

( 2 ) INFORMATION FOR SEQ ID NO:66:

( i ) SEQUENCE CHARACTERISTICS:
        ( A ) LENGTH: 88 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:66:

```
Arg  Lys  Gly  Arg  Arg  Asp  Lys  Ile  Gly  Lys  Val  Lys  Thr  Ala  Ala  Leu
 1                    5                        10                         15

Lys  Gly  Asn  Pro  Gln  Arg  Arg  Gly  Val  Cys  Thr  Arg  Val  Tyr  Thr  Ser
               20                       25                    30

Thr  Pro  Lys  Lys  Pro  Asn  Ser  Ala  Leu  Arg  Lys  Val  Ala  Arg  Val  Lys
          35                        40                    45

Leu  Thr  Ser  Gln  Val  Glu  Val  Thr  Ala  Tyr  Ile  Pro  Gly  Glu  Gly  His
     50                         55                       60

Asn  Leu  Gln  Glu  His  Ser  Met  Val  Leu  Val  Arg  Gly  Gly  Arg  Val  Lys
65                       70                       75                         80

Asp  Leu  Pro  Gly  Val  Arg  Tyr  Lys
               85
```